United States Patent
Tien

(10) Patent No.: US 12,029,792 B2
(45) Date of Patent: Jul. 9, 2024

(54) STEREOCOMPLEXES FOR THE DELIVERY OF ANTI-CANCER AGENTS

(71) Applicant: Der-Yang Tien, Pasadena, CA (US)

(72) Inventor: Der-Yang Tien, Pasadena, CA (US)

( * ) Notice: Subject to any disclaimer, the term of this patent is extended or adjusted under 35 U.S.C. 154(b) by 224 days.

(21) Appl. No.: 17/299,561

(22) PCT Filed: Dec. 3, 2019

(86) PCT No.: PCT/US2019/064140
§ 371 (c)(1),
(2) Date: Jun. 3, 2021

(87) PCT Pub. No.: WO2020/117742
PCT Pub. Date: Jun. 11, 2020

(65) Prior Publication Data
US 2022/0072139 A1 Mar. 10, 2022

Related U.S. Application Data

(60) Provisional application No. 62/893,863, filed on Aug. 30, 2019, provisional application No. 62/775,076, filed on Dec. 4, 2018.

(51) Int. Cl.
*A61K 47/59* (2017.01)
*A61K 31/05* (2006.01)
(Continued)

(52) U.S. Cl.
CPC ............ *A61K 47/593* (2017.08); *A61K 31/05* (2013.01); *A61K 31/165* (2013.01);
(Continued)

(58) Field of Classification Search
CPC .... A61K 47/593; A61K 47/60; A61K 33/243; A61K 31/05; A61K 31/165; A61P 35/00
See application file for complete search history.

(56) References Cited

U.S. PATENT DOCUMENTS

| 6,251,382 B1 | 6/2001 | Greenwald et al. |
| 6,441,163 B1 | 8/2002 | Chari et al. |

(Continued)

FOREIGN PATENT DOCUMENTS

| CN | 105031672 A | 11/2015 |
| CN | 106139160 | 11/2016 |

(Continued)

OTHER PUBLICATIONS

Wang et al., "Poly(Ethylene Glycol)-Polylactide Micelles for Cancer Therapy", Frontiers in Pharmacology, vol. 9, article 202, Mar. 2018. (Year: 2018).*

(Continued)

*Primary Examiner* — Jianfeng Song
(74) *Attorney, Agent, or Firm* — Thomas | Horstemeyer, LLP

(57) ABSTRACT

Disclosed herein are stereocomplexes for the delivery of one or more anti-cancer agents. The stereocomplexes exhibit low toxicity and are biodegradable while also providing for controlled release of one or more anti-cancer agents at tumor sites. The stereocomplexes can be designed such that the anti-cancer agents operate synergistically and may optionally include additional targeting groups and functionalities. The stereocomplexes disclosed herein can be combined with pharmaceutically-acceptable carriers and/or excipients to form pharmaceutical compositions. By varying the amount of each anti-cancer agent in the stereocomplex, specific types of tumors and cancer cell lines can be treated.

54 Claims, 47 Drawing Sheets

(51) Int. Cl.

| | | |
|---|---|---|
| A61K 31/165 | (2006.01) | |
| A61K 31/337 | (2006.01) | |
| A61K 31/352 | (2006.01) | |
| A61K 31/353 | (2006.01) | |
| A61K 31/41 | (2006.01) | |
| A61K 31/4178 | (2006.01) | |
| A61K 31/4184 | (2006.01) | |
| A61K 31/4245 | (2006.01) | |
| A61K 31/4412 | (2006.01) | |
| A61K 31/4418 | (2006.01) | |
| A61K 31/496 | (2006.01) | |
| A61K 31/506 | (2006.01) | |
| A61K 31/513 | (2006.01) | |
| A61K 31/519 | (2006.01) | |
| A61K 31/537 | (2006.01) | |
| A61K 31/5513 | (2006.01) | |
| A61K 31/573 | (2006.01) | |
| A61K 31/704 | (2006.01) | |
| A61K 31/7048 | (2006.01) | |
| A61K 31/7068 | (2006.01) | |
| A61K 33/243 | (2019.01) | |
| A61K 47/60 | (2017.01) | |
| A61P 35/00 | (2006.01) | |

(52) U.S. Cl.
CPC .......... *A61K 31/337* (2013.01); *A61K 31/352* (2013.01); *A61K 31/353* (2013.01); *A61K 31/41* (2013.01); *A61K 31/4178* (2013.01); *A61K 31/4184* (2013.01); *A61K 31/4245* (2013.01); *A61K 31/4412* (2013.01); *A61K 31/4418* (2013.01); *A61K 31/496* (2013.01); *A61K 31/506* (2013.01); *A61K 31/513* (2013.01); *A61K 31/519* (2013.01); *A61K 31/537* (2013.01); *A61K 31/5513* (2013.01); *A61K 31/573* (2013.01); *A61K 31/704* (2013.01); *A61K 31/7048* (2013.01); *A61K 31/7068* (2013.01); *A61K 33/243* (2019.01); *A61K 47/60* (2017.08); *A61P 35/00* (2018.01)

(56) References Cited

U.S. PATENT DOCUMENTS

| | | | |
|---|---|---|---|
| 6,596,757 | B1 | 7/2003 | Chari et al. |
| 6,716,821 | B2 | 4/2004 | Zhao et al. |
| 7,276,499 | B2 | 10/2007 | Chari et al. |
| 7,601,354 | B2 | 10/2009 | Chari |
| 7,691,962 | B2 | 4/2010 | Boyd et al. |
| 7,842,676 | B2 | 11/2010 | Janoff et al. |
| 7,850,990 | B2 | 12/2010 | Tardi et al. |
| 8,092,828 | B2 | 1/2012 | Louie et al. |
| 8,236,319 | B2 | 8/2012 | Chari et al. |
| 8,461,117 | B2 | 6/2013 | Sufi et al. |
| 8,518,437 | B2 | 8/2013 | Tardi et al. |
| 9,504,756 | B2 | 11/2016 | Lyon et al. |
| 9,687,562 | B2 | 6/2017 | Satchi-Fainaro et al. |
| 2006/0233814 | A1 | 10/2006 | Goldmakher et al. |
| 2009/0306101 | A1 | 12/2009 | Solca et al. |
| 2019/0083633 | A1* | 3/2019 | Kwon ............... A61P 35/00 |

FOREIGN PATENT DOCUMENTS

| | | |
|---|---|---|
| CN | 106581691 A1 | 4/2017 |
| EP | 2644194 A2 | 10/2013 |
| EP | 2913353 A1 | 9/2015 |
| KR | 20170110533 A | 10/2017 |
| WO | 2006007402 A2 | 1/2006 |
| WO | 2016145096 A1 | 9/2016 |

OTHER PUBLICATIONS

Wang et al., "Poly(Ethylene Glycol)-Polylactide Micelles for Cancer Therapy", Frontiers in Pharmacology, Mar. 2018, vol. 9, p. 1-15. (Year: 2018).*

Yasugi et al., "Sugar-Installed Polymer Micelles: Synthesis and Micellization of Poly(ethylene glycol)-Poly(D,L-lactide) Block Copolymers Having Sugar Groups at the PEG Chain End", Macromolecules 1999, 32, 8024-8032. (Year: 1999).*

Yoo HS, et al., "Doxorubicin-conjugated biodegradable polymeric micelles having acid-cleavable linkages," Journal of Controlled Release 2002; 82:17-27.

Shen K, et al . . . , "Targeted sustained delivery of antineoplastic agent with multicomponent polylactide stereocomplex micelle," Nanomedicine 2017; 13(3):1279-1288.

Kerr C, et al., "Luminescent difluoroboron beta-diketonate PLA-PEG nanoparticle," Biomacromolecules 2017; 18(2):551-561.

Hiemstra et al: "In vitro and in vivo protein delivery from in situ forming poly(ethylene glycol)-poly(lactide) hydrogels". Journal of Controlled Release, Elsevier. Amsterdam, NL, vol. 119, No. 3, May 22, 2007.

International Report on Patentability for PCT/US2019/064140 mailed Nov. 25, 2020.

Taiwanese Search Report for Application No. 108144097 mailed Aug. 30, 2019.

Baabur-Cohen, H. "In vivo comparative study of distinct polymeric architectures bearing a combination of paclitaxel and doxorubicin at a synergistic ratio" Journal of Controlled Release 257 (2017) 118-131. http://dx.doi.org/10.1016/j.iconrel.2016.06.037.

Vogus, D. "A hyaluronic acid conjugate engineered to synergistically and sequentially deliver gemcitabine and doxorubicin to treat triple negative breast cancer" Journal of Controlled Release 267 (2017) 191-202. http://dx.doi.org/10.1016/j.jconrel.2017.08.016.

Vogus, D. "A review on engineering polymer drug conjugates to improve combination chemotherapy" Current Opinion in Colloid & Interface Science 31 (2017) 75-85. http://dx.doi.org/10.1016/j.cocis.2017.08.002.

Claudia Brunetti, Luisa Anelli, Antonella Zagaria, Giorgina Specchia & Francesco Albano (2017) CPX-351 in acute myeloid leukemia: can a new formulation maximize the efficacy of old compounds Expert Review of Hematology, 10:10, 853-862, DOI:10.1080/17474086.2017.1369400.

Feldman, Eric J. "First-In-Man Study of CPX-351: A Liposomal Carrier Containing Cytarabine and Daunorubicin in a Fixed 5:1 Molar Ratio for the Treatment of Relapsed and Refractory Acute Myeloid Leukemia" American Society of Clinical Oncology. DOI: 10.1200/JCO.2010.30.5961.

Tardi, Paul "In vivo maintenance of synergistic cytarabine:daunorubicin ratios greatly enhances therapeutic efficacy" Leukemia Research 33 (2009) 129-139. DOI:10.1016/j.leukres.2008.06.028.

Yang, Ruinan "Combination therapy of paclitaxel and cyclopamine polymer-drug conjugates to treat advanced prostate cancer" Nanomedicine: Nanotechnology, Biology, and Medicine 13 (2017) 391-401 DOI: http://dx.doi.org/10.1016/j.nano.2016.07.017.

Kang et al. BMC Medical Research Methodology 2013, 13:77 "Inference of synergy/antagonism between anticancer drugs from the pooled analysis of clinical trials".

Meng, Hao "A Smart Nano-Prodrug Platform with Reactive Drug Loading, Superb Stability, and Fast Responsive Drug Release for Targeted Cancer Therapy" Macromol. Biosci. 2017, DOI: 10.1002/mabi.201600518.

Zhong et al, 2017, Nanotechnology, at press: https://doi.org/10.1088/1361-6528/aa76cc.

P. Zhong, et al., αvβ3 Integrin-targeted reduction-sensitive micellar mertansine prodrug: Superb drug loading, enhanced stability, and effective inhibition of melanoma growth in vivo, J. Control. Release (2016), http://dx.doi.org/10.1016/j.jconrel.2016.12.011.

Mayer, Lawrence. "Ratiometric dosing of anticancer drug combinations: Controlling drug ratios after systemic administration regulates therapeutic activity in tumor-bearing mice" Mol Cancer Ther 2006;5(7). Jul. 2006 doi:10.1158/1535-7163.MCT-06-0118.

(56) References Cited

OTHER PUBLICATIONS

International Search Report and Written Opinion for PCT/2019/064140 mailed Feb. 20, 2020.

\* cited by examiner cRGD-PEG-PDLA

FA-PEG-PLLA

METHYL-α-GLUCOSE-PEG-PDLA

(a) 
(b) 
(c) 
(d)

STEREOCOMPLEXES FOR THE DELIVERY OF ANTI-CANCER AGENTS

CROSS REFERENCE TO RELATED APPLICATIONS

This application claims priority upon U.S. provisional application Ser. No. 62/775,076 filed on Dec. 4, 2018 and 62/893,863 filed Aug. 30, 2019. These applications are hereby incorporated by reference in their entirety.

BACKGROUND

Delivery of hydrophobic drugs to the appropriate tissues in the body has long been a challenge for medical researchers, who must maximize biocompatibility while minimizing toxicity. An ideal delivery vehicle would avoid premature release of its cargo, thereby delivering a larger dose of the drug to the effective site. Further, it is highly desirable to avoid affecting non-target tissue in order to maximize treatment of the target area as well as to avoid systemic effects. This is of particular concern in cancer research, where many anti-cancer chemotherapeutic agents are hydrophobic and can have toxic side effects. Chemotherapeutic agents, especially those with low molecular weights, can enter all cell types via random diffusion, which both decreases their availability at tumor sites and leads to systemic side effects. Random diffusion may further result in rapid cellular uptake rather than extended therapeutic effect. Finally, filtration by the kidneys can rapidly remove drugs from the bloodstream.

Furthermore, personalized cancer treatment is increasingly becoming possible. Using such an approach, a chemotherapeutic agent or combination of chemotherapeutic agents can be selected to treat a subject's specific tumor(s) more effectively than a general course of chemotherapy. Ideally, the chemotherapeutic agents could be selected based on tests such as biopsies, cell culture, and susceptibility assays rather than conducting expensive genetic tumor profiles.

Further, in some instances, it may be clinically desirable to treat a subject who has cancer with more than one chemotherapeutic agent simultaneously. However, individual chemotherapeutic agents often display toxic side effects and combined side effects of two or more chemotherapeutic agents may prove to be intolerable for subjects.

Currently, polymeric drug conjugates are receiving a great deal of attention for their desirable properties in treating various forms of cancer, including low toxicity and localized delivery. Many polymeric drug conjugates have been successfully tested, but tumor cells often develop resistance to therapy with single drugs. Although combination therapies using polymeric drug conjugates have been developed, most of these have yet to be extensively tested in vivo.

What is needed is a method for treating cancer or reducing tumor size in a subject that minimizes toxicity and is biocompatible, that offers targeted delivery of anti-cancer agents via polymeric drug conjugates or similar means to tumor cells without adversely affecting surrounding tissue, that exhibits controlled, sustained release rates for the anti-cancer agents, and that allows for synergistic combination of two or more anti-cancer agents without a concomitant increase in side effects. Ideally, the method could also be customized for individual patients.

SUMMARY

Disclosed herein are stereocomplexes for the delivery of one or more anti-cancer agents. The stereocomplexes exhibit low toxicity and are biodegradable while also providing for controlled release of one or more anti-cancer agents at tumor sites. The stereocomplexes can be designed such that the anti-cancer agents operate synergistically and may optionally include additional targeting groups and functionalities. The stereocomplexes disclosed herein can be combined with pharmaceutically-acceptable carriers and/or excipients to form pharmaceutical compositions. By varying the amount of each anti-cancer agent in the stereocomplex, specific types of tumors and cancer cell lines can be treated.

The advantages of the materials, methods, and devices described herein will be set forth in part in the description that follows, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 15A shows free DM1 powder (triangles), mPEG-PDLA-SS-DM1 lyophilized powder (circles), and mPEG-PDLA lyophilized powder (squares). FIG. 15B shows mPEG-PLLA-hydrazone-DTX lyophilized powder (squares), mPEG-PDLA-SS-DM1 lyophilized powder (circles), and a complex lyophilized powder formed from previously mentioned two polymers (triangles).

FIG. 16A shows the release of docetaxel over time from the complex at pH 7.4 (squares) and pH 5.5 (circles); this difference is due to the pH sensitivity of the hydrazone linker. FIG. 16B shows the release of DM1 over time from the prodrug D-DM1 formulation and complex at pH 7.4 with and without glutathione (GSH). The complex provides a much slower release than the prodrug with GSH (circles and squares, respectively), while the DM1 conjugation with a redox sensitive disulfide linker prohibits the premature release of DM1 without GSH (complex represented by the inverted triangles, prodrug by the triangles overlapping with the inverted triangles).

FIG. 18A shows tumor size measurements for a control group (squares) and treatment groups (circles). No significant body weight loss was observed for the treatment group or the control group (FIG. 18B). Significant tumor reduction was achieved for the group administered the complex (excised tumors are pictured in FIG. 18C), with a greater total reduction in tumor weight achieved in the stereocomplex treatment group (FIG. 18D).

FIG. 19A shows tumor size change for the group treated with complex (circles) versus the control group (squares). FIG. 19B shows control mice (top row of photos) and treated mice (bottom row of photos) on the 29th day of the trial.

FIG. 21A shows that tumor volume continued to grow for the control group (squares) but was reduced in the complex treatment group (circles). FIG. 21B shows that body weight for the complex treatment group remained approximately the same throughout the trial (circles) but significantly decreased for the control (squares). FIG. 21C shows excised tumors from the control group (top row) and complex group (bottom row) and FIG. 21D shows a comparison of tumor weight between the control group (left bar) and complex group (right bar).

FIG. 22A shows that tumor volume increased significantly more with untreated mice (squares), while mice treated with the complex (circles) exhibited lower final tumor volumes (with arrows indicating injection dates). FIG. 22B shows the change of body weight for the control group and treatment group. FIG. 22C shows excised tumors for the control group (top row) and the stereocomplex treatment group (bottom row). FIG. 22D shows the tumor weight comparison of the control group (left) and stereocomplex treatment group (right).

FIG. 24A shows tumor size change for the group treated with complex (circles) versus the control group (squares). FIG. 24B shows control mice (top row of photos) and treated mice (bottom row of photos) on the 18$^{th}$ day of the trial.

FIG. 25A shows that tumor volume increased significantly more with untreated mice (squares), while mice treated with the complex (circles) exhibited lower final tumor volumes after only one injection (with arrows indicating injection dates). FIG. 25B shows the change of body weight for the control group and treatment group. FIG. 25C shows excised tumors for the control group (top row) and the stereocomplex treatment group (bottom row). FIG. 25D shows the tumor weight comparison of the control group (left) and stereocomplex treatment group (right).

FIG. 26A shows that tumor volume increased significantly more with untreated mice (squares), while mice treated with the complex (circles) exhibited lower final tumor volumes after only one injection. FIG. 26B shows the change of body weight for the control group and the treatment group. FIG. 26C shows excised tumors for the control group (top row) and stereocomplex treatment group (bottom row), notably, one mouse was tumor-free from the 23$^{rd}$ day. FIG. 26D shows the tumor weight comparison of the control group (left) and stereocomplex treatment group (right).

FIG. 28A shows that tumor volume increased significantly more with untreated mice (squares), while mice treated with the complex (circles) exhibited lower final tumor volumes after two injections (with arrows indicating injection dates). FIG. 28B shows the change of body weight for the control group and treatment group. FIG. 28C shows excised tumors for the control group (top row) and stereocomplex treatment group (bottom row), notably, one mouse was tumor-free from the 25th day, and three mice were tumor-free at the end of the test. FIG. 28D shows the tumor weight comparison of the control group (left) and stereocomplex treatment group (right).

FIG. 29A shows that tumor volume increased significantly more with untreated mice (squares), while mice treated with the complex (circles) exhibited lower final tumor volumes after three injections (with arrows indicating injection dates). FIG. 29B shows the change of body weight for the control group and treatment group. FIG. 29C shows excised tumors for the control group (top row) and the stereocomplex treatment group (bottom row). FIG. 29D shows the tumor weight comparison of the control group (left) and stereocomplex treatment group (right).

FIG. 30A shows that tumor volume increased significantly more with untreated mice (squares), while mice treated with the complex (circles) exhibited lower final tumor volumes after three injections (with arrows indicating injection dates). FIG. 30B shows the change of body weight for the control group and treatment group. FIG. 30C shows excised tumors for the control group (top row) and stereocomplex treatment group (bottom row), notably, one mouse was tumor-free from the 27th day. FIG. 30D shows the tumor weight comparison of the control group (left) and the stereocomplex treatment group (right).

FIG. 31A shows that tumor volume increased significantly more with untreated mice (squares), while mice treated with the complex (circles) exhibited lower final tumor volumes after two injections (with arrows indicating injection dates). FIG. 31B shows the change of body weight for the control group and treatment group. FIG. 31C shows excised tumors for the control group (top row) and the stereocomplex treatment group (bottom row). FIG. 31D shows the tumor weight comparison of the control group (left) and stereocomplex treatment group (right).

FIG. 32A shows that tumor volume increased significantly more with untreated mice (squares), while mice treated with the complex (circles) exhibited lower final tumor volumes after three injections (with arrows indicating injection dates). FIG. 32B shows the change of body weight for the control group and treatment group. FIG. 32C shows excised tumors for the control group (top row) and the stereocomplex treatment group (bottom row). FIG. 32D shows the tumor weight comparison of the control group (left) and stereocomplex treatment group (right).

FIG. 33A shows that tumor volume increased significantly more with untreated mice (squares), while mice treated with the complex (circles) exhibited lower final tumor volumes after two injections (with arrows indicating injection dates). FIG. 33B shows the change of body weight for the control group and treatment group. FIG. 33C shows excised tumors for the control group (top row) and stereocomplex treatment group (bottom row), notably, three mice were tumor-free at the end of the test. FIG. 33D shows the tumor weight comparison of the control group (left) and stereocomplex treatment group (right).

FIG. 34A shows that tumor volume increased significantly more with untreated mice (squares), while mice treated with the complex (circles) exhibited lower final tumor volumes after two injections (with arrows indicating injection dates). FIG. 34B shows the change of body weight for the control group and treatment group. FIG. 34C shows excised tumors for the control group (top row) and the stereocomplex treatment group (bottom row). FIG. 34D shows the tumor weight comparison of the control group (left) and stereocomplex treatment group (right).

FIG. 35A shows that tumor volume increased significantly more with untreated mice (squares), while mice treated with the complex (circles) exhibited lower final tumor volumes after only one injection. FIG. 35B shows the change of body weight for the control group and treatment group. FIG. 35C shows excised tumors for the control group (top row) and the stereocomplex treatment group (bottom row). FIG. 35D shows tumor weight comparison of the control group (left) and stereocomplex treatment group (right).

FIG. 36A shows that tumor volume increased significantly more with untreated mice (squares), while mice treated with the complex (circles) exhibited lower final tumor volumes after three injections (with arrows indicating injection dates). FIG. 36B shows the change of body weight for the control group and treatment group. FIG. 36C shows excised tumors for the control group (top row) and the stereocomplex treatment group (bottom row). FIG. 36D shows the tumor weight comparison of the control group (left) and stereocomplex treatment group (right).

FIG. 37A shows tumor size change for the group treated with complex (circles) versus the control group (squares). FIG. 37B shows the photos of the control mice (top row) and the treated mice (bottom row) on the $25^{th}$ day of the trial.

FIG. 42A shows tumor size change for the group treated with complex (circles) versus the control group (squares). FIG. 42B shows the photos of the control mice (top row) and the complex containing glucose treated mice (bottom row) on the 25th day of the trial.

DETAILED DESCRIPTION

Figure 1:
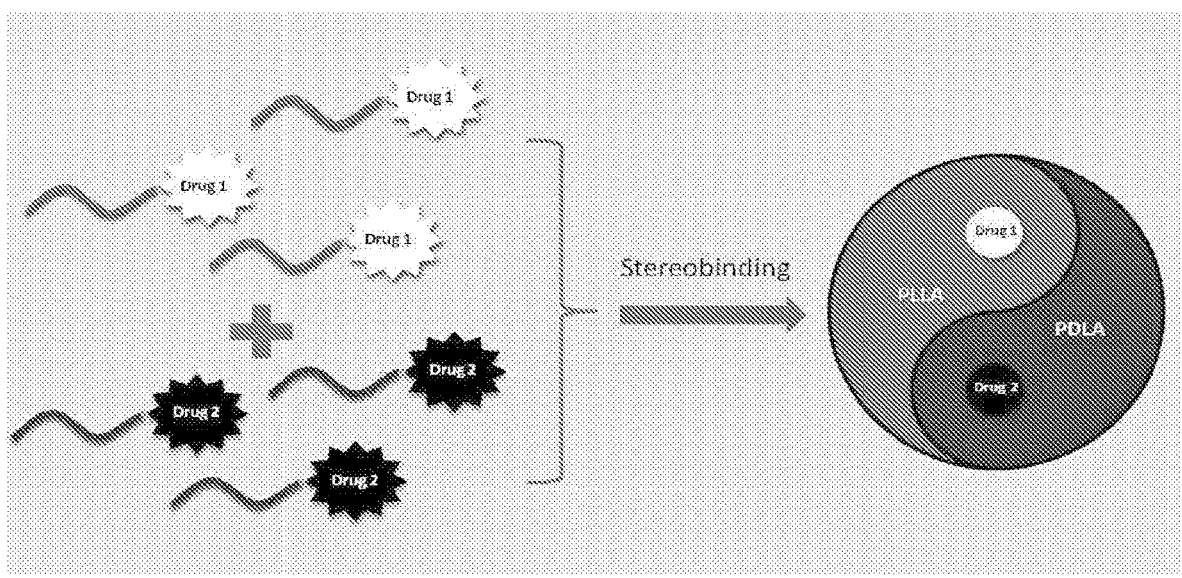
FIG. 1 shows a schematic illustration of the stereocomplexes disclosed herein comprising two different drugs based on the stereocomplexation between PLLA and PDLA.

Before the present materials, articles, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "an anti-cancer agent" includes mixtures of two or more such anti-cancer agents, and the like.

"Optional" or "optionally" means that the subsequently described event or circumstance can or cannot occur, and that the description includes instances where the event or circumstance occurs and instances where it does not. For example, the compositions described herein may optionally contain one or more targeting groups, where the targeting group may or may not be present.

As used herein, the term "about" is used to provide flexibility to a numerical range endpoint by providing that a given value may be "a little above" or "a little below" the endpoint without affecting the desired result. For purposes of the present disclosure, "about" refers to a range extending from 10% below the numerical value to 10% above the numerical value. For example, if the numerical value is 10, "about 10" means between 9 and 11 inclusive of the endpoints 9 and 11.

Throughout this specification, unless the context dictates otherwise, the word "comprise," or variations such as "comprises" or "comprising," will be understood to imply the inclusion of a stated integer or step or group of integers or steps, but not the exclusion of any other integer or step or group of integers or steps. It is also contemplated that the term "comprises" and variations thereof can be replaced with other transitional phrases such as "consisting of" and "consisting essentially of."

"Admixing" or "admixture" refers to a combination of two components together when there is no chemical reaction or physical interaction. The terms "admixing" and "admixture" can also include the chemical interaction or physical interaction among any of the components described herein upon mixing to produce the composition. The components can be admixed alone, in water, in another solvent, or in a combination of solvents.

The term "solid tumor" as defined herein is an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas.

The term "subject" as defined herein is any organism in need of cancer treatment and/or prevention. In one aspect, the subject is a mammal including, but not limited to, humans, domesticated animals (e.g., dogs, cats, horses), livestock (e.g., cows, pigs), and wild animals.

The term "treat" as used herein is defined as maintaining or reducing the symptoms of a pre-existing condition. For example, the compositions described herein are used to treat cancer.

The term "prevent" as used herein is defined as eliminating or reducing the likelihood of occurrence of one or more symptoms of a disease or disorder. For example, the compositions described herein can be used to prevent the regrowth of tumor cells or reduce the rate of regrowth of tumor cells.

The term "inhibit" as used herein is the ability of the compounds described herein to completely eliminate an activity or reduce the activity when compared to the same activity in the absence of the compound. For example, the compositions described herein can be used to inhibit the growth and/or spread of cancer in the body of a subject.

"Biodegradable" materials are capable of being decomposed by bacteria, fungi, or other organisms, or by enzymes in the body of a subject.

"Biocompatible" materials are materials that perform their desired functions without eliciting harmful or deleterious changes to the subject in which they are implanted or to which they are applied, either locally or systemically. In one aspect, the compositions disclosed herein are biocompatible.

As used herein, "toxicity" refers to harmful effects a substance has on an organism such as a human or mammal, or on cells within that organism. A compound or composition with high toxicity would be unsuitable for use as a medical treatment, while a compound or composition with low toxicity would be acceptable for use as a medical treatment. In one aspect, the compounds and compositions disclosed herein exhibit low toxicity.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl, and the like. Examples of longer chain alkyl groups include, but are not limited to, an oleate group or a palmitate group. A "lower alkyl" group is an alkyl group containing from one to six carbon atoms.

The term "aryl group" as used herein is any carbon-based aromatic group including, but not limited to, benzene, naphthalene, etc. The term "aryl group" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group, if substituted, can be substituted with one or more groups including, but not limited to, alkyl, alkynyl, alkenyl, aryl, halide, nitro, amino, ester, ketone, aldehyde, hydroxyl, carboxylic acid, or alkoxy.

The term "alkoxy group" as used herein is defined as RO—, where R is an alkyl group or aryl group defined herein.

The term "halogenated group" is any organic group such as, for example, an alkyl group or aryl group that possesses at least one halogen (F, Cl, Br, I).

References in the specification and concluding claims to parts by weight, of a particular element in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound. A weight percent of a component, unless specifically stated to the contrary, is based on the total weight of the formulation or composition in which the component is included.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an illustration, a numerical range of "about 1 to about 5" should be interpreted to include not only the explicitly recited values of about 1 to about 5, but also to include individual values and sub-ranges within the indicated range. Thus, included in this numerical range are individual values such as 2, 3, and 4, sub-ranges such as from 1-3, from 2-4, from 3-5, etc., as well as 1, 2, 3, 4, and 5, individually. The same principle applies to ranges reciting only one numerical value as a minimum or a maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if an anti-cancer agent is disclosed and discussed and a number of different linkers are discussed, each and every combination of anti-cancer agent and linker that is possible is specifically contemplated unless specifically indicated to the contrary. For example, if a class of molecules A, B, and C are disclosed, as well as a class of molecules D, E, and F, and an example combination of A+D is disclosed, then even if each is not individually recited, each is individually and collectively contemplated. Thus, in this example, each of the combinations A+E, A+F, B+D. B+E, B+F, C+D. C+E, and C+F is specifically contemplated and should be considered from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

Components in the Stereocomplexes

The stereocomplexes described herein are useful in delivering one or more anti-cancer agents to a subject. In one aspect, the stereocomplexes are composed at least two components, each component having a hydrophilic group, an isotactic polylactic acid moiety, a linker, and an anti-cancer agent.

In one aspect, disclosed herein are stereocomplexes having the following components:

$$X^1\text{-}Y^1\text{-}L^1\text{-}Z^1 \qquad (I)$$

$$X^2\text{-}Y^2\text{-}L^2\text{-}Z^2 \qquad (II)$$

wherein $X^1$ and $X^2$ are hydrophilic groups; $Y^1$ and $Y^2$ are PDLA or PLLA; $L^1$ and $L^2$ are cleavable linkers, $Z^1$ is an anti-cancer agent, $Z^2$ is an anti-cancer agent or imaging agent, wherein when $Z^2$ is an anti-cancer agent, $Z^1$ and $Z^2$ are different anti-cancer agents, and wherein (1) when $Y^1$ is PDLA then $Y^2$ is PLLA, and when $Y^1$ is PLLA then $Y^2$ is PDLA and (2) the ratio of the total number of D-lactic acid units in the stereocomplex to the total number of L-lactic acid units in the stereocomplex is from 0.9:1.1 to 1.1:0.9.

Not wishing to be bound by theory, stereocomplexes form when the PDLA and PLLA units present in components (I) and (II) form an extensive 3-dimensional network driven by hydrogen bonding. The stereocomplexes described herein have enhanced properties such as tensile strength, Young's modulus, and elongation at break compared to either component (I) or component (II) alone. The stereocomplexes have high stability and high resistance to hydrolytic degradation, which eliminates the premature release of drugs (i.e., before the stereocomplexes reach their target tissue) and increases the circulation time of the stereocomplexes in the blood.

Figures 2A, 2B:
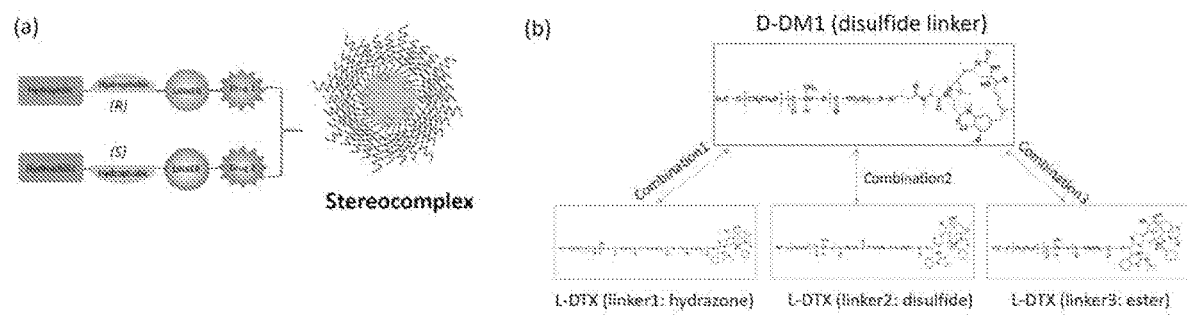
FIG. 2 shows a schematic illustration of polymer conjugated drugs (PCD) for stereocomplexation. In panel (a), hydrophilic elements project into solution and hydrophobic elements are located at the particle core of the stereocomplexes. In panel (b), examples of anti-cancer drugs conjugated with hydrophobic parts with cleavable linkers are shown. In one example form, mertansine (DM1) is conjugated using a disulfide bond while docetaxel (DTX) is conjugated using a hydrazone bond (linker 1), a disulfide bond (linker 2), or an ester bond (linker 3).

FIG. 1 shows a schematic illustration of an exemplary stereocomplex with two different drugs based on the stereocomplexation between PDLA and PLLA. FIG. 2 shows a schematic illustration of exemplary polymer conjugated drugs for stereocomplexation. Without wishing to be bound by theory, hydrophilic elements project into solution while hydrophobic elements cluster at the particle core (FIG. 2A). Examples anti-cancer drugs conjugated to hydrophobic parts with cleavable linkers are provided in FIG. 2B. Referring to FIG. 2B, mertansine (DM1) is linked to a carrier with a disulfide bond (D-DM1) and docetaxel (DTX) is linked to a carrier with a hydrazone bond, ester bond, or disulfide bond (L-DTX).

Each component used to prepare the stereocomplexes and methods for making and using thereof are described in detail herein.

a. Hydrophilic Group

The components used to produce the stereocomplexes disclosed herein include a hydrophilic group. In one aspect, $X^1$ and $X^2$ in components (I) and (II) are different hydrophilic groups. In an alternative aspect, $X^1$ and $X^2$ are the same hydrophilic group. In still another aspect, $X^1$ and $X^2$ are each a polyalkylene glycol.

"Polyalkylene glycol" as used herein refers to a condensation polymer of ethylene oxide or propylene oxide and water. Polyalkylene glycols are typically colorless liquids with high molecular weights and are soluble in water as well as some organic solvents. In one aspect, the hydrophilic group in the stereocomplexes disclosed herein is a polyalkylene glycol. In another aspect, the polyalkylene glycol is polyethylene glycol and/or polypropylene glycol. In another aspect, the polyalkylene glycol is monomethoxy polyethylene glycol. The generic structure of a polyalkylene glycol is as follows:

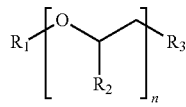

Substitutions in selected polyalkylene glycols are provided in Table 1:

TABLE 1

| Polyalkylene Glycols | | | |
|---|---|---|---|
| Compound Name | $R_1$ | $R_2$ | $R_3$ |
| Polyethylene glycol | H | H | OH |
| Polypropylene glycol | H | $CH_3$ | OH |
| Monomethoxy polyethylene glycol | $CH_3$ | H | OH |

In a further aspect, polyalkylene glycols are of low enough molecular weight that the chemical nature of the end groups (usually, but not always, hydroxyls) still affects the performance of the polymers. In addition to being hydrophilic, polyalkylene glycols can modify the viscosity of the stereocomplexes disclosed herein and may aid in the formation of emulsions. In another aspect, polyalkylene glycols are biocompatible and/or biodegradable. In still another aspect, the polyalkylene glycols and/or other hydrophilic groups used herein are non-toxic.

In one aspect, when $X^1$ and $X^2$ in components (I) and (II) are polyalkylene glycols, $X^1$ and $X^2$ have molecular weights of from about 1,000 Da to about 5,000 Da, or from 1,500 Da to 4,500 Da, or from 2,000 Da to 4,000 Da, or have molecular weights of about 1,000 Da, 1,500 Da, 2,000 Da, 2,500 Da, 3,000 Da, 3,500 Da, 4,000 Da, 4,500 Da, or about 5,000 Da, where any value can be a lower and upper end-point of a range (e.g., 2,000 Da to 4,000 Da).

In another aspect, $X^1$ and $X^2$ in components (I) and (II) of the stereocomplexes disclosed herein are each monomethoxy polyethylene glycol having molecular weights of from about 1,000 to about 5,000 Da, or from 1,500 Da to 4,500 Da, or from 2,000 Da to 4,000 Da, or have molecular weights of about 1,000 Da, 1,500 Da, 2,000 Da, 2,500 Da, 3,000 Da, 3,500 Da, 4,000 Da, 4,500 Da, or about 5,000 Da, where any value can be a lower and upper end-point of a range (e.g., 2,000 Da to 4,000 Da). In one aspect, $X^1$ and $X^2$ in components (I) and (II) of the stereocomplexes disclosed herein are each monomethoxy polyethylene glycol having the same molecular weight.

b. PDLA/PLLA

Polylactic acid is a polyester derived from lactic acid. The polyester is composed of lactic acid units depicted in the structure below, where m indicates the number of lactic acid units. The lactic acid unit has one chiral center, indicated by the asterisk (*) in the structure below, where m is the number of lactic acid units:

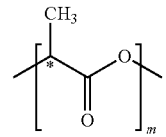

Polylactic acid polymerization can begin from D or L lactic acid or a mixture thereof, or lactide, a cyclic diester. Properties of polylactic acid can be fine-tuned by controlling the ratio of D to L enantiomers used in the polymerization, and polylactic acid polymers can also be synthesized using starting materials that are only D or only L rather than a mixture of the two. Polylactic acid prepared from only D starting materials is referred to as poly-D-lactide (PDLA) (i.e., only composed of D-lactic acid units); conversely, polylactic acid prepared from only L starting materials is poly-L-lactide (or PLLA) (i.e., only composed of L-lactic acid units).

As used herein, a D-lactic acid unit or an L-lactic acid unit refers to the monomer units within the polylactic acid polymers described herein, wherein a D-lactic acid unit is derived from the D-lactic acid or D-lactide starting material, and an L-lactic acid unit is derived from the L-lactic acid or L-lactide starting material, as shown in Table 2:

TABLE 2

Starting Materials for PDLA and PLLA

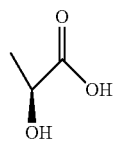

L-lactic acid

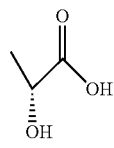

D-lactic acid

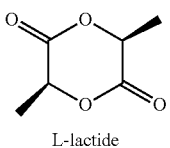

L-lactide

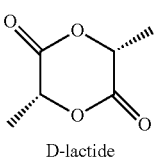

D-lactide

The polylactic acid in components (I) and (II) is represented by $Y^1$ and $Y^2$ where when $Y^1$ is PDLA then $Y^2$ is PLLA or, in the alternative, when $Y^1$ is PLLA then $Y^2$ is PDLA.

In one aspect, the ratio of the total number of D-lactic acid units in the stereocomplex to the number of L-lactic acid units in the stereocomplex is from 0.9:1.1 to 1.1:0.9. In another aspect, the ratio of the total number of D-lactic acid units to the number of L-lactic acid units is 0.9:1.1, 0.95:1.05, 1:1, 1.05:0.95, or 1.1:0.9. In one aspect, the ratio of the total number of D-lactic acid units to the number of L-lactic acid units approaches 1:1. Put another way, in some aspects, the total number of D-lactic acid units and L-lactic acid units in the stereocomplexes are approximately equal.

PDLA and PLLA are present in components (I) and (II); however, as will be discussed in greater detail below, additional components can be used to prepare the stereocomplexes herein that include PDLA or PLLA. These components add to the total number of D-lactic acid units or L-lactic acid units present in the stereocomplex.

In one aspect, PDLA and PLLA present in components (I) and (II) has a molecular weight of from about 700 Da to about 5,000 Da, or about 750 Da to 4000 Da, or about 1,000 Da to about 3,000 Da. Further in this aspect, PDLA and PLLA has a molecular weight of about 700 Da, 750 Da, 800 Da, 900 Da, 1,000 Da, 1,250 Da, 1,500 Da, 2,000 Da, 2,500 Da, 3,000 Da, 3,500 Da, 4,000 Da, 4,500 Da, or 5,000 Da, where any value can be a lower and upper end-point of a range (e.g., 1,000 Da to 3,000 Da). In another aspect, PDLA and PLLA present in components (I) and (II) have equal molecular weights or approximately equal molecular weights.

In another aspect, the number of D-lactic acid units present in PDLA and L-lactic acid units present in PLLA in components (I) and (II) is from 10, 15, 20, 25, 30, 35, 40, 45, 50, 55, 60, 65, 70, 75, 80, 85, 90, 95, or 100, where any value can be a lower and upper end-point of a range (e.g., 10 to 60). In another aspect, PDLA and PLLA present in components (I) and (II) have the same number of D-lactic acid units and L-lactic acid units, respectively.

The hydrophilic group in components (I) and (II) is covalently bonded to PDLA or PLLA. In one aspect, when the hydrophilic group is monomethoxy polyethylene glycol, the terminal hydroxyl group can react with the terminal carboxyl group of PDLA or PLLA to form a new ester. Exemplary methods for bonding the hydrophilic group to PDLA or PLLA are provided in the Examples.

c. Cleavable Linker

In one aspect, the stereocomplexes disclosed herein include a cleavable linker. The cleavable linker includes at least one cleavable group so that upon cleavage the anti-cancer-agent is released. Cleavage of the cleavable group can occur by, for example, enzymatically, hydrolytically, or with a change in pH.

In one aspect, $L^1$ and $L^2$ present in components (I) and (I) are different cleavable linkers. Further in this aspect, $L^1$ and $L^2$ can exhibit different cleavage rates (e.g., hydrolytic, enzymatic, pH) due to the presence of different cleavable groups and can thus release their linked anti-cancer agents at different, controlled rates. In one aspect, the selection of the cleavable linker and rate of hydrolytic degradation of the linker can reduce the required concentration of the anti-cancer agents or can enhance the synergistic effects of the anti-cancer agents present in the stereocomplex. Thus, $L^1$ and $L^2$ can be selected to achieve a sequential or concomitant release of two different anti-cancer agents. In an alternative aspect, $L^1$ and $L^2$ are the same cleavable linker.

In one aspect, $L^1$ and $L^2$ independently includes a cleavable group including, but not limited to, a disulfide group, an ester group, a hydrazone group, an acetal group, an imine group, a β-thiopropionate group, an amide group, or any combination thereof. The cleavable linker molecule can include one or more of these groups. The cleavable linker can also include additional functional groups so that the cleavable linker can be covalently bonded to PDLA or PLLA. In one aspect, the cleavable linker includes a functional group that can react with a terminal hydroxyl group of PDLA or PLLA to produce a new covalent bond. For example, the cleavable linker can include a carboxyl group (e.g., carboxylic acid, ester, anhydride) that reacts with the hydroxyl group of PDLA or PLLA. Exemplary methods for bonding the cleavable linker to PDLA or PLLA are provided in the Examples and figures herein.

Disulfide Group

As used herein, a disulfide group is a functional group with the structure (—S—S—). Upon cleavage of the disulfide group, the anti-cancer agent is released. In one aspect, $L^1$ or $L^2$ or both $L^1$ and $L^2$ of the stereocomplexes disclosed herein include a disulfide group. Not wishing to be bind by theory, disulfide groups are glutathione redox sensitive. Glutathione (GSH) in cancer cells is implicated in the regulation of carcinogenic mechanisms; sensitivity against cytotoxic drugs, ionizing radiations, and some cytokines; DNA synthesis; and cell proliferation and death. GSH can cleave disulfide bonds in order to release the anti-cancer agent present in the stereocomplex to produce the corresponding thiol. Representative linkers with a disulfide group are provided herein.

Ester Group

As used herein, an ester group is a functional group with the following structure

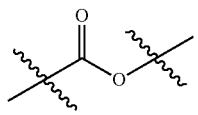 [SMILES: *OC(*)=O]

In one aspect, $L^1$ or $L^2$ or both $L^1$ and $L^2$ of the stereocomplexes disclosed herein include an ester group. Upon cleavage of the ester group, the anti-cancer agent is released. Exemplary methods for preparing and using a cleavable linker with an ester group are provided in the Examples and figures herein.

Hydrazone Group

As used herein, a hydrazone group is a functional group with the following structure, where R and R' can be the same or different:

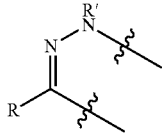

In one aspect, $L^1$ or $L^2$ or both $L^1$ and $L^2$ of the stereocomplexes disclosed herein include a hydrazone group. Upon cleavage of the hydrazone group, the anti-cancer agent is released. Exemplary methods for preparing and using a cleavable linker with a hydrazone group are provided in the Examples and figures herein.

Acetal Group

As used herein, an acetal group is a functional group with the following structure, where R, R', and R" can be the same or different:

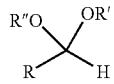

In one aspect, $L^1$ or $L^2$ or both $L^1$ and $L^2$ of the stereocomplexes disclosed herein include an acetal group. Upon cleavage of the acetal group, the anti-cancer agent is released.

Imine Group

As used herein, an imine group is a functional group with the following structure:

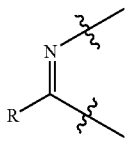

In one aspect, $L^1$ or $L^2$ or both $L^1$ and $L^2$ of the stereocomplexes disclosed herein include an imine group. Upon cleavage of the imine group, the anti-cancer agent is released.

β-thiopropionate Group

As used herein, a β-thiopropionate group is a functional group with the following structure, where R and R' can be the same or different:

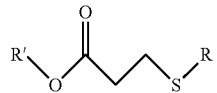

In one aspect, $L^1$ or $L^2$ or both $L^1$ and $L^2$ of the stereocomplexes disclosed herein include a β-thiopropionate group. Upon cleavage of the β-thiopropionate group, the anti-cancer agent is released.

Amide Group

As used herein, an amide group is a functional group with the following structure:

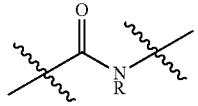

In one aspect, $L^1$ or $L^2$ or both $L^1$ and $L^2$ of the stereocomplexes disclosed herein include an amide group. Upon cleavage of the amide group, the anti-cancer agent is released d. Anti-Cancer Agent In one aspect, the stereocomplexes described herein include two or more anti-cancer agents. As used herein, an "anti-cancer agent" is a compound used to kill cancer cells in the body of a subject, to slow the growth of cancer in a subject, to keep cancer from spreading in a subject, or to prevent the return of a tumor that has been surgically removed. Anti-cancer agents may operate by a variety of methods including, but not limited to, by alkylating DNA (which can interfere with coiling and recognition by DNA replication enzymes), by interfering with the production of DNA, by interfering with the production of proteins in cancer cells, by preventing cancer cells from dividing, or by slowing the growth of a cancer that depends on hormones. The anti-cancer agent is covalently bonded to the cleavable linker.

The relative amount of each anti-cancer agents present in the stereocomplex can be varied to achieve additive and/or synergistic therapeutic effects with specific types of cancer. This feature of the stereocomplexes is described in greater detail below.

In one aspect, the anti-cancer agent is paclitaxel, doxorubicin, gemcitabine, cisplatin, methotrexate, 5-fluorouricil, betulinic acid, amphotericin B, diazepam, nystatin, propofol, testosterone, docetaxel, a maytansinoid, a PD-1 inhibitor, a PD-L1 inhibitor, a protein kinase inhibitor, a P-glycoprotein inhibitor, an autophage inhibitor, a PARP inhibitor, an aromatase inhibitor, a monoclonal antibody, a photosensitizer, a radiosensitizer, an interleukin, an antiandrogen, or any combination thereof. In one aspect, when the anti-cancer agent is a maytansinoid, it can be ansamitocin, mertansine (DM1), ravtansine, or another maytansinoid. In a further aspect, an anti-cancer agent can fall into multiple of the above categories at the same time. For example, an aromatase inhibitor can also be an antiandrogen, or a PD-1 inhibitor can also be a monoclonal antibody.

In one aspect, the anti-cancer agent is a PD-1 inhibitor or a PD-L1 inhibitor. PD-1 inhibitors and PD-L1 inhibitors are immune checkpoint inhibitors that inhibit the association of programmed death-ligand 1 (PD-L1) with programmed cell death protein 1 (PD-1). This protein-ligand interaction is involved in the suppression of the immune system in certain types of cancer. In one aspect, the compositions disclosed herein include PD-1 and/or PD-L1 inhibitors. In a further aspect, the PD-1 inhibitor can be pembrolizumab, nivolumab, pidilizumab, AMP-224, AMP-514, or PDR001. In a still further aspect, the PD-L1 inhibitor can be atezolizumab, avelumab, durvalumab, or BMS0936559. Without wishing to be bound by theory, when PD-L1 on a cancer cell interacts with PD-1 on a T-cell, T-cell function signals are reduced, thereby preventing the immune system from attacking the tumor cell. Thus, blocking of this interaction allows the immune system to target the tumor cell. In one aspect, advanced melanoma, non-small cell lung cancer, renal cell carcinoma, bladder, cancer, Hodgkin's lymphoma, and other cancers can be treated by PD-1 and PD-L1 inhibitors.

In one aspect, the anti-cancer agent is a monoclonal antibody. In monoclonal antibody therapy, monoclonal antibodies bind monospecifically to target cells and/or proteins, stimulating a subject's immune system to attack those cells. In some aspects, monoclonal antibody therapy is used in conjunction with radiotherapy. In one aspect, the compositions disclosed herein include monoclonal antibodies. Monoclonal antibodies may be murine (suffix -omab), chimeric (suffix -ximab), humanized (suffix -zumab), or human (suffix -umab). In one aspect, the monoclonal antibody is ramucirumab, 3F8, 8H9, Abagovomab, Abituzumab, Adalimumab, Afutuzumab, Alacizumab pegol, Amatuximab, Anatumomab mafenatox, Andecaliximab, Anetumab ravtansine, Apolizumab, Arcitumomab, Ascrinvacumab, Atezolizumab, Avelumab, Azintuxizumab vedotin, Bavituximab, BCD-100, Belantamab mafodotin, Belimumab, Bemarituzumab, Besilesomab, Bevacizumab, Bivatuzumab mertansine, Brentuximab vedotin, Brontictuzumab, Cabiralizumab, Camidanlumab tesirine, Camrelizumab, Cantuzumab mertansine, Cantuzumab ravtansine, Carotuximab, Cantumaxomab, cBR96-doxorubicin immunoconjugate, Cemiplimab, Cergutuzumab amunaleukin, Cetrelimab, Cetuximab, Cibisatamab, Citatuzumab bogatox, Cixutumumab, Clivatuzumab tetraxetan, Codrituzumab, Cofetuzumab pelidotin, Coltuximab ravtansine, Conatumumab, Cusatuzumab, Dacetuzumab, Dalotuzumab, Daratumumab, Demcizumab, Denintuzumab mafodotin, Depatuxizumab mafodotin, Derlotuximab biotin, Detumomab, Dinutuximab, Drozitumab, DS-8201, Duligotuzumab, Durvalumab, Dusitgitumab, Duvortuxizumab, Ecromeximab, Edrecolomab, Elgemtumab, Elotuzumab, Emactuzumab, Emibetuzumab, Enapotomab vedotin, Enavatuzumab, Enfortumab vedotin, Enoblituzumab, Ensituximab, Epratuzumab, Ertumaxomab, Etaracizumab, Faricimab, Farletuzumab, FBTA05, Ficlatuzumab, Figitumumab, Flanvotumab, Flotetuzumab, Futuximab, Galiximab, Gancotamab, Ganitumab. Gatipotozumab, Gemtuzumab ozogamicin, Girentuximab, Glembatumumab vedotin, IBI308, Ibritumomab tiuxetan, Icrucumab, Iladatuzumab vedotin, IMAB362, Imalumab, Imgatuzumab, Indatuximab ravtansine, Indusatumab vedotin, INebilizumab, INtetumumab, Ipilimumab, Iratumumab, Isatuximab, Istiratumab, Labetuzumab, Lacnotuzumab, Ladiratuzumab vedotin, Lenzilumab, Lexatumumab, Lifastuzumab vedotin, Loncastuximab tesirine, Losatuxizumab vedotin, Lilotomab satetraxetan, Lintuzumab, Lirilumab, Lorvotuzumab mertansine, Lucatumumab, Lumiliximab, Lumretuzumab, MABp1, Mapatumumab, Margetuximab, Matuzumab, Milatuzumab, Mirvetuximab soravtansine, Mitumomab, Modotuximab, Mogamulizumab, Monalizumab, Mosunetuzumab, Moxetumomab pasudotox, Nacolomab tafenatox, Naptumomab estafenatox, Narnatumab, Navicixizumab, Naxitamab, Necitumumab, Nesvacumab, Nimotuzumab, Nivolumab, Nofetumomab merpentan, Obinutuzumab, Ocaratuzumab, Ofatumumab, Olaratumab, Oleclumab, Onartuzumab, Ontuxizumab, Oportuzumab monatox, ORegovomab, Otlertuzumab, Pamrevlumab, Panitumumab, Pankomab, Parsatuzumab, Pasotuxizumab, Patritumab, PDR001, Pembrolizumab, Pemtumomab, Pertuzumab, Pidilizumab, Pinatuzumab vedotin, Polatuzumab vedotin, Pritumumab, Racotumomab, Radretumab, Ramucirumab, Rilotumumab, Rituxiamab, Robatumumab, Rosmantuzumab, Rovalpituzumab tesirine, Sacituzumab govitecan, Samalizumab, Samrotamab vedotin, Seribantumab, Sibrotuzumab, SGN-CD19A, Siltuximab, Sirtratumab vedotin, Sofituzumab vedotin, Solitomab, Spartalizumab, Tabalumab, Tacatuzumab tetraextan, Tapitumumab paptox, Tarextumab, Tavolimab, Telisotuzumab vedotin, Tenatumomab, Tepotidimab, Tetulomab, TGN1412, Tigatuzumab, Timigutuzumab, Tiragotumab, Tislezlizumab, Tisotumab vedotin, TNX-650, Tomuzutuximab, Tovetumab, Trastuzumab, Trastuzumab emtansine, TRBS07, Tremelimumab, Tucotuzumab celmoleukin, Ublituximab, Ulocuplumab, URelumab, Utomilumab, Vadastuximab talirine, Vandortuzumab vedotin, Vantictumab, Vanucizumab, Varisacumab, Varlilumab, Veltuzumab, Vesencumab, Volociximab, Vonlerolizumab, Vorsetuzumab mafodotin, Votumumab, XMAB-5574, Zalutumumab, Zatuximab, Zenocutuzumab, Zolbetuximab, or tositumomab. In another aspect, monoclonal antibodies can be used to treat advanced malignancies and lymphomas such as non-Hodgkins lymphoma as well as neuroblastoma, sarcoma, metastatic brain cancers, ovarian cancer, prostate cancer, breast cancers including triple-negative breast cancer, lymphoma, non-small cell lung carcinoma, gastric cancer, gastroesophageal junction adenocarcinoma, hematological cancers, melanoma, squamous cell carcinoma, Hodgkin's lymphoma, anaplastic large-cell lymphoma, pancreatic cancer, acute lymphoblastic leukemia, acute myeloid leukemia, hepatocellular carcinoma, colorectal cancer, angiosarcoma, head and neck cancer, ovarian cancer, solid tumors, multiple myeloma, glioblastoma, testicular cancer, B-cell malignancies, urotnelial cancer, chronic lymphocytic leukemia, adenocortical carcinoma, acute myelogenous leukemia, clear cell renal cell carcinoma, chronic myelomonocytic leukemia, juvenile myelomonocytic leukemia, small cell lung carcinoma, hairy cell leukemia, renal cell carcinoma, nasopharyngeal cancer, glioma, chronic lymphatic leukemia, diffuse large B-cell lymphoma, and other cancers.

In one aspect, the anti-cancer agent is a photosensitizer. Photosensitizers are used in conjunction with light and molecular oxygen to elicit cell death. In one aspect, the compositions disclosed herein include photosensitizers. Without wishing to be bound by theory, first a photosensitizer is administered in the absence of light until the photosensitizer reaches a critical concentration in the tissue to be treated. Following this, the photosensitizer is activated by exposure to light at a level sufficient to activate the photosensitizer while minimizing damage to nearby healthy tissue. In a further aspect, malignant cancers of the head and neck, lung, bladder, and skin (including Kaposi's sarcoma and cutaneous non-melanoma skin cancer), metastatic breast cancer, cancers of the gastrointestinal tract, and bladder cancer may be particularly susceptible to photosensitizers. In one aspect, the photosensitizer can be a porphyrin, a chlorine, or a dye. In another aspect, the photosensitizer is 5-aminolevulinic acid (Levulan), silicon phthalocyanine Pc 4, naphthalocyanines, metallo-naphthalocyanines, tin (IV) purpurins, copper octaethylbenzochlorin, zinc (II) purpurins, m-tetrahydroxyphenylchlorin, mono-L-aspartyl chlorine e6, Allumera, Photofrin, Visudyne (Verteporfin), Foscan, Metvix, Hexvix, Cysview, Laserphyrin, Antrin, Photochlor, Photosens, Photrex, Purlytin, Lutex, Lumacan, Cevira, Visonac, BF-200 ALA, Amphinez, azadipyrromethenes, zinc phthalocyanine, or another photosensitizer.

In one aspect, the anti-cancer agent is a protein kinase inhibitor. Protein kinase inhibitors block the action of one or more protein kinases. Protein kinases may be overexpressed in certain types of cancer. In some aspects, the compositions disclosed herein include one or more protein kinase inhibitors. In a further aspect, the protein kinase inhibitor can be afatanib, axitinib, bosutinib, cetuximab, cobimetinib, crizotinib, cabozanitinib, dasatinib, entrectinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, vemurafenib, or another protein kinase inhibitor. In some aspects, protein kinase inhibitors are particularly useful against non-small cell lung cancer, renal cell carcinoma, chronic myoleginous leukemia, advanced melanoma, metastatic medullary thyroid cancer, neruoblastoma, colorectal cancer, breast cancer, thyroid cancer, renal cancer, myelofibrosis, renal cell carcinoma, or gastrointestinal stromal tumors.

In one aspect, the anti-cancer agent can be a p-glycoprotein inhibitor. P-glycoproteins are promiscuous drug efflux pumps and can reduce bioavailability of drugs at tumor sites. Not wishing to be bound by theory, p-glycoprotein inhibitors can enhance the intracellular accumulation of anti-cancer agents. In one aspect, this can be accomplished by binding to p-glycoprotein transporters, inhibiting transmembrane transport of anti-cancer agents. Inhibition of transmembrane transport may result in increased intracellular concentrations of anti-cancer agent, which ultimately can enhance its cytotoxicity. In a further aspect, the p-glycoprotein inhibitor is verapamil, cyclosporine, tamoxifen, a calmodulin antagonist, dexverapamil, dexniguldipine, valspodar (PSC 833), biricodar (VX-710), tariquidar (XR9576), zosuquidar (LY335979). Ianiquidar (R101933), elacridar (GF120918), timcodar (VX-853), taxifolin, naringenin, diosmin, quercetin, diltiazem, bepridil, nicardipine, nifedipine, felodipine, isradipine, trifluoperazine, clopenthixol, trifluopromazine, flupenthixol, emopamil, gallopamil, Ro11-2933, amiodarone, clarithromycin, colchicines, erythromycin, lansoprazole, omeprazole, another proton-pump inhibitor, paroxetine, sertraline, quinidine, or any combination thereof. In one aspect, p-glycoprotein inhibitors are particularly effective at treating drug-resistant cancers, including as part of a combination therapy.

In one aspect, the anti-cancer agent is an autophagy inhibitor. Autophagy, as used herein, is a mechanism of intracellular degradation dependent upon lysosomes. Autophagy involves multiple proteins, including some protein kinases. Autophagy inhibitors can target early stages of autophagy (i.e., pathways involved in initial steps of the core autophagy machinery) or can target later stages (i.e., the functions of lysosomes). In one aspect, the compositions disclosed herein include one or more autophagy inhibitors. In a further aspect, the autophagy inhibitor can be 3-methyladenine, wortmannin, LY294002, PT210, GSK-2126548, spautin-1, SAR405, compound 31, VPS34-IN1, PIK-III, compound 6, MRT68921, SBI-0206965, pepstatin A, E64d, bafilomycin A1, clomipramine, lucanthone, chloroquine, hydroxychloroquine, Lys05, ARN5187, compound 30, or another autophagy inhibitor. In a further aspect, autophagy inhibitors may be useful for treating non-small cell lung cancer, chronic myeloid leukemia, metastatic prostate cancer, castrate refractory prostate cancer, metastatic colorectal cancer, breast cancer, brain metastases, relapsed and refractory multiple myeloma, glioblastoma multiform, and other cancers.

In one aspect, the anti-cancer agent is a radiosensitizer. Radiosensitizers make tumor cells more sensitive to radiation therapy. In one aspect, the compositions disclosed herein include one or more radiosensitizers. In one aspect, the radiosensitizer is a fluoropyrimidine, gemcitabine, a platinum analog such as cisplatin, NBTXR3, Nimoral, trans sodium crocetinate, NVX-108, misonidazole, metronidazole, tirapazamine, or another radiosensitizer. Without wishing to be bound by theory, radiosensitizers interfere with the regulation of cell cycle checkpoints in tumor cells, especially those with DNA damage caused by radiation therapy. Some radiosensitizers may crosslink DNA strands, exacerbating DNA damage caused by radiation therapy. In one aspect, radiosensitizers may be particularly useful for soft tissue sarcoma of the extremities and trunk wall, hepatocellular carcinoma, prostate cancer, squamous cell cancer of the oral cavity, squamous cell carcinoma of the head and neck, and glioblastoma.

In one aspect, the anti-cancer agent is a PARP inhibitor. PARP inhibitors act against the enzyme poly ADP ribose polymerase. In one aspect, the compositions disclosed herein include one or more PARP inhibitors. Without wishing to be bound by theory, PARP inhibitors block PARP activity, preventing the repair of DNA damage, and may also localize PARP proteins at sites of DNA damage, which blocks DNA replication and is thus cytotoxic. In one aspect, PARP inhibitors are effective against recurrent platinum-sensitive ovarian cancer, tumors with BRCA1, BRCA2, or PALB2 mutations, PTEN-defective tumors (e.g., certain prostate cancers), fast-growing tumors that are low in oxygen, epithelial ovarian cancer, fallopian tube cancer, primary peritoneal cancer, squamous cell lung cancer, hematological malignancies, advanced or recurrent solid tumors, non-small cell lung cancer, triple-negative breast cancer, colorectal cancer, metastatic breast and ovarian cancer, and metastatic melanoma. In one aspect, the PARP inhibitor is MK-4827 (also known as niraparib), rucaparib, iniparib, talazoparib, olaparib, veliparib, CEP 9722, E7016, BGB2-290, 3-aminobenzamide, or another PARP inhibitor.

In one aspect, the anti-cancer agent is an interleukin. Interleukins are cytokines, or signal molecules, typically expressed by white blood cells. In some aspects, externally synthesized interleukins can be used as cancer treatments. In one aspect, the compositions disclosed herein include one or more interleukins. In a further aspect, the interleukin can be PROLEUKIN® (also known as IL-2 and aldesleukin) or another interleukin. Without wishing to be bound by theory, interleukins may aid in encouraging the growth of killer T cells and other immune cells, thereby enhancing the function of a subject's immune system as it relates to emerging tumor cells. In another aspect, interleukins may be effective against kidney cancers and melanoma.

In one aspect, the anti-cancer agent is a mTOR inhibitor. mTOR inhibitors are drugs that inhibit the mechanistic target of rapamycin. mTOR is a serine/threonine-specific protein kinase and is important for regulation of metabolism, growth, and cell proliferation. In one aspect, the compositions disclosed herein include one or more mTOR inhibitors. In a further aspect, the mTOR inhibitor can be rapamycin, sirolimus, temsirolimus, everolimus, ridaforolimus, deforolimus, dactolisib, sapanisertib, AZD8055, AZD2014, or another mTOR inhibitor. Without wishing to be bound by theory, mTOR inhibitors act against T-cell proliferation and proliferative responses induced by various cytokines, including processes related to tumor angiogenesis. In one aspect, certain mTOR inhibitors may be primarily effective against tumors with specific genetic determinants or mutations. mTOR inhibitors may be particularly useful against renal cell carcinoma, subependymal giant cell astrocytoma, progressive neuroendocrine tumors of pancreatic origin, or advanced breast cancer. In another aspect, mTOR inhibitors can be used as monotherapy for disease stabilization or as part of combination therapy for many cancer types.

In one aspect, the anti-cancer agent is an aromatase inhibitor. Aromatase inhibitors are useful in the treatment and prevention of breast and ovarian cancers, especially in postmenopausal women, high-risk women, and women with hormone-sensitive tumors. In one aspect, the compositions disclosed herein include one or more aromatase inhibitors. Without wishing to be bound by theory, aromatase inhibitors block the conversion of various precursors, including androstenedione and testosterone. In one aspect, the aromatase inhibitor is an irreversible steroidal inhibitor, which can act by forming a permanent bond with the aromatase enzyme. In another aspect, the aromatase inhibitor is a nonsteroidal inhibitor, which reversibly competes with substrates for the aromatase enzyme. In still another aspect, the specific mechanism of action of the aromatase inhibitor may be unknown. In one aspect, the aromatase inhibitor can be aminoglutethimide, testolactone, anastrozole, letrozole, exemestane, vorozole, formestane, fadrozole, 1,4,6-androstatrien-3,17-dione, 4-androstene,3,6,17-trione, or another aromatase inhibitor.

In one aspect, the anti-cancer agent is an antiandrogen. Antiandrogens, or androgen synthesis inhibitors, prevent the biosynthesis of androgen hormones. In one aspect, the compositions disclosed herein include one or more antiandrogens. Without wishing to be bound by theory, antiandrogens can act at a variety of different steps in the androgen synthesis pathway including, but not limited to, inhibiting the conversion of cholesterol into a steroid hormone precursor, or inhibiting the conversion of pregnane steroids into androgens. In one aspect, the antiandrogen can be aminoglutethimide (which also acts as an aromatase inhibitor), ketoconazole, abiraterone acetate, seviteronel, or another antiandrogen.

e. Imaging Agent

The stereocomplexes disclosed herein may include one or more imaging agents. As used herein, "imaging agent" refers to a compound or composition that enhances contrast, visibility, or another property during a medical imaging procedure such as, for example, an X-ray, computed tomography and single photon emission computed tomography, an ultrasound, an MRI (magnetic resonance imaging), a nuclear medical procedure (including positron emission tomography and related techniques), optical imaging, near infrared imaging, angiography, venography, endoscopy, voiding cystourethrogaphy, hysterosalpingogram, intravenous urography, or another medical imaging procedure. Imaging agents are generally non-toxic and stable in vivo. Ideal imaging agents should rapidly clear from the bloodstream and bind to and accumulate in specific target tissues.

In one aspect, $Z^2$ in component (II) is an imaging agent, where the imaging agent is covalently bonded to component (II). In another aspect, the stereocomplex is composed of the following components:

$X^1\text{-}Y^1\text{-}L^1\text{-}Z^1$ (I)

$X^2\text{-}Y^2\text{-}L^2\text{-}Z^2$ (II)

wherein $X^1$ and $X^2$ are hydrophilic groups; $Y^1$ and $Y^2$ are PDLA or PLLA; $L^1$ and $L^2$ are cleavable linkers, $Z^1$ is an anti-cancer agent, $Z^2$ is an imaging agent, and wherein (1) when $Y^1$ is PDLA then $Y^2$ is PLLA, and when $Y^1$ is PLLA then $Y^2$ is PDLA and (2) the ratio of the total number of D-lactic acid units in the stereocomplex to the total number of L-lactic acid units in the stereocomplex is from 0.9:1.1 to 1.1:0.9.

In another aspect, the stereocomplex is composed of the following components:

$X^1\text{-}Y^1\text{-}L^1\text{-}Z^1$ (I)

$X^2\text{-}Y^2\text{-}L^2\text{-}Z^2$ (II)

$X^5\text{-}Y^5\text{-}L^5\text{-}Z^5$ (IX)

wherein $X^1$, $X^2$, and $X^5$ are hydrophilic groups; $Y^1$, $Y^2$, and $Y^5$ are PDLA or PLLA; $L^1$, $L^2$, and $L^5$ are cleavable linkers, $Z^1$ and $Z^5$ are different anti-cancer agents, $Z^2$ is an imaging agent, and wherein the ratio of the total number of D-lactic acid units in the stereocomplex to the total number of L-lactic acid units in the stereocomplex is from 0.9:1.1 to 1.1:0.9.

In one aspect, the imaging agent can be a radiopharmaceutical such as $^{11}$C-L-methyl-methionine, $^{18}$F-fluorodeoxyglucose, $^{18}$F-sodium fluoride, $^{18}$F fluorochoilne, $^{18}$F desmethoxyfallypride, $^{67}$Ga—Ga$^{3+}$, $^{68}$Ga-dotatoc, $^{68}$Ga-PSMA, $^{111}$In-diethylenetriaminepentaacetic acid, $^{111}$In-lekuocytes, $^{111}$In-platelets, $^{111}$In-penetreotide, $^{111}$In-octreotide, $^{123}$I-iodide, $^{123}$I-o-iodohippurate, $^{123}$I-m-iodobenzylguanidine, $^{123}$I-FP-CIT, $^{125}$I-fibrinogen, $^{131}$I-iodide, $^{131}$I-m-iodobenzylguanidine, $^{81}$Kr$^m$-gas, $^{81}$Kr$^m$-aqueous solution, $^{13}$N-ammonia, $^{15}$O-water, $^{75}$Se-selenorcholesterol, $^{75}$Se-seleno-25-homo-taurocholate, $^{120}$Tl—Tl$^+$, $^{133}$Xe-gas, $^{133}$Xe in isotonic sodium chloride solution, $^{99}$Tc$^m$-pertechnetate, $^{99}$Tc$^m$-human albumin including macroaggregates or microspheres, $^{99}$Tc$^m$ phosphonates and/or phosphates, $^{99}$Tc$^m$-diethylenetriaminepentaacetic acid, $^{99}$Tc$^m$-dimercaptosuccinic acid, $^{99}$Tc$^m$-colloid, $^{99}$Tc$^m$-hepatic iminodiacetic acid, $^{99}$Tc$^m$ whole red blood cells, $^{99}$Tc$^m$-mercaptoacetyltriglycine, $^{99}$Tc$^m$ exametazime including exametazime labeled leucocytes, $^{99}$Tc$^m$ sesta-methoxy isobutyl isonitrile, $^{99}$Tc$^m$ IMMU-MN3 murine Fab'-SH antigranulocyte monoclonal antibody fragments, $^{99}$Tc$^m$-technegas, $^{99}$Tc$^m$ human immunoglobulin, $^{99}$Tc$^m$-tetrofosmin, $^{99}$Tc$^m$-ethyl cysteinate dimer, or another radiopharmaceutical. In still another aspect, the radiopharmaceutical is a metal ion accompanied by a chelating agent.

In another aspect, the imaging agent can be a radiocontrast agent. In a further aspect, the imaging agent can be an iodinated contrast agent and can be ionic, such as, for example, diatrizoate, metrizoate, iothalamate, or ioxaglate, or can be non-ionic such as, for example, iopamidol, iohexol, ioxilan, iopromide, iodixanol, ioversol, or can be another iodinated contrast agent. In a further aspect, the imaging agent can be based on barium sulfate or can be a gadolinium-based contrast agent such as, for example, gadoterate, gadodiamide, gadobenate, gadopentetate, gadoteridol, gadofosveset, gadoversetamide, gadoxetate, gadobutrol, or another gadolinium chelating agent.

In yet another aspect, the imaging agent can be an optical imaging agent useful for fluorescence, chromoendoscopy, or another optical imaging technique. In a further aspect, the imaging agent can be methylene blue, indigo carmine, or another nonspecific dye. In an alternative aspect, the imaging agent can be a fluorophore such as, for example, fluorescein isothiocyanate, indocyanine green, rosamine, BODIPY (boron-dipyrromethane) derivatives, chalcone, xanthone, oxazole yellow, thiazole orange, fluorescein, luciferin, Texas red, squaraine, a porphyrine, a phthalocyanine, a polymethine cyanine dye (e.g., Cy3, Cy5, Cy5.5, Cy7), an Alexa fluor, or a precursor molecule (e.g., 5-aminlevulinic acid) for a fluorescent metabolite (e.g., protoporphyrin X). In one aspect, the fluorophore can be a metal chelating agent.

A "quantum dot," as referred to herein, is a nanoparticle made from a semiconductor material. Quantum dots have properties that differ from larger semiconductor particles and materials; these properties are tunable with size and shape of the particles. Quantum dots may be useful in medical imaging. In one aspect, the imaging agents useful herein can include quantum dots which may be uncoated or which can be coated or encapsulated with a polymer or hydrogel. In one aspect, quantum dots have high extinction coefficients and are useful in fluorescence-based imaging techniques.

Additional Components

In addition to components (I) and (II), additional components can be used to produce the stereocomplexes. In one aspect, the stereocomplexes disclosed herein can include one or more additional components to perform functions such as maintain stereocomplex formation with different anti-cancer agent ratios, or to add one or more additional anti-cancer agents (aside from $Z^1$ and $Z^2$) to the stereocomplexes, to target a specific cell or tissue type, or to perform another function.

a. Anti-Cancer Agent Ratio Modifiers

In one aspect, provided herein are stereocomplexes further having the additional component (VII):

$$X^3\text{-}Y^3 \tag{VII}$$

wherein $X^3$ is a hydrophilic group as described previously and $Y^3$ is PDLA or PLLA.

In certain aspects, if a 1:1 ratio of two different anti-cancer agents ($Z^1$ and $Z^2$) is required, then equimolar amounts of components (I) and (II) can be used. However, in certain aspects, it is desirable to vary the relative amount of $Z^1$ and $Z^2$. The desired ratio of one anti-cancer agent to a second anti-cancer agent depends on the type of cancer being treated in the subject.

The inclusion of component (VII) allows for modification of the molar ratio of anti-cancer agents present in the stereocomplex while maintaining the optimal ratio of D-lactic acid units and L-lactic acid units for stereocomplex formation. As an example, the scheme below is provided to demonstrate how to produce a stereocomplex $Z^1$:$Z^2$ ratio of 2:1.

$$X^1\text{-PDLA-L}^1\text{-}Z^1 \quad \text{(I) (1 molar equivalent)}$$

$$X^2\text{-PLLA-L}^2\text{-}Z^2 \quad \text{(II) (0.5 molar equivalent)}$$

$$X^3\text{-PLLA} \quad \text{(VII) (0.5 molar equivalent)}$$

In this example, components (I), (II), and (VII) are admixed, where the number of D-lactic acid units in component (I) is equal to or approximately equal to the sum of the L-lactic acid units present in components (II) and (VII). Thus, by varying the amount of component (VII) that is added with a reduction in component (II), it is possible to vary the relative amount of $Z^1$ and $Z^2$ present in the stereocomplex and still balance the total number D- and L-lactic acid units in order to produce the stereocomplex (i.e., where the ratio of the total number of D-lactic acid units in the stereocomplex to the total number of L-lactic acid units in the stereocomplex is from 0.9:1.1 to 1.1:0.9).

In one aspect, PDLA or PLLA present in component (VII) has a molecular weight of from about 700 Da to about 5,000 Da, or about 750 Da to 4000 Da, or about 1,000 Da to about 3,000 Da. Further in this aspect, PDLA and PLLA has a molecular weight of about 700 Da, 750 Da, 800 Da, 900 Da, 1,000 Da, 1,250 Da, 1,500 Da, 2,000 Da, 2,500 Da, 3,000 Da, 3,500 Da, 4,000 Da, 4,500 Da, or 5,000 Da, where any value can be a lower and upper end-point of a range (e.g., 1,000 Da to 3,000 Da). In another aspect, PDLA or PLLA present in component (VII) has approximately the same molecular weight as that of PDLA and PLLA present in components (I) and (II).

In another aspect, the number of D-lactic acid units present in PDLA or L-lactic acid units present in PLLA in component (VII) is from 10, 15, 20, 25, 30, 35, 40, 45, 50, 55, 60, 65, 70, 75, 80, 85, 90, 95, or 100, where any value can be a lower and upper end-point of a range (e.g., 10 to 60). In another aspect, PDLA or PLLA present in component (VII) has the same number of D-lactic acid units and L-lactic acid units as that of PDLA and PLLA present in components (I) and (II).

In one aspect, $X^3$ in component (VII) is a polyalkylene glycol having molecular weight of from about 1,000 Da to about 5,000 Da, or from 1,500 Da to 4,500 Da, or from 2,000 Da to 4,000 Da, or have molecular weights of about 1,000 Da, 1,500 Da, 2,000 Da, 2,500 Da, 3,000 Da, 3,500 Da, 4,000 Da, 4,500 Da, or about 5,000 Da, where any value can be a lower and upper end-point of a range (e.g., 2,000 Da to 4,000 Da).

In another aspect, $X^3$ in component (VII) is monomethoxy polyethylene glycol having a molecular weight of from about 1,000 to about 5,000 Da, or from 1,500 Da to 4,500 Da, or from 2,000 Da to 4,000 Da, or have molecular weights of about 1,000 Da, 1,500 Da, 2,000 Da, 2,500 Da, 3,000 Da, 3,500 Da, 4,000 Da, 4,500 Da, or about 5,000 Da, where any value can be a lower and upper end-point of a range (e.g., 2,000 Da to 4,000 Da). In one aspect, $X^1$, $X^2$, and $X^3$ in components (I), (II), and (VII) of the stereocomplexes disclosed herein are each monomethoxy polyethylene glycol having the same molecular weight.

b. Targeting Group

In one aspect, the stereocomplexes disclosed herein can also include a component (VIII):

$$TA\text{-}X^4\text{-}Y^4 \tag{VII}$$

wherein $X^4$ is a hydrophilic group as discussed previously; $Y^4$ is PDLA or PLLA; and TA is a targeting agent or targeting group. In a further aspect, the stereocomplexes include two or more components (VIII) with different targeting groups. The targeting group TA is covalently bonded to the hydrophilic group $X^4$.

In one aspect, $X^4$ can be a polyalkylene glycol having a molecular weight of from about 1,000 Da to about 5,000 Da. Further in this aspect, the molecular weight of $X^4$ is greater than the molecular weight of $X^1$ and $X^2$ in components (I) and (II), respectively.

In one aspect, $X^4$ in component (VIII) is a polyalkylene glycol having molecular weight of from about 1,000 Da to about 5,000 Da, or from 1,500 Da to 4,500 Da, or from 2,000 Da to 4,000 Da, or have molecular weights of about 1,000 Da, 1,500 Da, 2,000 Da, 2,500 Da, 3,000 Da, 3,500 Da, 4,000 Da, 4,500 Da, or about 5,000 Da, where any value can be a lower and upper end-point of a range (e.g., 2,000 Da to 4,000 Da).

In another aspect, $X^4$ in component (VIII) is polyethylene glycol having a molecular weight of from about 1,000 to about 5,000 Da of from about 1,000 Da to about 5,000 Da, or from 1,500 Da to 4,500 Da, or from 2,000 Da to 4,000 Da, or have molecular weights of about 1,000 Da, 1,500 Da, 2,000 Da, 2,500 Da, 3,000 Da, 3,500 Da, 4,000 Da, 4,500 Da, or about 5,000 Da, where any value can be a lower and upper end-point of a range (e.g., 2,000 Da to 4,000 Da).

In one aspect, PDLA or PLLA present in component (VIII) has a molecular weight of from about 700 Da to about 5,000 Da, or about 750 Da to 4000 Da, or about 1,000 Da to about 3,000 Da. Further in this aspect, PDLA and PLLA has a molecular weight of about 700 Da, 750 Da, 800 Da, 900 Da, 1,000 Da, 1,250 Da, 1,500 Da, 2,000 Da, 2,500 Da, 3,000 Da, 3,500 Da, 4,000 Da, 4,500 Da, or 5,000 Da, where any value can be a lower and upper end-point of a range (e.g., 1,000 Da to 3,000 Da). In another aspect, PDLA or PLLA present in component (VIII) has approximately the same molecular weight as that of PDLA and PLLA present in components (I) and (II).

In another aspect, the number of D-lactic acid units present in PDLA or L-lactic acid units present in PLLA in component (VIII) is from 10, 15, 20, 25, 30, 35, 40, 45, 50, 55, 60, 65, 70, 75, 80, 85, 90, 95, or 100, where any value can be a lower and upper end-point of a range (e.g., 10 to 60). In another aspect, PDLA or PLLA present in component (VII) has the same number of D-lactic acid units and L-lactic acid units as that of PDLA and PLLA present in components (I) and (II).

The use of a targeting group in compound (VIII) with the stereocomplexes described herein can better localize the anti-cancer agents to specific sites in the body or specific tissue types. Further in these aspects, the targeting group improves the specificity of the stereocomplexes to cancer cells. In a further aspect, such targeting reduces the systemic side effects of the anti-cancer agent. In one aspect, the targeting group can be an antibody, antibody fragment, aptamer, peptide, oligosaccharide or other carbohydrate, a lectin, or a similar molecule. As targeting groups, structures complementary to cell surface antigens or receptors can be used. In one aspect, the targeting group is an antibody, an antibody fragment, a saccharide, an epitope-binding peptide, or an aptamer. In a further aspect, the targeting group can be a monosaccharide, disaccharide, oligosaccharide or a methacryloylated saccharide unit; an antibody such as IgG (rat immunoglobulin) or antibody fragment; a protein such as transferrin or melanocyte-stimulating hormone (MSH); or a peptide. In another aspect, the targeting group can be galactosamine, galactose, glucose, glucosamine, mannosamine, fucosylamine, lactose, a folate derivative, a hormone (e.g., MSH, secretin), an opiate, a monoclonal antibody, or polyclonal antibodies. In one aspect, the targeting group can be Fab' from the OV-TL16 antibody specific to CD47 (expressed on the majority of ovarian carcinoma cells) or an antibody towards prostate specific membrane antigen (PSMA).

In one aspect, the targeting group can be a peptide such as, for example, arginylglycylaspartic acid (RGD), which is a specific sequence recognized by integrins. As used herein, integrins are proteins that function to attach the cytoskeleton to the extracellular matrix (ECM) and that sense whether this adhesion has occurred. Further in this aspect, integrins are involved in cell adherence to the ECM, in apoptosis and its prevention, tissue regeneration, and other processes that are relevant to cancer cell proliferation. In still another aspect, integrins are overexpressed on tumor cells and tumor vasculature. In one aspect, an RGD targeting group as used herein will help deliver higher concentrations of the stereocomplexes disclosed herein to tumor tissues while minimizing interaction with nearby healthy cells. In a further aspect, the RGD targeting group can be linear or cyclic (i.e., cRGD).

In another aspect, the targeting group can be folic acid or folate. Further in this aspect, folate has a high affinity for the folate receptor, which captures ligands and concentrates them in the cytosol using an endocytosis mechanism. In one aspect, the folate receptor is overexpressed on the surface of malignant cancer cells and activated macrophages. In some aspects, activated macrophages are found in inflamed tissues and tissues with extensive symptoms of disease. Further in this aspect, using a folate ligand as a targeting group may help localize the stereocomplexes disclosed herein near tumors or other areas of diseased tissue.

In one aspect, component VIII has the structure

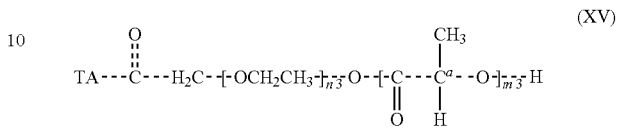

(XV)

wherein $n^3$ is from 45 to 90;
$m^3$ is from 15 to 60; and
the stereochemistry at $C^a$ is R or S.

Figure 3:
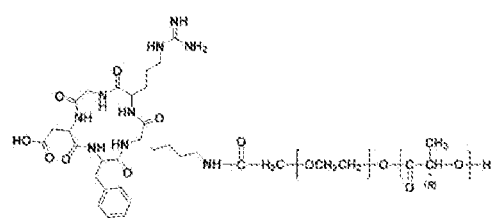
FIG. 3 shows the structures of cRGD-PEG-PDLA, FA-PEG-PLLA, and methyl-α-glucose-PEG-PDLA.
Figure 3:
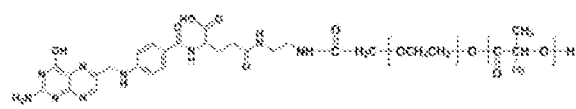
Figure 3:
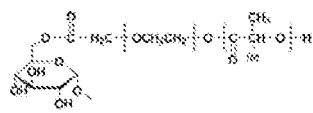

In one aspect, the targeting group (TA) in structure XV can be an unsubstituted or substituted sugar. Examples of sugars useful herein include, but are not limited to, glucose, ribose, galactose, mannose, fructose, fuculose, glucosamine, or fucoidan. In one aspect, the targeting group in structure XV is glucose or substituted glucose. In another aspect, the targeting group in structure XV is glucose substituted with one or more alkyl groups as defined herein, where one or more the hydroxyl protons of glucose can be substituted with an alkyl group. In another aspect, the targeting group in structure XV is glucose substituted with one or more methyl, ethyl, or propyl groups. In another aspect, the targeting group in structure XV is glucose substituted with one methyl group. In another aspect, the targeting group in structure XV is glucose where the C1 hydroxyl proton is substituted with a methyl group. In one aspect, the targeting group in structure XV is methyl-α-glucose or methyl-β-glucose. In another aspect, the targeting group in structure XV is methyl-α-glucose, where the methylated glucose moiety is covalently bonded to the carbonyl group in structure XV at the C6 hydroxyl position. This is depicted in FIG. 3.

Not wishing to be bound by theory, according to the Warburg effect, cancer cells require more glucose for faster proliferation. In some aspects, the transportation of glucose is supported by the GLUT family and SGLT family. SGLT transporters are seen in both early and late phases of tumor growth, whereas upregulated GLUT transporters are usually seen in the late phase of tumor development. Further in this aspect, using a sugar such as, for example, glucose or substituted glucose as a targeting group can increase the uptake and infiltration of the stereocomplexes described herein near or within the tumor, which ultimately results in an improvement of therapeutic efficacy.

In one aspect, the targeting group is a ligand for a cell-surface receptor on a cancer cell or a cell such as, for example, an endothelial cell, that is part of the vasculature of a solid tumor. In one aspect, biorecognition of a targeting group at the cell surface results in enhanced uptake of the stereocomplexes through receptor-mediated endocytosis, pinocytosis, or another selective mechanism. In a further aspect, this increased uptake results in an improvement in therapeutic efficacy.

In another aspect, subcellular targeting to specific organelles can be achieved through the use of specific targeting agents. In a further aspect, mitochondria can be targeted using positively-charged triphenylphosphonium ions linked to the stereocomplexes disclosed herein as previously described. In a related aspect, nuclear targeting may be achieved through the use of steroid hormones as targeting groups. Examples of component (VIII) are provided in FIG. 3.

The inclusion of component (VIII) allows for modification of the molar ratio of anti-cancer agents present in the stereocomplex while maintaining the optimal ratio of D-lactic acid units and L-lactic acid units for stereocomplex formation. As an example, the scheme below is provided to demonstrate how to produce a stereocomplex $Z^1:Z^2$ ratio of 2:1 using component (VIII), where the total number of D-lactic acid units is equal to the total number of L-lactic acid units.

$X^1$-PDLA-$L^1$-$Z^1$      (I) (1 molar equivalent)

$X^2$-PLLA-$L^2$-$Z^2$      (II) (0.5 molar equivalent)

TA-$X^4$-PLLA      (VIII) (0.5 molar equivalent)

In this example, components (I), (II), and (VIII) are admixed, where the number of D-lactic acid units in component (I) is equal to or approximately equal to the sum of the L-lactic acid units present in components (II) and (VIII). Thus, by varying the amount of component (VIII) that is added with a reduction in component (II), it is possible to vary the relative amount of $Z^1$ and $Z^2$ present in the stereocomplex and still balance the total number D- and L-lactic acid units in order to produce the stereocomplex (i.e., where the ratio of the total number of D-lactic acid units in the stereocomplex to the total number of L-lactic acid units in the stereocomplex is from 0.9:1.1 to 1.1:0.9).

In other aspects, component (VII) can be added to components (I), (II), and (VIII) to produce the stereocomplex. As an example, the scheme below is provided to demonstrate how to produce a stereocomplex $Z^1:Z^2$ ratio of 2:1 using components (VII) and (VIII), where the total number of D-lactic acid units is equal to the total number of L-lactic acid units.

$X^1$-PDLA-$L^1$-$Z^1$      (I) (1 molar equivalent)

$X^2$-PLLA-$L^2$-$Z^2$      (II) (0.5 molar equivalent)

$X^3$-PLLA      (VII) (0.25 molar equivalent)

TA-$X^4$-PLLA      (VIII) (0.25 molar equivalent)

c. Additional Anti-Cancer Agents

In another aspect, the stereocomplexes disclosed herein can include one or more components having formula (IX):

$X^5$-$Y^5$-$L^5$-$Z^5$      (IX)

wherein $X^5$ is a hydrophilic group as described previously; $Y^5$ is PDLA or PLLA; $L^5$ is a cleavable linker; and each $Z^5$ is an anti-cancer agent as described herein, where $Z^5$ is different from $Z^1$ and $Z^2$.

In one aspect, $X^5$ can be a polyalkylene glycol having a molecular weight of from about 1,000 Da to about 5,000 Da. In another aspect, $X^5$ in component (IX) is a polyalkylene glycol having molecular weight of from about 1,000 Da to about 5,000 Da, or from 1,500 Da to 4,500 Da, or from 2,000 Da to 4,000 Da, or have molecular weights of about 1,000 Da, 1,500 Da, 2,000 Da, 2,500 Da, 3,000 Da, 3,500 Da, 4,000 Da, 4,500 Da, or about 5,000 Da, where any value can be a lower and upper end-point of a range (e.g., 2,000 Da to 4,000 Da).

In another aspect, $X^5$ in component (IX) is polyethylene glycol having a molecular weight of from about 1,000 to about 5,000 Da, or from 1,500 Da to 4,500 Da, or from 2,000 Da to 4,000 Da, or have molecular weights of about 1,000 Da, 1,500 Da, 2,000 Da, 2,500 Da, 3,000 Da, 3,500 Da, 4,000 Da, 4,500 Da, or about 5,000 Da, where any value can be a lower and upper end-point of a range (e.g., 2,000 Da to 4,000 Da).

In one aspect, PDLA or PLLA present in component (IX) has a molecular weight of from about 700 Da to about 5,000 Da, or about 750 Da to 4000 Da, or about 1,000 Da to about 3,000 Da. Further in this aspect, PDLA and PLLA has a molecular weight of about 700 Da, 750 Da, 800 Da, 900 Da, 1,000 Da, 1,250 Da, 1,500 Da, 2,000 Da, 2,500 Da, 3,000 Da, 3,500 Da, 4,000 Da, 4,500 Da, or 5,000 Da, where any value can be a lower and upper end-point of a range (e.g., 1,000 Da to 3,000 Da). In another aspect, PDLA or PLLA present in component (IX) has approximately the same molecular weight as that of PDLA and PLLA present in components (I) and (II).

In another aspect, the number of D-lactic acid units present in PDLA or L-lactic acid units present in PLLA in component (IX) is from 10, 15, 20, 25, 30, 35, 40, 45, 50, 55, 60, 65, 70, 75, 80, 85, 90, 95, or 100, where any value can be a lower and upper end-point of a range (e.g., 10 to 60). In another aspect, PDLA or PLLA present in component (IX) has the same number of D-lactic acid units and L-lactic acid units as that of PDLA and PLLA present in components (I) and (II).

In one aspect, $L^5$ includes a cleavable group as described herein including, but not limited to, a disulfide group, an ester group, a hydrazone group, an acetal group, an imine group, a β-thiopropionate group, or an amide group. The cleavable linker $L^5$ can include one or more of these groups. The cleavable linker $L^5$ can also include additional functional groups so that the cleavable linker can be covalently bonded to PDLA or PLLA.

In some aspects, in this manner, by incorporating one or more components of formula (VIII) into the stereocomplexes, additional anti-cancer agents can be administered to a subject. In one aspect, three, four, or more anti-cancer agents can be incorporated into the stereocomplexes described herein.

The inclusion of component (IX) allows for modification of the molar ratio of anti-cancer agents present in the stereocomplex while maintaining the optimal ratio of D-lactic acid units and L-lactic acid units for stereocomplex formation. As an example, the scheme below is provided to demonstrate how to produce a stereocomplex $Z^1:Z^2:Z^5$ ratio of 2:1:1 using component (IX), where the total number of D-lactic acid units is equal to the total number of L-lactic acid units.

$X^1$-PDLA-$L^1$-$Z^1$      (I) (1 molar equivalent)

$X^2$-PLLA-$L^2$-$Z^2$      (II) (0.5 molar equivalent)

$X^5$-PLLA-$L^5$-$Z^5$      (IX) (0.5 molar equivalent)

In this example, components (I), (II), and (IX) are admixed, where the number of D-lactic acid units in component (I) is equal to or approximately equal to the sum of the L-lactic acid units present in components (II) and (VIII). Thus, by varying the amount of component (IX) that is added with a reduction in component (II), it is possible to vary the relative amount of $Z^1$, $Z^2$, and $Z^5$ present in the stereocomplex and still balance the total number D- and L-lactic acid units in order to produce the stereocomplex (i.e., where the ratio of the total number of D-lactic acid units in the stereocomplex to the total number of L-lactic acid units in the stereocomplex is from 0.9:1.1 to 1.1:0.9).

In other aspects, components (VII) and/or (VIII) can be added to components (I), (II), and (IX) to produce the stereocomplex.

d. Adjuvants

In one aspect, one or more adjuvants can be incorporated in the stereocomplexes described herein. For example, the adjuvant can be admixed with components I and II as described herein to produce a stereocomplex with adjuvant.

In one aspect, the adjuvant targets stromal cells. As used herein, "stromal cells" are the connective tissue cells in any organ and collectively form the stroma. In a further aspect, the interaction of stromal cells and cancer cells plays a role in cancer progression. In still a further aspect, stromal cells may release growth factors that promote cell division, or can provide an extracellular matrix that supports tumor cells. In a further aspect, stroma-rupturing agents can be used in the compositions disclosed herein. In one aspect, the stroma-rupturing agent can be an angiotensin receptor blocker such as, for example, losartan, azilsartan, candesartan, eprosartan, irbesartan, olmesartan, telmisartan, valsartan, or a combination thereof. In another aspect, the stroma-rupturing agent can be a flavonoid such as, for example, luteolin, quercetin, genistein, catechin, cyaniding, naringenin, delphinidin, malvidin, petunidin, peonidin, pelargonidin, gallocatechin, catechin-3-gallate, epicatechin, epigallocatechin, daidzein, glycetein, equol, kaempherol, myricetin, eriodictyol, hesperitin, taxifolin, or a combination thereof.

In another aspect, the adjuvant can target fibrosis and/or cancer-assisted fibrosis. In a further aspect, fibrosis is a component of the microenvironment of a tumor and can significantly affect behavior of the cancer. In a further aspect, fibrosis is characterized by infiltration and proliferation of multipotent stromal cells (i.e., mesenchymal cells) in the interstitial space. In a further aspect, anti-fibrosis agents can be used in the compositions disclosed herein. In one aspect, the anti-fibrosis agent can be a pyridine such as, for example, pirfenidone, mimosine, ciclopirox, diodone, bemegride, deferiprone, or a combination thereof. In another aspect, the anti-fibrosis agent can be N-acetylcysteine, etanrecept, bosentan, sildenafil, nintedanib, colchicine, or a combination thereof.

In another aspect, the adjuvant can be an aromatase inhibitors (anastrozole, letrozole, exemestane), estrogen blocker (tamoxifen, toremifene, fulvestrant, fulvestrant), blockers of ovarian function (goserelin, leuprolide), gonadotropin-releasing hormone agonists (buserelin, histrelin, leuprorelin, triptorelin, nafarelin), estrogen modulators (toremifene citrate), progestin therapeutic (megestrol acetate), LHRH agonists (firmagon), androgen-reducing agents (abiraterone, ketoconazole), anti-androgens (flutamide, bicalutamide, nilutamide, enzalutamide, apalutamide, darolutamide), and the like. In some aspects, these therapies can be used as adjuvants in the methods disclosed herein.

In yet another aspect, immunotherapies can be used as adjuvants in conjunction with the methods disclosed herein. In one aspect, these can include immune-suppressing agents including corticosteroids (hydrocortisone), methotrexate, and interferons (e.g., interferon α-2A, α-2b, α-n3, β-1a, β-1b, γ-1b, and the like).

e. Exemplary Components and Stereocomplexes

In one aspect, disclosed herein are stereocomplexes where component (I) has the following features: $X^1$ is monomethoxy polyethylene glycol having a molecular weight of from about 2,000 Da to about 4,000 Da, a number of L-lactic acid units or D-lactic acid units of from about 15 to about 60, $L^1$ includes a disulfide group, and $Z^1$ is mertansine (DM1). Further in this aspect, the components can be abbreviated as L-s-s-DM$_1$ and/or D-s-s-DM$_1$ to further specify polymer stereochemistry, linker group, and anti-cancer agent.

In another aspect, disclosed herein are stereocomplexes where component (I) has the structure (III):

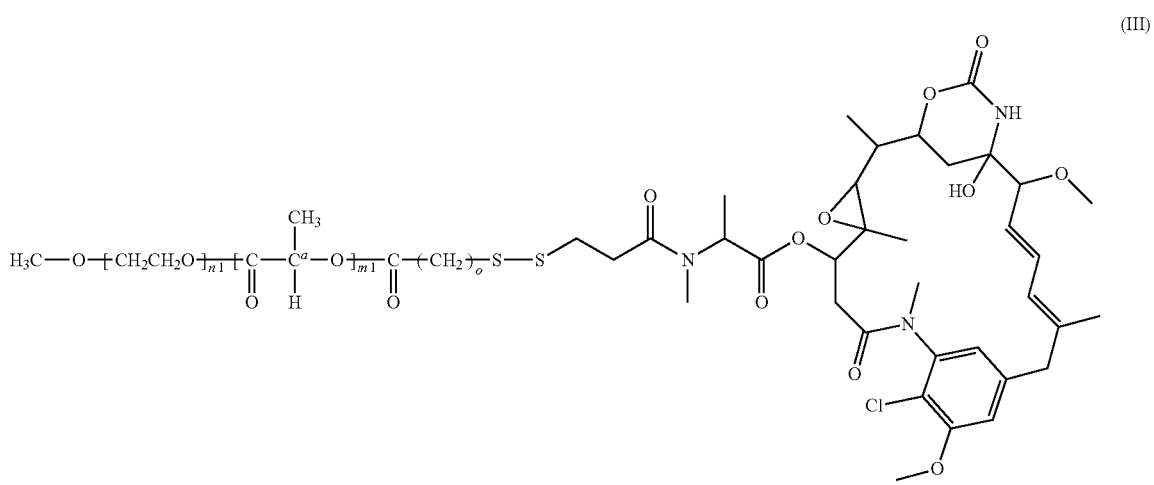

wherein n1 is from 45 to 90;
m$^1$ is from 15 to 60;
is from 1 to 4; and
the stereochemistry at C$^\alpha$ is R or S.

In a further aspect, o in formula (III) is 2.

In another aspect, disclosed herein are stereocomplexes where component (II) has the following features: X$^2$ is monomethoxy polyethylene glycol having a molecular weight of from about 2,000 Da to about 4,000 Da, a number of L-lactic acid units or D-lactic acid units from about 15 to about 60, L$^2$ includes an ester, hydrazone, or disulfide group, and Z$^2$ is docetaxel. In any of these aspects, docetaxel may be abbreviated as DTX (e.g., L-s-s-DTX would refer to a stereocomplex component with PLLA, a disulfide linkage, and docetaxel).

In another aspect, disclosed herein are stereocomplexes where component (II) has the structure (IV):

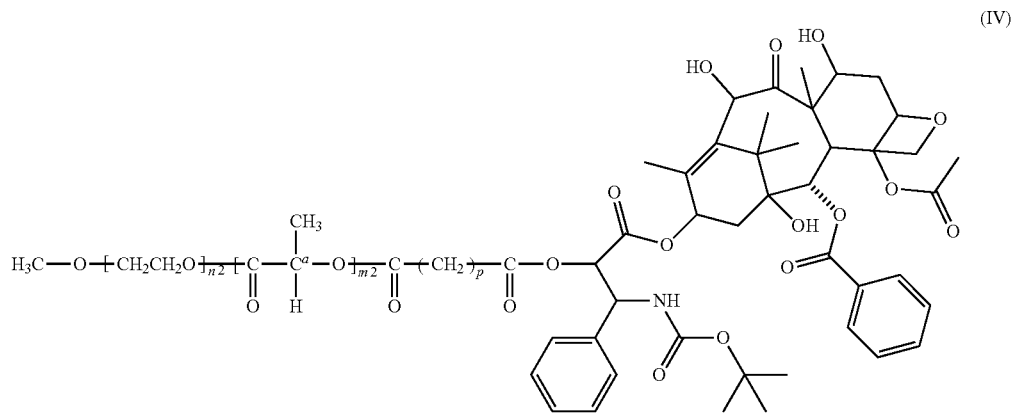

(IV)

wherein n2 is from 45 to 90;
m$^2$ is from 15 to 60;
p is from 0 to 7; and
the stereochemistry at C$^\alpha$ is R or S.

In one aspect, p in formula (IV) is 2.

In still another aspect, disclosed herein are stereocomplexes where component (II) has the structure (V):

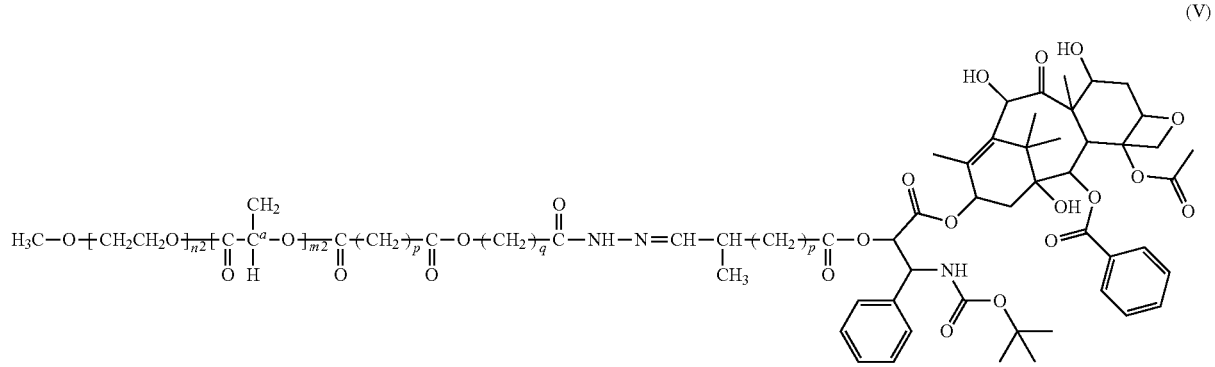

(V)

wherein n2 is from 45 to 90;
m² is from 15 to 60;
each p is independently from 0 to 7;
q is from 1 to 7; and
the stereochemistry at $C^\alpha$ is R or S.

In a further aspect, each p is 2, q is 3.

In still another aspect, disclosed herein are stereocomplexes where component (II) has the structure (VI):

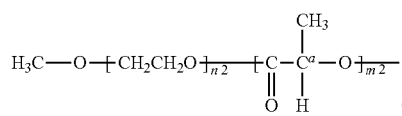
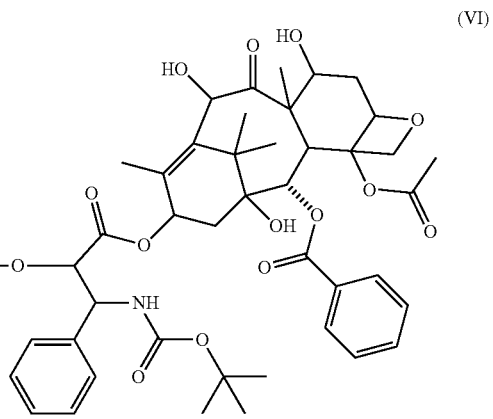

(VI)

wherein $n^2$ is from 45 to 90;
m² is from 15 to 60;
each p is independently from 0 to 7;
the stereochemistry at $C^\alpha$ is R or S.

In another aspect, in structure (VI), each p is 2.

f. Pharmaceutical Compositions

The stereocomplexes described herein can be combined with at least one pharmaceutically-acceptable carrier to produce a pharmaceutical composition. The pharmaceutical compositions can be prepared using techniques known in the art. In one aspect, the pharmaceutical composition is prepared by admixing the stereocomplexes with a pharmaceutically-acceptable carrier.

Pharmaceutically-acceptable carriers are known to those skilled in the art. These most typically would be standard carriers for administration to humans and/or other mammals, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents, and the like, in addition to the stereocomplexes described herein. Pharmaceutical compositions may also include one or more additional active ingredients such as antimicrobial agents, anti-inflammatory agents, anesthetics, and the like.

The pharmaceutical composition may be administered in a number of ways depending on whether local or systemic treatment is desired, and on the area to be treated. Administration may be parenterally, orally, subcutaneously, intralesionally, intraperitoneally, intravenously, or intramuscularly.

Preparations for administration include sterile aqueous or non-aqueous solutions, suspensions, and emulsions. Examples of non-aqueous carrier include alcoholic/aqueous solutions, emulsions, or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, antioxidants, chelating agents, inert gases, and the like.

In one aspect, provided herein is a pharmaceutical composition containing the stereocomplexes described herein and a pharmaceutically acceptable carrier or excipient.

Preparation and Characterization of the Stereocomplexes

In any of the above aspects, solutions of PLLA- and PDLA-conjugated polymers and anti-cancer and/or imaging agents, dissolved in compatible organic solvents can be mixed together with stirring and then replaced the solvents with buffer to prepare the stereocomplexes described herein. As with the precursor components, in some aspects, particle size of the stereocomplexes can be characterized using dynamic light scattering. In a further aspect, melting temperature of the crystalline anti-cancer agents, prepared prodrugs, and stereocomplexes can be characterized using a technique such as, for example, differential scanning calorimetry. Non-limiting methods for producing the stereocomplexes is provided in the Examples.

In one aspect, the stereocomplexes herein are nanoparticles. In a further aspect, the stereocomplexes have average diameters of from 50 to 500 nm, or from 100 to 400 nm, or from 100 to 200 nm. In a still further aspect, the diameters of the nanoparticles can be measured using dynamic light scattering (DLS), transmission electron microscopy (TEM), scanning electron microscopy (SEM), atomic force microscopy (AFM), photon correlation spectroscopy (PCS), x-ray diffraction (XRD), or other methods.

Applications of the Stereocomplexes

The stereocomplexes described herein are effective in delivering one, preferably two or more anti-cancer agents to a subject using a single delivery device. The selection of the cleavable linker can be varied for each component in the stereocomplex in order to deliver each anti-cancer agent at a specific rate (e.g., immediate release, delayed release, controlled release). Depending upon the type of cancer to be treated, the selection of the anti-cancer agents and cleavable linkers can be fine-tuned to maximize the efficiency of the stereocomplex to treat cancer. As will be demonstrated below, the stereocomplexes permit the safe delivery of two anti-cancer agents while minimizing unwanted side-effects associated with co-administration of the agents. Moreover, the stereocomplexes permit the delivery of the anti-cancer agents such that the agents synergistically affect one another.

In one aspect, when the stereocomplexes are nanoparticles, they have improved tumor targeting by using the "enhanced permeability and retention (EPR) effect. As used herein, the "enhanced permeability and retention (EPR) effect" refers to the tendency of nanoparticles to accumulate in tumor tissue more so than in healthy tissue. In one aspect, the stereocomplexes disclosed herein, due to their average particle size, tend to accumulate in or near cancer cells, in the absence of or in addition to any specific cellular targeting.

In another aspect, the stereocomplexes have an increased resistance to hydrolytic degradation. Not wishing to be bound by theory, due to the hydrophilic nature of the stereocomplexes, the hydrophilic linker can form a thick and dynamic hydration shell around the nanoparticles that can prevent the absorption of serum proteins on the surface of the nanoparticles. Additionally, the hydrophilic linkers of the stereocomplexes can reduce opsonization and clearance by the mononuclear phagocytic system (MPS), which can extend blood circulation time.

In another aspect, provided herein is a method for treating cancer in a subject, the method involving the step of administering the stereocomplexes disclosed herein to the subject. In a further aspect, the cancer can be pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumors.

In an alternative aspect, provided herein is a method for reducing the size of a tumor in a subject, the method involving the step of administering the stereocomplexes disclosed herein to the subject. In one aspect, the stereocomplexes can reduce the weight or volume of an existing tumor from 10% to 100% when compared to a control (i.e., no treatment with stereocomplex). In another aspect, the stereocomplexes can reduce the weight or volume of an existing tumor by 10%, 15%, 20%, 25%, 30%, 35%, 40%, 45%, 50%, 55%, 60%, 65%, 70%, 75%, 80%, 85%, 90%, 95%, or 100%, where any value can be a lower and upper end-point of a range (e.g., 30% to 70%, 50% to 90%, etc.). In one aspect, the stereocomplexes can eliminate the tumor such that the tumor no longer exists and does not return (i.e., remission). In another aspect, the stereocomplexes can prevent the growth of an existing tumor (i.e., suppression).

In one aspect, the stereocomplexes disclosed herein, alone or combined with pharmaceutically-acceptable carriers or excipients to form pharmaceutical compositions, can be administered to a subject in need of cancer treatment via intravenous injection. In one aspect, the stereocomplex can be administered to the subject at least once a week, at least two times per week, or at least three times per week. In other aspects, the stereocomplex can be administered every two weeks, three weeks, four weeks, six weeks, or eight weeks.

In another aspect, different populations of stereocomplex can be administered to the subject. For example, a first population of stereocomplex composed of components (I) and (II) with certain ratio of anti-cancer agents (e.g., $Z^1:Z^2$ at 2:1) can be prepared and administered, then a second population (e.g., $Z^1:Z^2$ at 1:1) can be subsequently administered. Alternatively, the second population can include a component with a different anti-cancer agent combination ($Z^1:Z^5$ or $Z^2:Z^5$).

In one aspect, the molar ratio of the anti-cancer agents $Z^1$ to $Z^2$ is from 10:1 to 1:10, or is about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10, where any value can be a lower and upper end-point of a range (e.g., 5:1 to 1:5).

In one further aspect, $Z^1$ in component (I) is mertansine and $Z^2$ in component (I) is docetaxel. In another aspect, the stereocomplex has a molar ratio of mertansine to docetaxel of from about 4:1 to about 1:10, or having a ratio of 4:1, 3:1, 2:1, 1:1, 1:2, 1:3, 1:4, 1:5, 1:6, 1:7, 1:8, 1:9, or 1:10, where any value can be a lower and upper end-point of a range (e.g., 5:1 to 1:5). In one aspect, the ratio of mertansine to docetaxel is from about 1:6 to about 1:10.

In another aspect, when the stereocomplex includes mertansine and docetaxel as the anti-cancer agents, the molar ratio of each agent can be varied depending upon the cancer to be treated. Below is a table providing molar ratios of components described herein to produce stereocomplexes for treating various types of cancer (cell line in parenthesis; components (III), (IV), and (V) defined above).

TABLE 3

| Cancer | Molar Ratio of Components (III), (IV), and (V) |
| --- | --- |
| Gastric (SGC-7901) | III:IV 1:1 to 1:14 |
| Gastric (SGC-7901) | III:V 4:1 to 1:14 |
| Lung (NCI-H460) | III:V 1:6 to 1:14 |
| Breast (MCF-7) | III:IV 4:1 to 1:1 and 1:8 to 1:14 |
| Breast (MCF-7) | III:V 1:4 to 1:6 |
| Lung (A549) | III:IV 1:4 to 1:12 |
| Pancreatic (MIAPaCa-2) | III:IV 4:1 to 1:14 |

In one aspect, the dosage of DM1 administered to the subject in stereocomplex is from about 2 mg/kg to about 5 mg/kg of body weight per single administration, or about 2, about 2.5, about 3, about 3.5, about 4, about 4.5, or about 5 mg/kg, where any value can be a lower and upper end-point of a range (e.g., about 2.5 mg/kg to about 4 mg/kg, about 3.5 mg/kg to about 4.5 mg/kg, etc.). In another aspect, the dosage of docetaxel administered to the subject in stereocomplex is from about 12 mg/kg to about 50 mg/kg of body weight per single administration, or about 12, about 15, about 20, about 25, about 30, about 35, about 40, about 45, or about 50 mg/kg, where any value can be a lower and upper end-point of a range (e.g., about 15 mg/kg to about 40 mg/kg, about 25 to about 35 mg/kg, etc.).

In one aspect, the single unit dosage of DM1 administered to the subject in stereocomplex is from about 0.5 mg/m$^2$ to about 15 mg/m$^2$, where the unit mg/m$^2$ is the body surface area calculated on height and weight. In another aspect, the single unit dosage of DM1 administered to the subject in stereocomplex is about 0.5 mg/m$^2$, 1 mg/m$^2$, 1.5 mg/m$^2$, 2 mg/m$^2$, 2.5 mg/m$^2$, 3 mg/m$^2$, 3.5 mg/m$^2$, 4 mg/m$^2$, 4.5 mg/m$^2$, 5 mg/m$^2$, 5.5 mg/m$^2$, 6 mg/m$^2$, 6.5 mg/m$^2$, 7 mg/m$^2$, 7.5 mg/m$^2$, 8 mg/m$^2$, 8.5 mg/m$^2$, 9 mg/m$^2$, 9.5 mg/m$^2$, 10 mg/m$^2$, 10.5 mg/m$^2$, 11 mg/m$^2$, 11.5 mg/m$^2$, 12 mg/m$^2$, 12.5 mg/m$^2$, 13 mg/m$^2$, 13.5 mg/m$^2$, 14 mg/m$^2$, 14.5 mg/m$^2$, 15 mg/m$^2$, where any value can be a lower and upper end-point of a range (e.g., about 1 mg/m$^2$ to about 6 mg/m$^2$, about 3 mg/m$^2$ to about 5 mg/m$^2$, etc.).

In one aspect, the single unit dosage of docetaxel administered to the subject in stereocomplex is from about 3 mg/m$^2$ to about 135 mg/m$^2$, where the unit mg/m$^2$ is the body surface area calculated on height and weight. In another aspect, the single unit dosage of docetaxel administered to the subject in stereocomplex is about 3 mg/m$^2$, 5 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 80 mg/m², 85 mg/m², 90 mg/m², 95 mg/m², 100 mg/m², 105 mg/m², 110 mg/m², 115 mg/m², 120 mg/m², 125 mg/m², 130 mg/m², 135 mg/m², where any value can be a lower and upper end-point of a range (e.g., about 5 mg/m² to about 70 mg/m², about 20 mg/m² to about 60 mg/m², etc.).

In one aspect, chemotherapy with the stereocomplexes disclosed herein can be used in combination with one or more other treatment strategies including, but not limited to, surgical excision of all or part of the tumor or affected organ or tissue, radiotherapy, high intensity focused ultrasound, magnetic hyperthermia, photothermal therapy, immunotherapy, or a combination thereof.

Aspects

The following listing of exemplary aspects supports and is supported by the disclosure provided herein.

Aspect 1: A stereocomplex comprising the components

wherein
  each $X^1$ and $X^2$ is a hydrophilic group;
  each $Y^1$ and $Y^2$ is PDLA or PLLA;
  each $L^1$ and $L^2$ is a cleavable linker;
  $Z^1$ is an anti-cancer agent,
  $Z^2$ is an anti-cancer agent or imaging agent, wherein when $Z^2$ is an anti-cancer agent, $Z^1$ and $Z^2$ are different anti-cancer agents; and wherein (1) when $Y^1$ is PDLA then $Y^2$ is PLLA, and when $Y^1$ is PLLA then $Y^2$ is PDLA and (2) the ratio of the total number of D-lactic acid units in the stereocomplex to the total number of L-lactic acid units in the stereocomplex is from 0.9:1.1 to 1.1:0.9.

Aspect 2: The stereocomplex of Aspect 1, wherein $X^1$ and $X^2$ are different hydrophilic groups.

Aspect 3: The stereocomplex of Aspect 1, wherein $X^1$ and $X^2$ are the same hydrophilic group.

Aspect 4: The stereocomplex of Aspect 1, wherein $X^1$ and $X^2$ are each a polyalkylene glycol.

Aspect 5: The stereocomplex of Aspect 1, wherein $X^1$ and $X^2$ are each a polyalkylene glycol having a molecular weight from 1,000 Da to 5,000 Da.

Aspect 6: The stereocomplex of Aspect 1, wherein $X^1$ and $X^2$ are each a polyethylene glycol having a molecular weight from 1,000 Da to 5,000 Da.

Aspect 7: The stereocomplex in any one of Aspect 1, wherein $X^1$ and $X^2$ are each a monomethoxy polyethylene glycol having a molecular weight from 1,000 Da to 5,000 Da.

Aspect 8: The stereocomplex in any one of Aspects 1-7 wherein PDLA and PLLA has a molecular weight from 700 Da to 5,000 Da.

Aspect 9: The stereocomplex in any one of Aspects 1-8, wherein $L^1$ and $L^2$ are different linkers.

Aspect 10: The stereocomplex in any one of Aspects 1-8, wherein $L^1$ and $L^2$ are the same linker.

Aspect 11: The stereocomplex in any one of Aspects 1-8, wherein $L^1$ and $L^2$ are independently containing a disulfide group, an ester group, a hydrazone group, an acetal group, an imine group, a β-thiopropionate group, or an amide group.

Aspect 12: The stereocomplex in any one of Aspects 1-11, wherein $Z^1$ and $Z^2$ are independently paclitaxel, doxorubicin, gemcitabine, cisplatin, methotrexate, 5-fluorouracil, betulinic acid, amphotericin B, diazepam, nystatin, propofol, testosterone, estrogen, prednisolone, prednisone, 2,3 mercaptopropanol, progesterone, docetaxel, a maytansinoid, a PD-1 inhibitor, a PD-L1 inhibitor, a protein kinase inhibitor, a P-glycoprotein inhibitor, an autophage inhibitor, a PARP inhibitor, an aromatase inhibitor, a monoclonal antibody, a photosensitizer, a radiosensitizer, an interleukin, an antiandrogen, or any combination thereof.

Aspect 13: The stereocomplex of Aspect 12, wherein the maytansinoid is ansamitocin, mertansine (DM1) or ravtansine.

Aspect 14: The stereocomplex in any one of Aspects 1-13, wherein the molar ratio of $Z^1$ to $Z^2$ is from 10:1 to 1:10.

Aspect 15: The stereocomplex in any one of Aspects 1-14, wherein $Z^1$ is mertansine and $Z^2$ is docetaxel.

Aspect 16: The stereocomplex in any one of Aspects 1-15, wherein for component I, $X^1$ is monomethoxy polyethylene glycol having a molecular weight from 2,000 Da to 4,000 Da, the number of L-lactic acid units or D-lactic acid units is from 15 to 60, $L^1$ comprises a disulfide group, and $Z^1$ is mertansine (DM1).

Aspect 17: The stereocomplex of Aspect 16, wherein component I has the following structure:

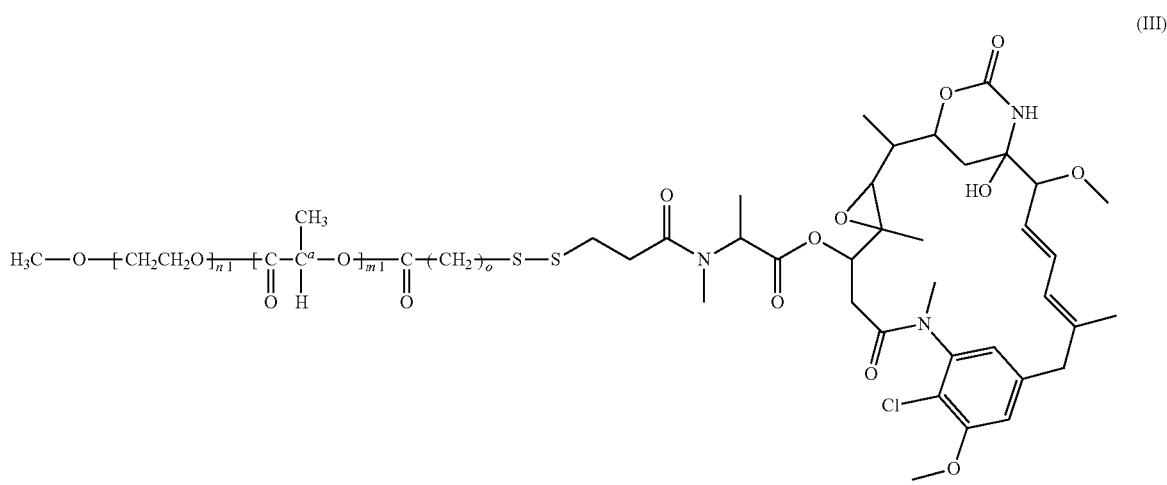

wherein n1 is from 45 to 90;
m¹ is from 15 to 60;
o is from 1 to 4; and
the stereochemistry at $C^a$ is R or S.

Aspect 18: The stereocomplex of Aspect 17, wherein o is 2.

Aspect 19: The stereocomplex in any one of Aspects 16-18, wherein for component II, $X^2$ is monomethoxy polyethylene glycol having a molecular weight from 2,000 Da to 4,000 Da, the number of L-lactic acid units or D-lactic acid units is from 15 to 60, $L^2$ comprises an ester, hydrazone or disulfide group, and $Z^2$ is docetaxel.

Aspect 20: The stereocomplex of Aspect 19, wherein the molar ratio of mertansine to docetaxel is from 4:1 to 1:10.

Aspect 21: The stereocomplex of Aspect 19, wherein component II has the following structure:

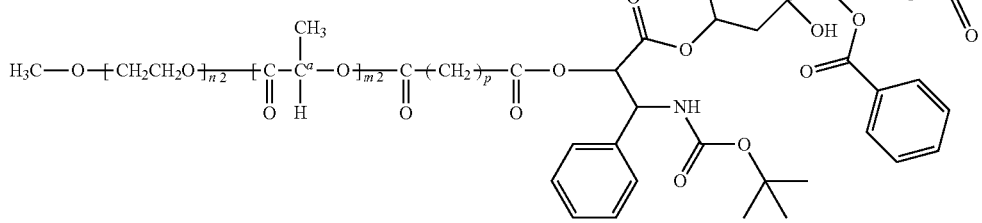

(IV)

wherein n2 is from 45 to 90;
m² is from 15 to 60;
p is from 0 to 7; and
the stereochemistry at $C^a$ is R or S.

Aspect 22: The stereocomplex of Aspect 21, wherein p is 2.

Aspect 23: The stereocomplex of Aspect 19, wherein component II has the following structure:

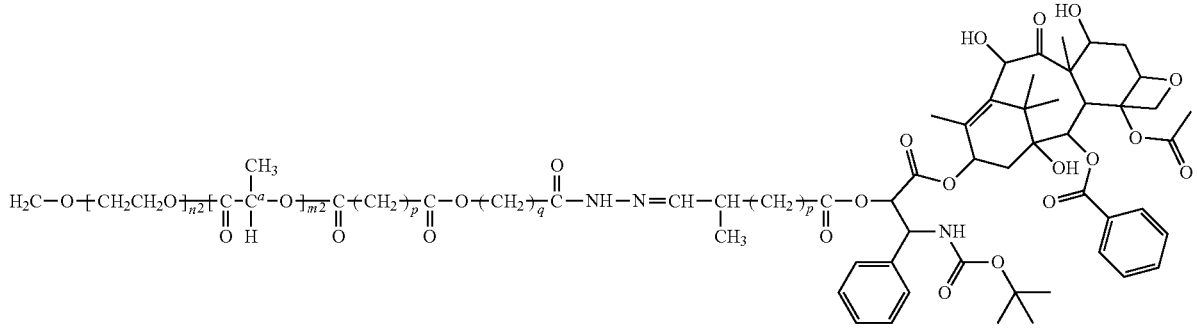

(V)

wherein n2 is from 45 to 90;
m² is from 15 to 60;
each p is independently from 0 to 7;
q is from 1 to 7; and
the stereochemistry at $C^a$ is R or S.

Aspect 24: The stereocomplex of Aspect 23, wherein each p is 2, and q is 3.

Aspect 25: The stereocomplex of Aspect 19, wherein component II has the following structure

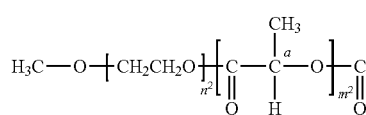

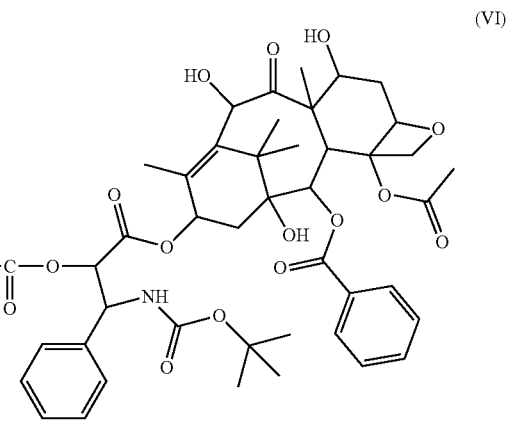

(VI)

wherein n2 is from 45 to 90;
m² is from 15 to 60;
each p is independently from 0 to 7;
the stereochemistry at $C^a$ is R or S.

Aspect 26: The stereocomplex of Aspect 25, wherein each p is 2.

Aspect 27: The stereocomplex in any one of Aspects 1-26, wherein the stereocomplex further comprises component VII $$X^3\text{-}Y^3 \quad (VII)$$

wherein
$X^3$ is a hydrophilic group; and
$Y^3$ is PDLA or PLLA.

Aspect 28: The stereocomplex of Aspect 27, wherein $X^3$ is a polyalkylene glycol having a molecular weight from 1,000 Da to 5,000 Da.

Aspect 29: The stereocomplex of Aspect 27, wherein $X^3$ is a polyethylene glycol having a molecular weight from 1,000 Da to 5,000 Da.

Aspect 30: The stereocomplex of Aspect 27, wherein $X^3$ is monomethoxy polyethylene glycol having a molecular weight from 1,000 Da to 5,000 Da.

Aspect 31: The stereocomplex of Aspect 27, wherein $X^3$ is monomethoxy polyethylene glycol having a molecular weight from 2,000 Da to 4,000 Da, and the number of L-lactic acid units or D-lactic acid units present in PDLA or PLLA is from 15 to 60.

Aspect 32: The stereocomplex of Aspects 1-31, wherein the stereocomplex further comprises component VIII $$TA\text{-}X^4\text{-}Y^4 \quad (VII)$$

wherein
$X^4$ is a hydrophilic group;
$Y^4$ is PDLA or PLLA; and
TA is a targeting group.

Aspect 33: The stereocomplex of Aspect 32, wherein $X^4$ is a polyalkylene glycol having a molecular weight from 1,000 Da to 5,000 Da, wherein the molecular weight of $X^4$ is greater than the molecular weight of $X^1$ and $X^2$.

Aspect 34: The stereocomplex of Aspect 32, wherein $X^4$ is a polyethylene glycol having a molecular weight from 1,000 Da to 5,000 Da, wherein the molecular weight of $X^4$ is greater than the molecular weight of $X^1$ and $X^2$.

Aspect 35: The stereocomplex of Aspect 32, wherein $X^4$ is polyethylene glycol having a molecular weight from 2,000 Da to 4,000 Da, and the number of L-lactic acid units or D-lactic acid units present in PDLA or PLLA is from 15 to 60.

Aspect 36: The stereocomplex of Aspect 32, wherein TA is a ligand.

Aspect 37: The stereocomplex of Aspect 32, wherein the component VIII has the structure

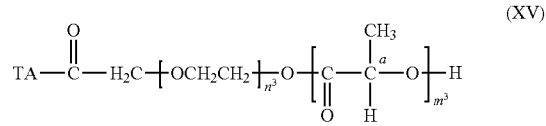

(XV)

wherein n³ is from 45 to 90;
m³ is from 15 to 60; and
the stereochemistry at $C^a$ is R or S.

Aspect 38: The stereocomplex of Aspect 32, wherein TA is an unsubstituted or substituted sugar.

Aspect 39: The stereocomplex of Aspect 38, wherein the sugar is ribose, galactose, mannose, fructose, fuculose, glucosamine, or fucoidan.

Aspect 40: The stereocomplex of Aspect 32, wherein TA is glucose or substituted glucose.

Aspect 41: The stereocomplex of Aspect 40, wherein TA is alkyl substituted glucose.

Aspect 42: The stereocomplex of Aspect 40, wherein TA is methyl-α-glucose or methyl-ß-glucose.

Aspect 43: The stereocomplex in any one of Aspects 1-42, wherein the stereocomplex further comprises one or more components of formula IX $$X^5\text{-}Y^5\text{-}L^5\text{-}Z^5 \quad (IX)$$

wherein
X⁵ is a hydrophilic group;
Y⁵ is PDLA or PLLA;
L⁵ is a cleavable linker; and
Z⁵ is an anti-cancer agent, wherein Z⁵ is different from Z¹ and Z².

Aspect 44: The stereocomplex in any one of Aspects 1-44, wherein Z² is an imaging agent and wherein the imaging agent comprises a radiopharmaceutical, a radiocontrast agent, an optical imaging agent or precursor thereof, a quantum dot, or a combination thereof.

Aspect 45: The stereocomplex of Aspect 44, wherein the radiopharmaceutical comprises $^{11}$C-L-methyl-methionine, $^{18}$F-fluorodeoxyglucose, $^{18}$F-sodium fluoride, $^{18}$F fluorochoilne, $^{18}$F desmethoxyfallypride, $^{67}$Ga—Ga$^{3+}$, $^{68}$Ga-dotatoc, $^{68}$Ga-PSMA, $^{111}$In-diethylenetriaminepentaacetic acid, $^{111}$In-lekuocytes, $^{111}$In-platelets, $^{111}$In-pentreotide, $^{111}$In-octreotide, $^{123}$I-iodide, $^{123}$I-o-iodohippurate, $^{123}$I-m-iodobenzylguanidine, $^{123}$I-FP-CIT, $^{125}$I-fibrinogen, $^{131}$I-iodide, $^{131}$I-m-iodobenzylguanidine, $^{81}$Kr$^m$-gas, $^{81}$Kr$^m$-aqueous solution, $^{13}$N-ammonia, $^{15}$O-water, $^{75}$Se-selenorcholesterol, $^{75}$Se-seleno-25-homo-tauro-cholate, $^{120}$Tl—Tl$^+$, $^{133}$Xe-gas, $^{133}$Xe in isotonic sodium chloride solution, $^{99}$Tc$^m$-pertechnetate, $^{99}$Tc$^m$-human albumin including macroaggregates or microspheres, $^{99}$Tc$^m$ phosphonates and/or phosphates, $^{99}$Tc$^m$-diethylenetriaminepentaacetic acid, $^{99}$Tc$^m$-dimercaptosuccinic acid, $^{99}$Tc$^m$-colloid, $^{99}$Tc$^m$-hepatic iminodiacetic acid, $^{99}$Tc$^m$ whole red blood cells, $^{99}$Tc$^m$-mercaptoacetyltriglycine, $^{99}$Tc$^m$ exametazime including exametazime labeled leucocytes, $^{99}$Tc$^m$ sesta-methoxy isobutyl isonitrile, $^{99}$Tc$^m$ IMMU-MN3 murine Fab'-SH antigranulocyte monoclonal antibody fragments, $^{99}$Tc$^m$-technegas, $^{99}$Tc$^m$ human immunoglobulin, $^{99}$Tc$^m$-tetrofosmin, $^{99}$Tc$^m$-ethyl cysteinate dimer, or another radiopharmaceutical.

Aspect 46: The stereocomplex of Aspect 44, wherein the radiocontrast agent comprises diatrizoate, metrizoate, iothalamate, ioxaglate, iopamidol, iohexol, ioxilan, iopromide, iodixanol, ioversol, another iodinated contrast agent, barium sulfate, gadoterate, gadodiamide, gadobenate, gadopentetate, gadoteridol, gadofosveset, gadoversetamide, gadoxetate, gadobutrol, or another gadolinium chelating agent.

Aspect 47: The stereocomplex of Aspect 44, wherein the optical imaging agent or precursor thereof comprises methylene blue, indigo carmine, another nonspecific dye, fluorescein isothiocyanate, indocyanine green, rosamine, BODIPY (boron-dipyrromethane) derivatives, chalcone, xanthone, oxazole yellow, thiazole orange, fluorescein, luciferin, Texas red, squaraine, a porphyrine, a phthalocyanine, a polymethine cyanine dye including Cy3. Cy5, Cy5.5, or Cy7, an Alexa fluor, 5-aminolevulinic acid, a metal chelating agent, or another optical imaging agent.

Aspect 48: The stereocomplex in any one of Aspects 1-47, wherein the stereocomplex further comprises an adjuvant.

Aspect 49: The stereocomplex of Aspect 48, wherein the adjuvant comprises a stroma-rupturing agent, an anti-fibrosis agent, an aromatase inhibitor, immune-suppressing agent, an estrogen blocker, a gonadotropin-releasing hormone agonist, an estrogen modulator, a progestin therapeutic, a LHRH agonist, an androgen-reducing agent, an anti-androgen, an immune-suppressing agent, or any combination thereof.

Aspect 50: The stereocomplex of Aspect 48, wherein the adjuvant comprises a stroma-rupturing agent, wherein the stroma-rupturing agent comprises losartan, azilsartan, candesartan, eprosartan, irbesartan, olmesartan, telmisartan, valsartan, luteolin, quercetin, genistein, catechin, cyaniding, naringenin, delphinidin, malvidin, petunidin, peonidin, pelargonidin, gallocatechin, catechin-3-gallate, epicatechin, epigallocatechin, daidzein, glycetein, equol, kaempherol, myricetin, eriodictyol, hesperitin, taxifolin, or any combination thereof.

Aspect 51: The stereocomplex of Aspect 48, wherein the adjuvant comprises an anti-fibrosis agent, wherein the anti-fibrosis agent comprises pirfenidone, mimosine, ciclopirox, diodone, bemegride, deferiprone, etanrecept, bosentan, sildenafil, nintedanib, colchicine, or a combination thereof.

Aspect 52: The stereocomplex of Aspect 1, wherein component I has the following structure:

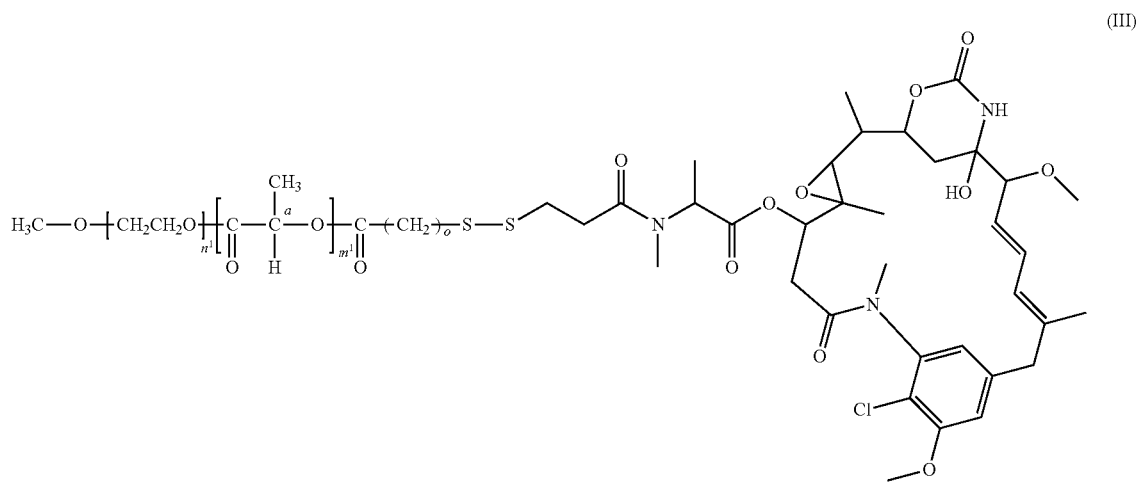

(III)

wherein n1 is from 45 to 90;
m¹ is from 15 to 60;
o is from 1 to 4; and
the stereochemistry at $C^\alpha$ is R or S; and
component II has the following structure:

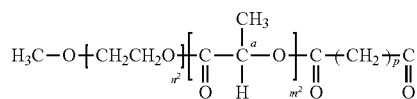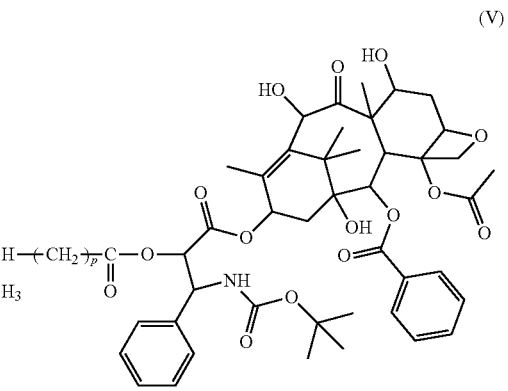

(V)

wherein n2 is from 45 to 90;
m² is from 15 to 60;
each p is independently from 0 to 7;
q is from 1 to 7; and
the stereochemistry at $C^\alpha$ is R or S.
wherein the ratio of the total number of D-lactic acid units in the stereocomplex to the total number of L-lactic acid units in the stereocomplex is from 0.9:1.1 to 1.1:0.9.

Aspect 53: The stereocomplex of Aspect 52, wherein o is 2; each p is 2; and q is 3.

Aspect 54: The stereocomplex of Aspects 1-53, wherein the stereocomplex has an average diameter from 50 nm to 200 nm.

Aspect 55: A pharmaceutical composition comprising the stereocomplex in any one of Aspects 1-54 and a pharmaceutically acceptable carrier.

Aspect 56: A method for treating cancer in a subject comprising administering to the subject the stereocomplex in any one of Aspects 1-54.

Aspect 57: The method of Aspect 50, wherein the cancer is pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumor.

Aspect 58: A method for reducing a tumor in a subject comprising administering to the subject the stereocomplex in any one of Aspects 1-54.

Aspect 59: The method in any one of Aspects 56-58, wherein the stereocomplex is administered to the subject by intravenous injection.

Aspect 60: The method in any one of Aspects 56-59, wherein component I has the following structure:

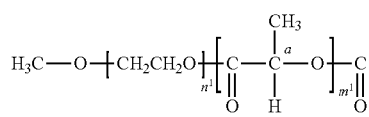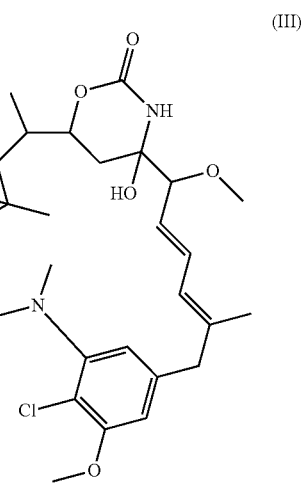

(III)

wherein n1 is from 45 to 90;
m¹ is from 15 to 60;
o is from 1 to 4; and
the stereochemistry at C$^\alpha$ is R or S; and
component II has the following structure:

(V)

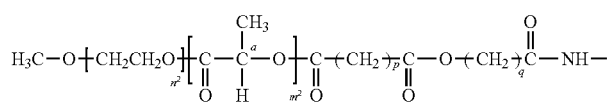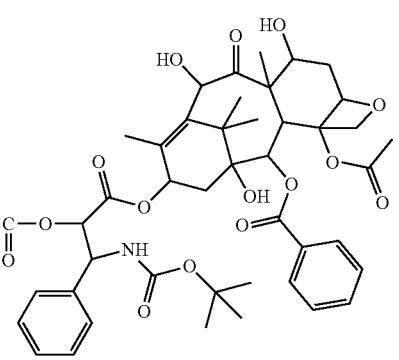

wherein n² is from 45 to 90;
m² is from 15 to 60;
each p is independently from 0 to 7;
q is from 1 to 7; and
the stereochemistry at C$^\alpha$ is R or S.
wherein the ratio of the total number of D-lactic acid units in the stereocomplex to the total number of L-lactic acid units in the stereocomplex is from 0.9:1.1 to 1.1:0.9.

Aspect 61: The method of Aspect 60, wherein o is 2; each p is 2; and q is 3.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions) can be used to optimize the product purity and yield obtained from the described process. Only reasonable and routine experimentation will be required to optimize such process conditions.

Example 1: Synthesis of Polymer Conjugated Drugs

Synthesis of mPEG-PD/LLA:

mPEG-PD/LLA copolymer was synthesized by ring-opening polymerization with mPEG-OH as initiator. Briefly, in a flame-dried and nitrogen-purged flask, distilled mPEG ($M_n$=2000) and recrystallized D/L-lactide were added under N$_2$ stream. After stannous octoate (in toluene) and toluene were added to the flask sequentially, the sealed flask was maintained at 120° C. for 24 h. The synthesized polymer was recovered by precipitation in ice-cooled diethyl ether. The resultant precipitate was filtered and dried under vacuum at room temperature and yield was calculated to be 90%.

Figure 4:
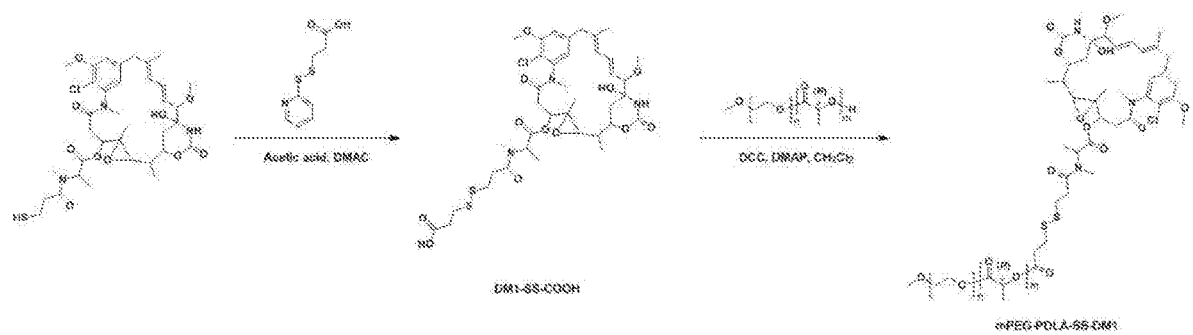
FIG. 4 shows a synthetic scheme for producing mPEG-PDLA-SS-DM1.

Synthesis of DM1-SS-COOH:

Mertansine (DM1) and 3-(pyridin-2-yldisulfanyl)propanoic acid were dissolved in N,N-dimethylacetamide (DM1, 3-(pyridin-2-yldisulfanyl)propanoic acid stoichiometric molar ratio: 1:2), followed by addition of acetic acid (10 μL/mL of reaction solution). After stirred at 35°C for 24 hours under a nitrogen atmosphere, the reaction solution was cooled to room temperature, and then dialyzed against deionized water. After lyophilization, the resulting product was obtained and used in the next step without further purification and yield was calculated to be 88%. A schematic for the synthesis is shown in FIG. 4.

Figure 5:
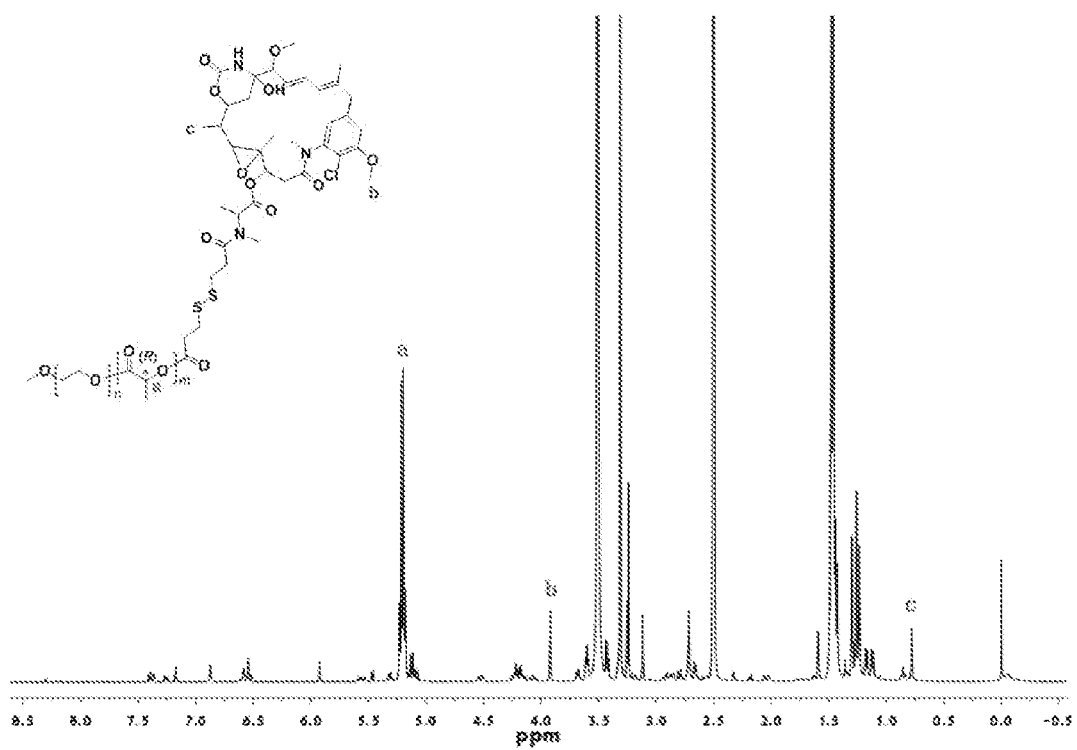
FIG. 5 shows 1H NMR of mPEG-PDLA-SS-DM1 in DMSO-$d_6$. Peaks that are lettered correspond to the same letters on the inset structure; a: —CH— of PDLA; b and c: —$CH_3$ of DM1.

Synthesis of mPEG-PDLA-SS-DM1:

mPEG-PDLA copolymer, DM1-SS-COOH, DCC, and DMAP were dissolved in dry dichloromethane and cooled with an ice bath (mPEG-PDLA:DM1-SS-COOH:DCC:DMAP stoichiometric molar ratio: 1:1:2:2). The reaction was stirred at 0° ° C. for 48 hours under a nitrogen atmosphere, followed by filtered and concentrated under reduced pressure. The DM1 conjugated mPEG-PDLA was recovered by precipitation in cold diethyl ether and dried under vacuum. To remove free DM1-SS-COOH, gel permeation chromatography (GPC) with THF as mobile phase was used and yield was calculated to be 64%. A schematic for the synthesis is shown in FIG. 4. FIG. 5 shows 1H NMR of the purified product.

Figure 6:
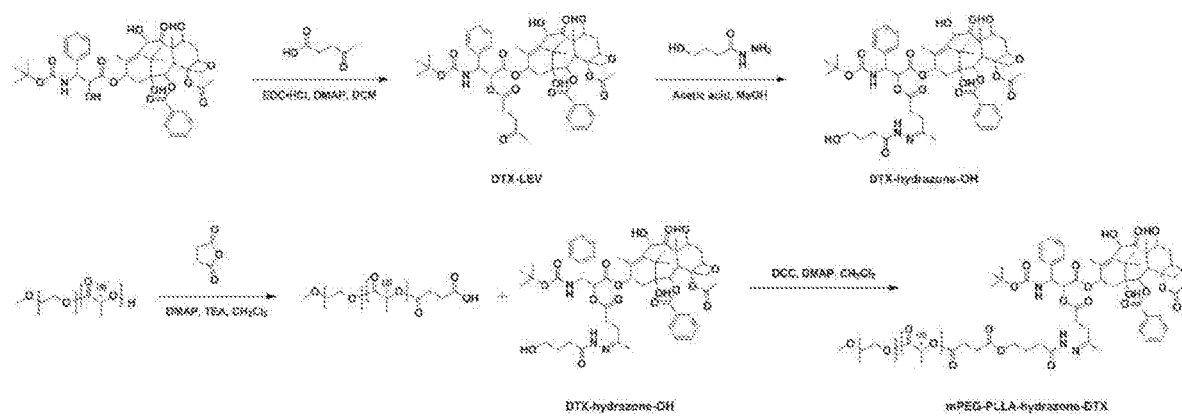
FIG. 6 shows a synthetic scheme for producing mPEG-PLLA-hydrazone-DTX.

Synthesis of DTX-LEV:

Docetaxel (DTX) was esterified on 2'-hydroxyl of DTX with LEV to afford the respective ester derivate. Briefly, EDC·HCl and LEV were dissolved in dichloromethane under stirring at 4°C for 30 min. Then dichloromethane solution of DTX and DMAP was added to the reaction (DTX:EDC·HCl:DMAP:LEV stoichiometric molar ratio: 1:2:2:2). The reaction was kept stirring at 4° C. under nitrogen atmosphere overnight. After being washed with 0.05 N HCl twice and sat. NaCl once, the organic phase was dried over anhydrous Na$_2$SO$_4$ and concentrated under reduced pressure to give the product with a 77% yield. A schematic for synthesis is shown in FIG. 6.

Synthesis of DTX-hydrazone-OH:

The hydrazone contained derivative of DTX was achieved by the reaction of DTX-LEV 4-hydroxybutanehydrazide. Briefly, DTX-LEV and 4-hydroxybutanehydrazide were dissolved in anhydrous methanol under stirring at 45° C.

(DTX-LEV: 4-hydroxybutanehydrazide stoichiometric molar ratio: 1:10). The reaction was performed for 2 hours after addition of acetic acid (10 μL/mL of reaction solution). Then the reaction solution was cooled to room temperature, and washed with saturated NaHCO$_3$ to remove acetic acid and unreacted 4-hydroxybutanehydrazide, followed by extracting with acetyl acetate, drying over anhydrous NaSO$_4$, and concentrating under reduced pressure to give the crude product, which was purified with silica gel column chromatography using CH$_2$Cl$_2$:MeOH (90:10) as mobile phase with a yield of 72%. A schematic for synthesis is shown in FIG. 6.

Synthesis of mPEG-PLLA-COOH:

Succinic anhydride, DMAP and mPEG-PLLA were dissolved in dichloromethane followed by addition of TEA (mPEG-PLLA:succinic anhydride:DMAP:TEA stoichiometric molar ratio: 1:2:2:2). After carried out at room temperature for 24 hours, the reaction solution was washed with 0.1M HCl and Di-water twice, respectively, to remove DMAP and unreacted succinic anhydride, then dried over anhydrous Na$_2$SO$_4$ and concentrated under reduced pressure. By precipitation in cold diethyl ether, the resulting mPEG-PLLA-COOH was retrieved with a yield of 78%. A schematic for synthesis is shown in FIG. 6.

Figure 7:
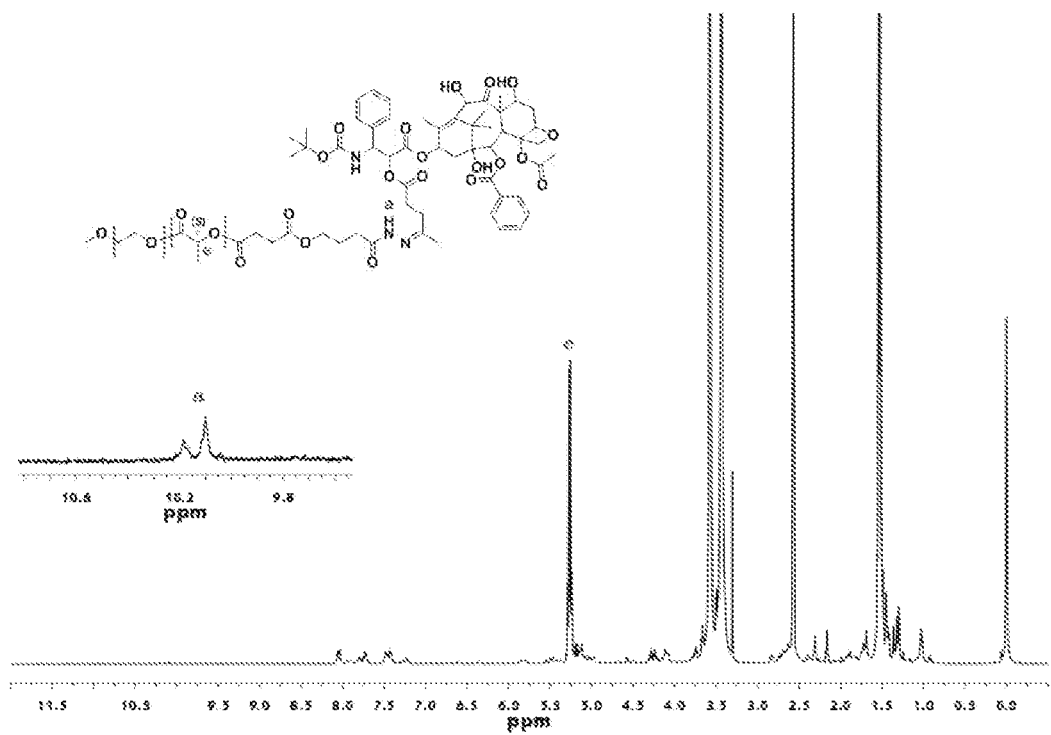
FIG. 7 shows 1H NMR of mPEG-PLLA-hydrazone-DTX in DMSO-$d_6$. Peaks that are lettered correspond to the same letters on the inset structure; a: —NH— of DTX-hydrazone-OH; e: —CH— of PLLA.

Synthesis of mPEG-PLLA-hydrazone-DTX:

Distilled mPEG-PLLA-COOH, DTX-hydrazone-OH, DCC, and DMAP were dissolved in dry dichloromethane and cooled with ice bath (mPEG-PLLA-COOH:DTX-hydrazone-OH:DCC:DMAP stoichiometric molar ratio: 1:1.2:2:2). The reaction was stirred at 0° C. for 48 hours under nitrogen atmosphere, then filtered and concentrated under reduced pressure. The DTX conjugated mPEG-PLLA was recovered by precipitation in cold diethyl ether and dried under vacuum. The final product was purified by preparative gel permeation chromatography with THE as mobile phase. The yield was calculated to be 60%. A schematic for synthesis is shown in FIG. 6. FIG. 7 shows 1H NMR of the purified product.

Figure 8:
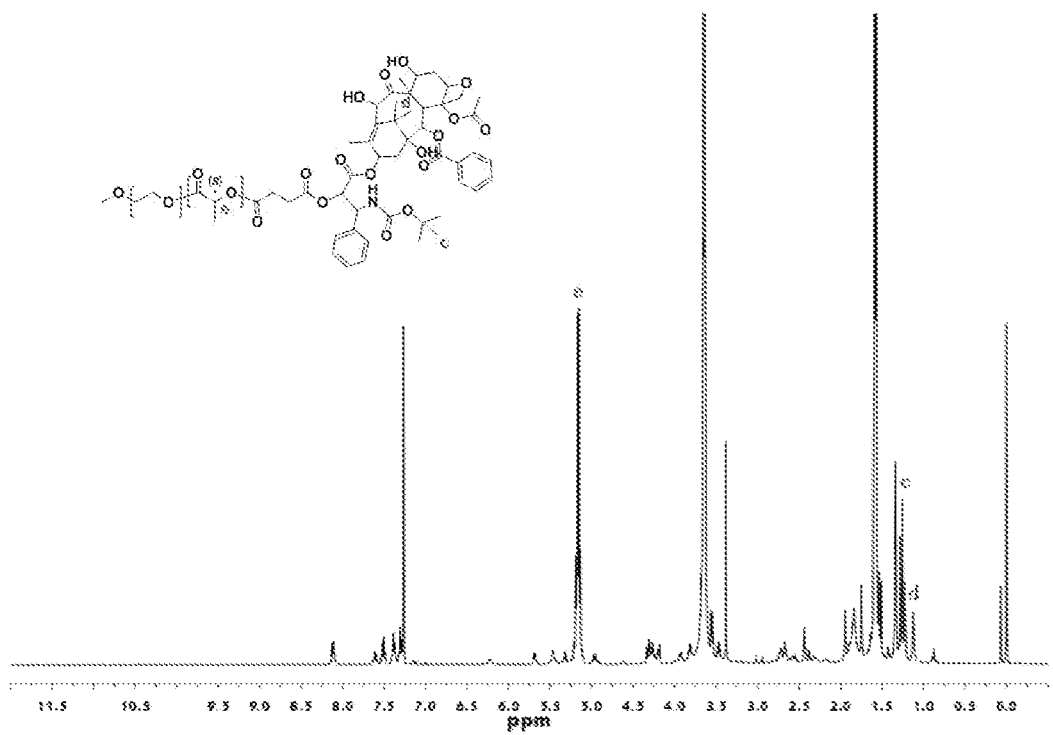
FIG. 8 shows 1H NMR of mPEG-PLLA-ester-DTX in $CDCl_3$. Peaks that are lettered correspond to the same letters on the inset structure; c and d: —$CH_3$ of DTX; e: —CH— of PLLA.

Synthesis of mPEG-PLLA-ester-DTX:

Distilled mPEG-PLLA-COOH (previously described), DTX, DCC, and DMAP were dissolved in dry dichloromethane and cooled with an ice bath (mPEG-PLLA-COOH:DTX:DCC:DMAP stoichiometric molar ratio: 1:2:2:2). The reaction was stirred at 0° C. for 48 hours under a nitrogen atmosphere, then filtered and concentrated under reduced pressure. The DTX conjugated mPEG-PLLA was recovered by precipitation in cold diethyl ether and dried under vacuum. To remove free DTX, GPC with THE as mobile phase was used. The yield was calculated to be 42%. FIG. 8 shows 1H NMR of the purified product.

Figure 9:
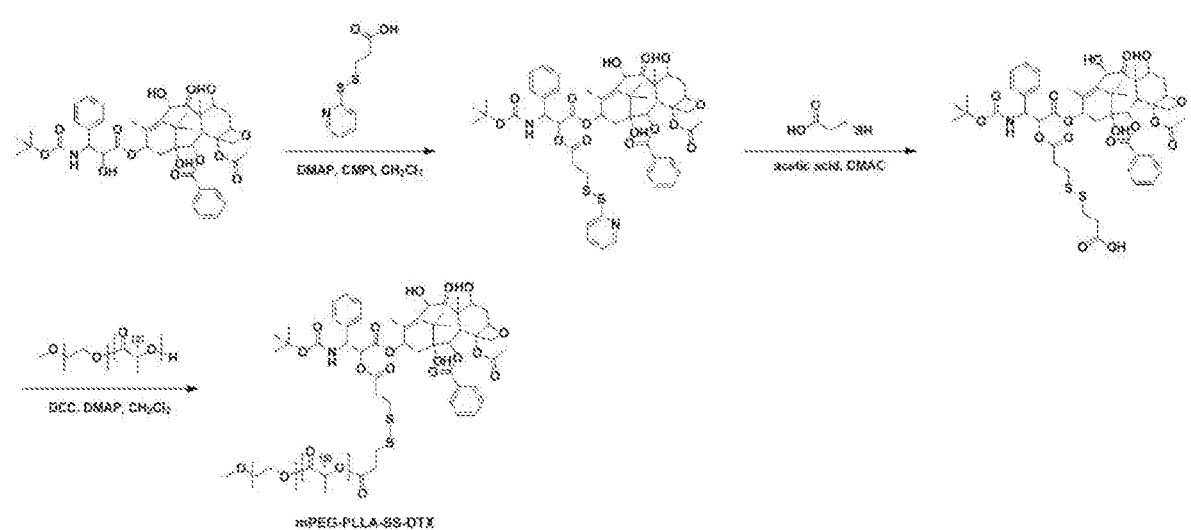
FIG. 9 shows a synthetic scheme for producing mPEG-PLLA-SS-DTX.

Synthesis of DTX-SS-Pyridine:

DTX was esterified on the 2'-hydroxyl of DTX with 3-(pyridin-2-yldisulfanyl)propanoic acid to afford the respective ester derivate. Briefly, DTX, 3-(pyridin-2-yldisulfanyl)propanoic acid, CMPI and DMAP were dissolved in anhydrous CH$_2$Cl$_2$ (DTX: 3-(pyridin-2-yldisulfanyl)propanoic acid:CMPI:DMAP stoichiometric molar ratio: 1:1.2:2.4). The reaction mixture was stirred at 40° C. for 1 hour. The resulting reaction solution was concentrated under reduced pressure to give the crude product, which was purified with silica gel column chromatography using CH$_2$Cl$_2$:acetyl acetate (50:50) as mobile phase with a yield of 80%. A schematic for synthesis is shown in FIG. 9.

Synthesis of DTX-SS-COOH:

DTX-SS-Pyridine and 3-mercaptopropanoic acid were dissolved in N,N-dimethylacetamide (DTX-SS-Pyridine, 3-mercaptopropanoic acid stoichiometric molar ratio: 1:1.1), followed by addition of acetic acid (10 μL/mL of reaction solution). After stirring at 35° C. for 24 hours under nitrogen atmosphere, the reaction solution was cooled to room temperature and dialyzed against deionized water. After lyophilization, the resulting product was obtained and used in the next step without further purification. The yield was estimated to be approximately 75%. A schematic for synthesis is shown in FIG. 9.

Synthesis of mPEG-PLLA-SS-DTX:

Distilled mPEG-PLLA copolymer, DTX-SS-COOH, DCC, and DMAP were dissolved in dry dichloromethane and cooled with an ice bath (mPEG-PLLA:DTX-SS-COOH:DCC:DMAP stoichiometric molar ratio: 1:1.2:2.4:2.4). The reaction was stirred at 0° ° C. to r.t. for 48 hours under nitrogen atmosphere, followed by filtration and concentration under reduced pressure. The resulting mPEG-PLLA-SS-DTX conjugate was recovered by precipitation in cold diethyl ether and dried under vacuum. To remove free DTX-SS-COOH, GPC with THE as mobile phase was used. A schematic for synthesis is shown in FIG. 9.

Synthesis of HOOC-PEG-PDLA:

HOOC-PEG-PDLA copolymer was synthesized by ring-opening polymerization with COOH-PEG-OH as initiator. Briefly, in a flame-dried and nitrogen-purged flask, distilled HOOC-PEG ($M_n$=3500) and recrystallized D-lactide were added under N$_2$ stream. After stannous octoate (in toluene) and toluene were added to the flask sequentially, the sealed flask was maintained at 120° C. for 24 hours. The synthesized polymer was recovered by precipitation in ice-cooled diethyl ether. The resultant precipitate was filtered and dried at room temperature under vacuum for a yield of 88%.

Figure 10:
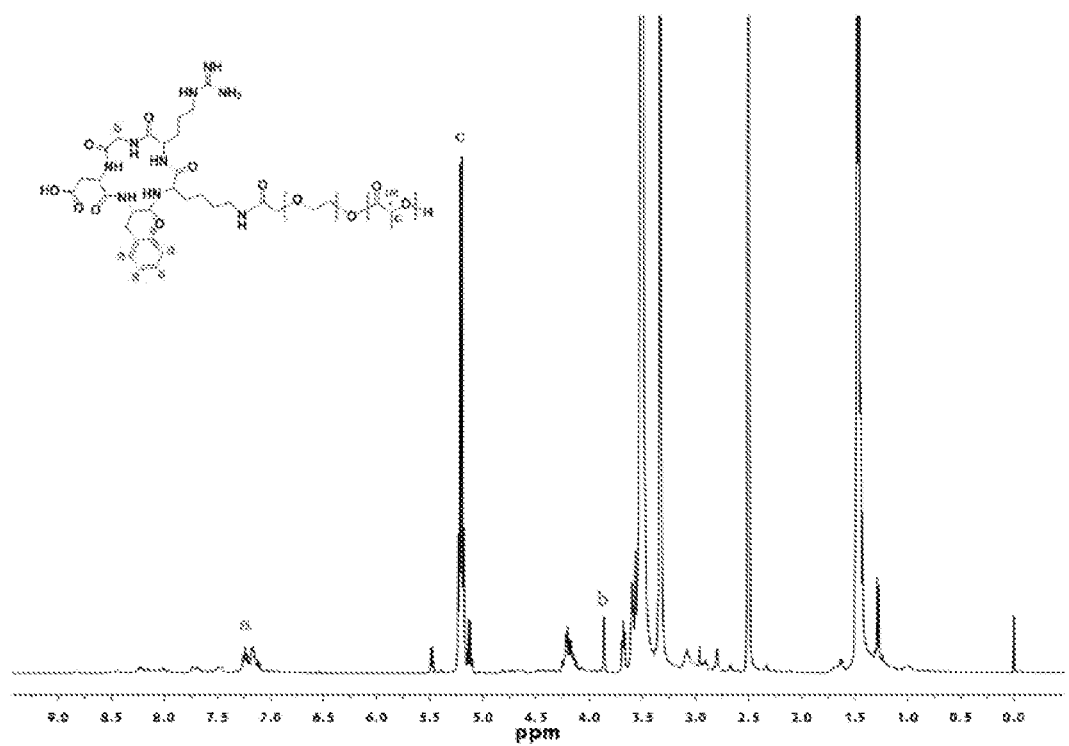
FIG. 10 shows 1H NMR of cRGD-amide-PEG-PDLA in DMSO-$d_6$. Peaks that are lettered correspond to the same letters on the inset structure; a: =CH— of cRGD; b: —$CH_2$— of cRGD; c: —CH— of PDLA.

Synthesis of cRGD-amide-PEG-PDLA:

HOOC-PEG-PDLA was dissolved in DMF and activated with HBTU for 1 hour under stirring at room temperature, followed by addition of a DMF solution of cRGD and DIEA (HOOC-PEG-PLLA:cRGD:HBTU:DIEA stoichiometric molar ratio: 1:1.1:3:3). After being kept at room temperature for 24 hours under nitrogen atmosphere, the reaction was filtered and recovered by precipitation in ice-cooled diethyl ether. The resultant precipitate was re-dissolved in DMF and dialyzed against water. After lyophilization, the resulting cRGD-amide-PEG-PDLA was obtained with a yield of 75%. FIG. 10 shows 1H NMR of the purified product.

Synthesis of Maleimide-PEG-PDLA:

Maleimide-PEG-PDLA copolymer was synthesized by ring-opening polymerization with maleimide-PEG-OH as initiator. Briefly, in a flame-dried and nitrogen-purged flask, distilled maleimide-PEG ($M_n$=3500) and recrystallized D-lactide were added under N$_2$ stream. After stannous octoate (in toluene) and toluene were added to the flask sequentially, the sealed flask was maintained at 120° C. for 24 hours. The synthesized polymer was recovered by precipitation in ice-cooled diethyl ether. The resultant precipitate was filtered and dried at room temperature under vacuum. The yield was calculated to be 67%.

Synthesis of cRGD-S-PEG-PDLA:

Maleimide-PEG-PDLA and cRGDfc were dissolved in DMF (Maleimide-PEG-PDLA:cRGDfc stoichiometric molar ratio: 1:1.2). The reaction mixture was stirred at room temperature under nitrogen atmosphere for overnight. The final mixture was dialyzed against deionized water. After lyophilization, the resulting CRGD-Maleimide-PEG-PDLA was obtained.

Synthesis of Folate-NH$_2$:

Folate was dissolved in DMSO followed by addition of NHS and DCC. After activated for 6 hours at 50° C. under nitrogen atmosphere in dark, the DMSO solution of ethane- 1,2-diamine and pyridine was added to the reaction mixture (Folate:ethane-1,2-diamine:NHS:DCC:pyridine stoichiometric molar ratio: 1:2:2:2:1). Then the reaction was allowed to proceed at room temperature for 24 hours. The mixture was filtered, precipitated in ACN, and placed at 4° ° C. overnight before being centrifuged (4000 rpm, 5 min). The solid was washed twice with ethanol and dried under vacuum, then used in the next step without further purification. The yield was estimated to be 58%.

Figure 11:
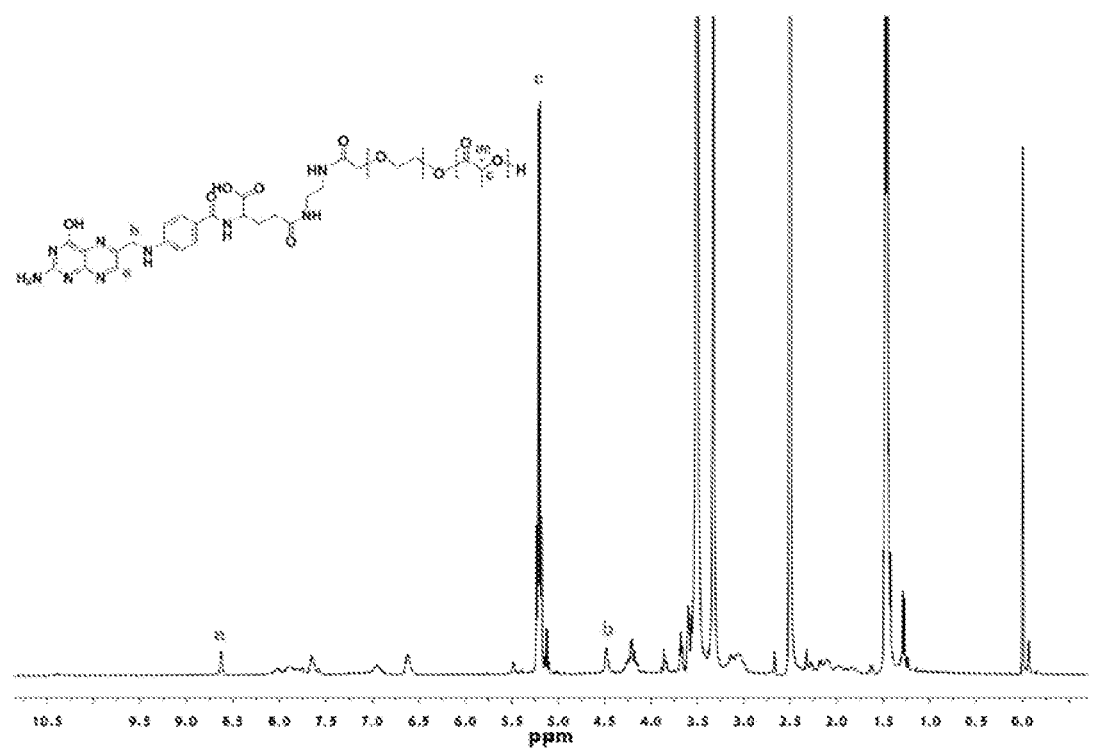
FIG. 11 shows 1H NMR of folate-amide-PEG-PLLA in DMSO-$d_6$. Peaks that are lettered correspond to the same letters on the inset structure; a: =CH— of folate; b: —$CH_2$— of folate; c: —CH— of PDLA.

Synthesis of Folate-amide-PEG-PL/DLA:

Distilled HOOC-PEG-PL/DLA (previously described), NHS, and EDC·HCl were dissolved in DMSO. The reaction mixture was stirred at room temperature under a nitrogen atmosphere overnight. Then, DMSO solution of folate-$NH_2$ was added to the mixture followed by keeping at room temperature in dark for 24 hours (HOOC-PEG-PL/DLA:folate-$NH_2$:NHS:EDC·HCl:pyridine stoichiometric molar ratio: 1:2:1.5:1.5). The final mixture was dialyzed against DMSO and water, sequentially. After lyophilization, the resulting Folate-amide-PEG-PL/DLA was obtained with a yield of 53%. FIG. 11 shows 1H NMR of the purified product.

Figure 12:
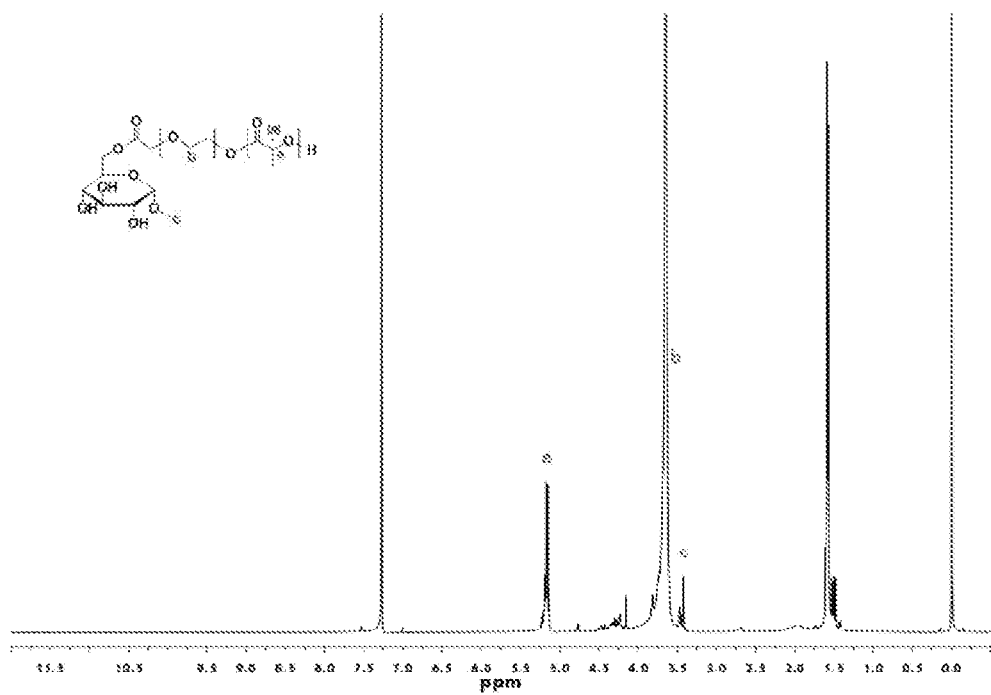
FIG. 12 shows 1H NMR of methyl-α-glucose-PEG-PDLA in $CDCl_3$. Peaks that are lettered correspond to the same letters on the inset structure; a: —CH— of PDLA; b: —$CH_2$— of PEG; c: —$CH_3$ of glucose.

Synthesis of Glu-PEG-PDLA:

HOOC-PEG-PDLA, methyl α-D-glucopyranoside, and lipase 435 were suspended in acetonitrile. The mixture was homogenized for 5 days under 50 degree. The enzyme was filtered off, subsequently, the solvent was evaporated. The residue was dissolved in $CH_2Cl_2$, followed by washing with di-water. The organic phase was dried over anhydrous $Na_2SO_4$ and concentrated. The resulting Glu-PEG-PDLA conjugate was recovered by precipitation in cold diethyl ether with a yield of 80%. FIG. 12 shows $^1H$ NMR of the purified product.

Example 2: Preparation of the Stereocomplex

D-DM1 Formulation Preparation mPEG-PDLA-SS-DM1 was dissolved in 0.5 mL DMF and 0.5 mL DMSO at a concentration of 20 mg/mL. The solution was added into Di-PBS dropwise. After stirring 1 hour at room temperature, the mixture was transferred to a dialysis membrane (cutoff 3.5K) to remove solvent by dialysis against PBS for two days. After filtering with a 450 nm filter, the size of the D-DM1 formulation was characterized by dynamic light scattering (Zetasizer from Malvern Instruments, Malvern, UK). The concentration of DM1 was tested by HPLC with the help of DTT. Briefly, 100 μl D-DM1 solution was lyophilized to powder. Then, 1 mL DMF solution containing 40 mM DTT was used to dissolve the powder and sonicated for 30 mins. The content of DM1 was evaluated using RP-HPLC system with UV detection at 254 nm using a mixture of acetonitrile and water (v/v, 60/40) as mobile phase. The standard curve of DM1 was given by Y=14.51448X−15.43867 (Y=peak area; X=DM1 concentration; $r^2$=0.99709; 1-50 ug/ml)

L-DTX Formulation Preparation mPEG-PLLA-Hydrazone-DTX was dissolved in 1 mL DMSO at a final concentration of 30 mg/mL. The DMSO solution was added into Di-PBS dropwise. After stirring 1 hour at room temperature, the mixture was transferred to a dialysis membrane (cutoff 3.5K) to remove solvent by dialysis against PBS for two days. After filtering with a 450 nm filter, the size of the L-DTX formulation was characterized by dynamic light scattering (Zetasizer from Malvern Instruments, Malvern, UK). The concentration of DTX was tested by HPLC after alkaline degradation. Briefly, L-DTX sample solution (80 μL), 6M NaOH (200 μL) and water (220 μL) were added to 15 ml centrifuge tube in sequence. The mixture was incubated in water bath at 60° ° C. overnight. Next, 6M formic acid (250 μL) was added and the volume of solution was adjusted to 3 mL with water. The solution containing benzoic acid, which was derived from the degradation of DTX in alkaline solution, was used for HPCL. The mobile phase was ammonium acetate (20 mM) and methanol in 90:10 ratio. The column effluent was detected at 230 nm. Benzoic acid standard dissolved in methanol was used to prepare a calibration curve. The mass conversion ratio of DTX:benzoic acid is 6.62:1. The calibration curve of benzoic acid is Y=5.8601X−3.9858 (Y=peak area, X=DTX concentration; r2=0.99871; 6.62-132.4 μg/mL)

Complex Formulation Preparation mPEG-PLLA-hydrazone-DTX was dissolved in 2 mL THF at the concentration of 17 mmol. mPEG-PDLA-S-S-DM1 with or without mPEG-PDLA was dissolved in 2 mL DMF at the concentration of 2.3 mmol for mPEG-PDLA-SS-DM1 and 13.5 mmol for mPEG-PDLA, respectively. After mixing of THF solution and DMF solution, the mixture was stirred at room temperature for 4 h and then was added into Di-PBS dropwise. After stirring 1 hour at room temperature in a fume hood to evaporate THF as much as possible, the mixture was transferred to dialysis membrane (cutoff 3.5K) to remove solvent by dialysis against PBS for two days. After filtering with a 450 nm filter, the size of the complex was characterized by dynamic light scattering (Zetasizer from Malvern Instruments, Malvern, UK). The methods used for concentration of DM1 and DTX in complex were the same as the ones used in the prodrug formulations. Reconstitution of freeze-dried powder from the solution of the complex was successful without the help of any lyoprotectant, and the concentration of DTX and DM1 in complex formulation is 6.63 mmol and 0.95 mmol, respectively.

In a second procedure, mPEG-PLLA-hydrazone-DTX was dissolved in 2 mL THF at the concentration of 17 mmol. mPEG-PDLA-S-S-DM1 with or without mPEG-PDLA was dissolved in 2 mL acetonitrile at the concentration of 2.3 mmol for mPEG-PDLA-DM1 and 10.5 mmol for mPEG-PDLA, respectively. After mixing of THE solution and acetonitrile solution, the mixture was stirred at room temperature for 4 h and then was added into Di-PBS dropwise. After stirring 1 hour at room temperature, the organic solvents were rotary evaporated under vacuum. After frozen-dry and reconstitution, the concentration of DTX and DM1 in complex is 7.79 mmol and 1.08 mmol, respectively.

Complex Containing Glucose Formulation Preparation mPEG-PLLA-hydrazone-DTX was dissolved in 2 mL THF at the concentration of 17 mmol. mPEG-PDLA-S-S-DM1 and Glu-PEG-PDLA were dissolved in 2 mL DMF at the concentration of 2.3 mmol for mPEG-PDLA-DM1 and 25 mmol for Glu-PEG-PDLA, respectively. After mixing of THE solution and DMF solution, the mixture was stirred at room temperature for 4 h and then was added into Di-PBS dropwise. After stirring 1 hour at room temperature and rotary evaporation under vacuum at room temperature to remove solvent as much as possible, the mixture was transferred to dialysis membrane (cutoff 3.5K) to remove the residual organic solvents by dialysis against PBS for two days. After filtering with a 450 nm filter, the size of the complex was characterized by dynamic light scattering (Zetasizer from Malvern Instruments, Malvern, UK). Reconstitution of freeze-dried powder from the solution of the complex containing glucose was successful without the help of any lyoprotectant, and the concentration of DTX and DM1 in complex formulation is 5.37 mmol and 0.745 mmol, respectively.

Example 3: In Vitro Release Test

The release of poly-DTX was performed by dialysis in phosphate buffer saline (pH 7.4 and 5.5, containing 0.2% w/v polysorbate 80). Briefly, 1 mL poly-DTX formulation with the concentration of docetaxel adjusted to 3 mg/mL with PBS was placed in a dialysis bag (MWCO=3.5k Da), which was sealed. After being immediately immersed in 10 mL release medium, the sample was incubated at 37° C. At scheduled time intervals (4, 8, 24, 48 h), 1 mL of the external release medium was taken out and replenished with an equal volume of fresh medium.

The cumulative release of DTX was measured indirectly by quantifying the content of benzoic acid (one stable final degradation product of DTX) by HPLC. In brief, the solution withdrawn from release medium was lyophilized, dissolved in 6M NaOH (0.25 mL) and incubated at 60° C. in a water bath overnight. Finally, 6M formic acid (0.25 mL) was added and the mixture was filtrated through a 0.45 μm PTFE filter for HPLC detection. The mobile phase consisted of ammonium acetate (20 mM) and methanol in 90:10 ratio. The column effluent was detected at 230 nm. A benzoic acid standard dissolved in methanol was used to prepare a calibration curve. The mass conversion ratio of DTX:benzoic acid is 6.62:1. The calibration curve of benzoic acid was calculated to have the equation Y=4.92334X−3.53882 (Y=peak area, X=DTX concentration; $r^2$=0.99976) for concentrations ranging from 6.62-132.4 μg/mL.

The release of poly-DM1 was performed by dialysis in phosphate buffered saline (pH 7.4, containing 0.2% w/v polysorbate 80) with or without 10 mM glutathione (GSH). Briefly, 1 mL of the poly-DM1 formulation with the concentration of DM1 adjusted to 0.5 mg/mL by PBS was placed in a dialysis bag (MWCO=3.5k Da), which was sealed. After being immediately immersed in 10 mL release medium, the sample was incubated at 37° C. At scheduled time intervals (4, 8, 24, 48 h), 1 mL of the external release medium was taken out and replenished with an equal volume of fresh medium. All released samples were freeze-dried and the amount of released DM1 was determined using HPLC measurements as described previously.

Example 4: Combination Index of DM1 and DTX

Figure 13:
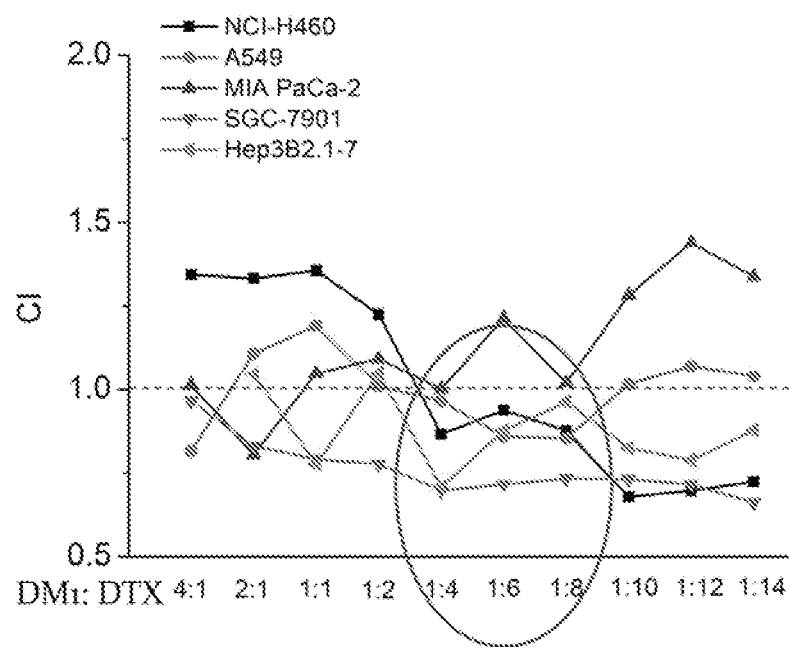
FIG. 13 shows the combination index (CI, displayed on the vertical axis) of free DM1 and DTX in different cell lines at different ratios of DM1 to DTX. CI is used for quantitative synergy determination of two-drug combinations. Synergism is represented by CI<1, an additive effect occurs when CI=1, and antagonism occurs when CI>1. Cell lines include A549 (adenocarcinoma human alveolar basal epithelia cells; red circles), NCI-H460 (non-small cell lung cancer cells; black squares), MiA PaCa-2 (pancreatic cancer cells, blue triangles), SGC-7901 (gastric cancer cells, teal triangles), and Hep3B2.1-7 (liver cancer cells, pink triangles).

Combination index was calculated for free DM1 and DTX in different cell lines at different ratios of DM1 to DTX. As used herein, "combination index" or "CI" refers quantitative determination of drug combinations. Results are categorized as synergism (condition CI<1), additive effect (condition CI=1), and antagonism (condition CI>1). Tests were conducted in Human adenocarcinoma alveolar basal epithelial cells (A549), non-small cell lung cancer cells (NCI-H460), pancreatic cancer cells (MiA PaCa-2), gastric cancer cells (SGC-7901), and liver cancer cells (Hep3B2.1-7). Combination index results for these five cell lines are shown in FIG. 13, with different drug ratios on the horizontal axis and combination index on the vertical axis.

Example 5: Dynamic Light Scattering to Determine Particle Size

Figures 14A, 14B, 14C:
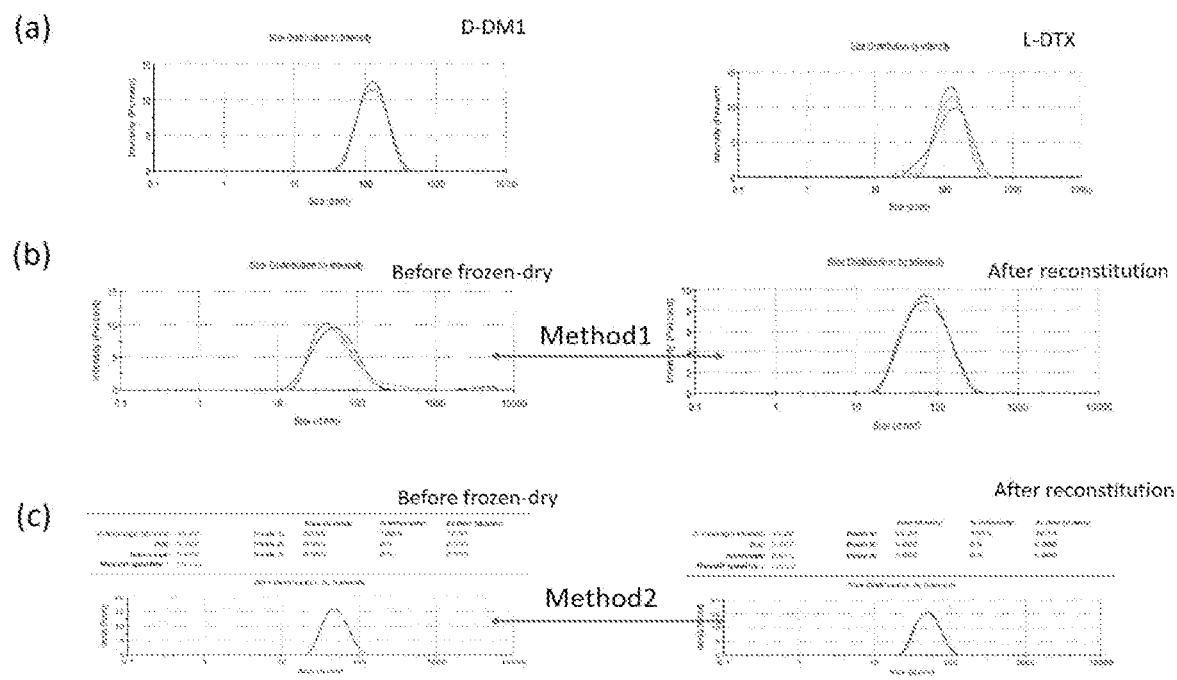
FIG. 14A shows particle sizes of prodrug mPEG-PDLA-SS-DM1(D-DM1) and mPEG-PLLA-hydrazone-DTX(L-DTX).
FIG. 14B shows the particle size of the complex formation produced by dialysis (left panel) and after freeze-drying and reconstitution (right panel).
FIG. 14C shows the particle size of the complex formation produced by using rotary evaporation (left panel) and after freeze-drying and reconstitution (right panel).

Particle sizes for the stereocomplexes and individual component molecules were determined using dynamic light scattering. FIG. 14A shows particle sizes of prodrug mPEG-PDLA-SS-DM1 and mPEG-PLLA-hydrazone-DTX. FIG. 14B shows the particle size of the complex formation produced by dialysis (left panel) and after freeze-drying and reconstitution (right panel). The size of the complex is about 80 nm. FIG. 14C shows the particle size of the complex formation produced by using rotary evaporation (left panel) and after freeze-drying and reconstitution (right panel). The size of the complex is about 50 nm.

Figures 15A, 15B:
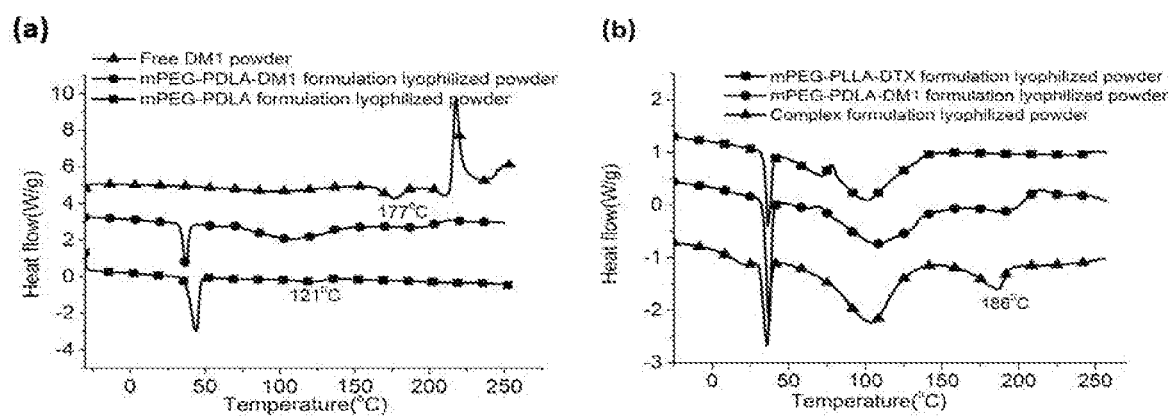
FIGS. 15A-15B show DSC results evaluating melting temperature (Tm) of the various formulations.

Example 6: Differential Scanning Calorimetry to Determine Melting Temperature Melting temperatures of prodrugs, precursor molecules and the stereocomplexes were determined using differential scanning calorimetry (DSC). DSC results are shown in FIGS. 15A-15B. FIG. 15A shows DSC profiles of free DM1 powder (blue line), mPEG-PDLA lyophilized powder (black line), and mPEG-PDLA-DM1 prodrug (red line). DM1 has a melting temperature of 177°C, while the PDLA has a melting temperature of about 120° C. FIG. 15B shows melting temperature profiles for prodrugs mPEG-PLLA-DTX (black line), mPEG-PDLA-DM1 (red line), and the stereocomplex formed between the two (blue line). A new melting temperature of 186° C. appears in the DSC profile for the stereocomplex, indicating a strong interaction between PDLA and PLLA during stereocomplexation.

Example 7: Release of DTX and DM1 Over Time

Figures 16A, 16B:
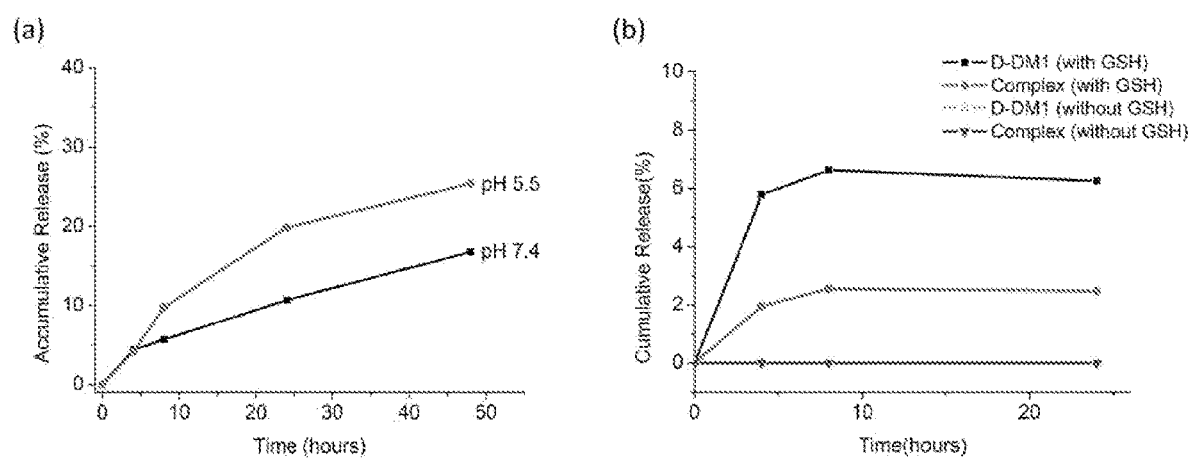
FIGS. 16A-16B show release of drugs from complexes over time.

Release of DTX from the stereocomplex over time was measured at pH 7.4 (squares) and 5.5 (circles); results are presented in FIG. 16A. Conjugation of DTX with the pH-sensitive hydrazone linker provides a faster release of DTX at pH 5.5 than at a pH of 7.4, which is closer to neutral.

Release of DM1 from the stereocomplex over time, with and without glutathione (GSH) was measured at pH 7.4; results are presented in FIG. 16B. DM1 is released from the isolated prodrug most quickly in the presence of GSH (squares) and more slowly from the stereocomplex (circles). In the absence of glutathione, DM1 is essentially not released from either the isolated prodrug or the complex (triangles and inverted triangles at 0% cumulative release). Thus, conjugation of DM1 with a redox-sensitive disulfide linker prohibits premature release of DM1 without GSH.

Example 8: Tolerance of Formulations in Mice without Tumors

Figures 17A, 17B:
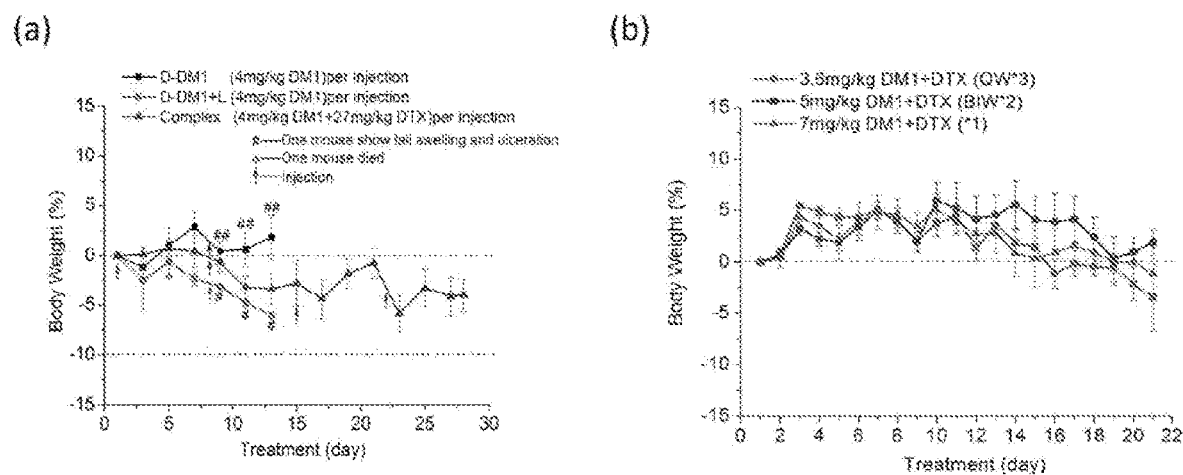
FIG. 17A shows the tolerance of the various formulations in mice without tumors with injections given at days 1, 8, 15, and 22.
FIG. 17B shows the body weight change of mice without tumors in three weeks after complex injections at 3.6 mg/kg DM1 once/week for three injections, at 5 mg/kg DM1 once/two weeks for two injections and at 7 mg/kg DM1 only one injection, respectively.

Healthy mice (n=5 for each treatment group) were injected on days 1, 8, 15, and 22 of a 28-day trial in the tail vein with either the DM1-containing prodrug at 4 mg/kg, the DM1-containing prodrug plus mPEG-PLLA at 4 mg/kg, or the stereocomplex with 4 mg/kg DM1 and 27 mg/kg DTX per injection and body weight was monitored to determine tolerance of the treatments. Body weight increased slightly, on average, with the DM1-containing prodrug, though two mice showed tail swelling and ulceration on days 8-14 (squares). One mouse in the prodrug plus PLLA treatment group died on day 4 and treatment of this group was stopped (circles). Body weight decreased slightly, on average, with stereocomplex treatment, but stayed under a 5% change. No tail swelling or ulceration was observed in the stereocomplex treatment group (triangles). Results are presented in FIG. 17A. Healthy mice (n=5 for each treatment group) were injected with complex at 3.6 mg/kg DM1 once/week for total three injections, at 5 mg/kg DM1 once/two weeks for total two injections and at 7 mg/kg DM1 only once, respectively. No obvious body weight lose were observed in all treatment group in a 21-day trail, as shown in FIG. 17B.

Example 9: Tumor Size for Treatment and Control Groups

Figures 18A, 18B, 18C, 18D:
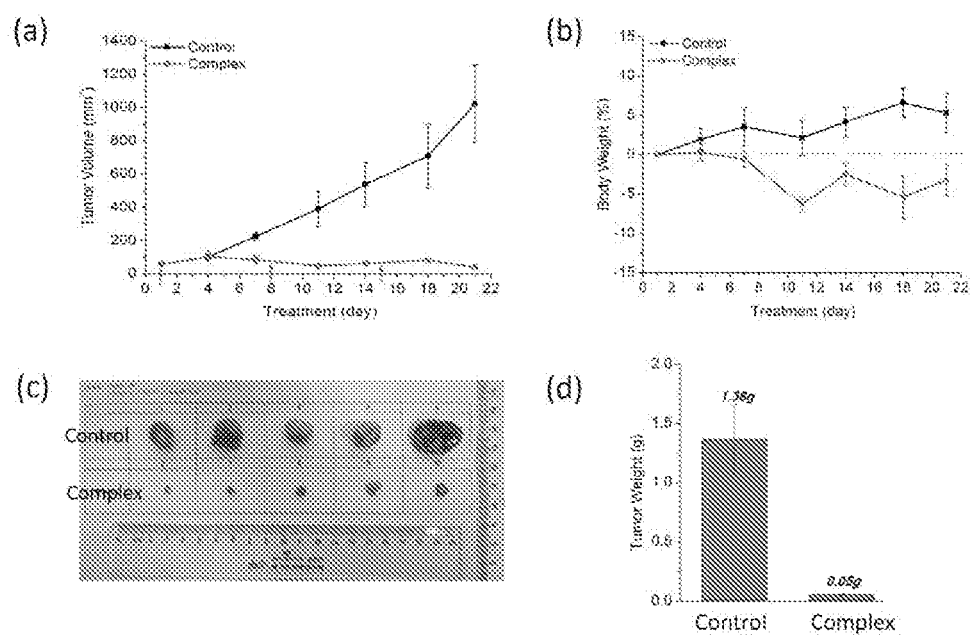
FIGS. 18A-18D show the in vivo antitumor efficacy of the complex in subcutaneous BGC-823 (gastric) tumor model via intravenous. Human gastric cancer cell suspensions were injected subcutaneously on the backs of mice to establish the tumor model. When tumor volume reached approximately 60 $mm^3$, groups of tumor-bearing mice (n=5) were injected with the through the tail vein on days indicated by the arrows in panel (a) with stereocomplex (i.e., days 1, 8, and 15 at a dosage of 4 mg/kg DM1 and 36 mg/kg DTX per injection).

Human gastric cancer cell suspensions (BGC-823) were injected subcutaneously on the backs of mice to establish the tumor model. When tumor volume reached approximately 60 mm$^3$, groups of tumor-bearing mice (n=5) were injected with the through the tail vein on days indicated by the arrows in panel (a) with stereocomplex (i.e., days 1, 8, and 15 at a dosage of 4 mg/kg DM1 and 36 mg/kg DTX per injection). FIG. 18A shows tumor size measurements for a control group (squares) and treatment groups (circles). No significant body weight loss was observed for the treatment group or the control group (FIG. 18B). Significant tumor reduction was achieved for the complex group (excised tumors are pictured in FIG. 18C), with a greater total reduction in tumor weight achieved in the stereocomplex treatment group (FIG. 18D).

Example 10: Antitumor Efficacy and Toxicity in a Pancreatic Tumor Model

Figures 19A, 19B:
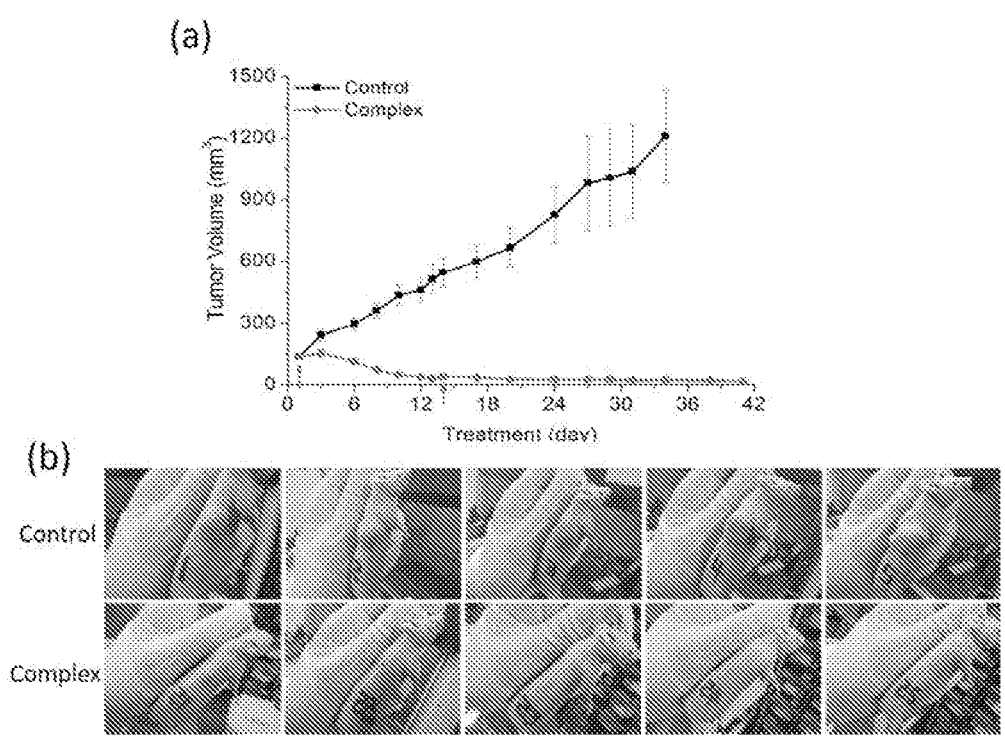
FIGS. 19A-19B show the in vivo antitumor efficacy of the complex in subcutaneous MIA PaCa-2 (pancreatic) tumor model via intravenous injection. Cell suspensions were injected subcutaneously on the backs of mice to establish the tumor model. When tumor volume reached approximately 140 $mm^3$, groups of tumor bearing mice (n=5) were injected with the complex through the tail vein once every two weeks. After two injections (i.e., days 1, and 14 at a dosage of 5 mg/kg DM1 and 40 mg/kg DTX per injection), one mouse was tumor-free on the 24th day, and in total three mice had no tumors by the 38th day.

In vivo antitumor efficacy of the complex was assessed in a subcutaneous MiA PaCa-2 pancreatic tumor model. MiA PaCa-2 cell suspensions were injected subcutaneously on the backs of mice to establish the tumor model. When tumor volume reached approximately 140 mm$^3$, groups of tumor bearing mice (n=5) were injected through the tail vein on day 1 and day 14 of an approximately 40-day trial. After 24 days, one treated mouse was tumor-free, and three total mice were tumor-free after 38 days. After tumor regression, no relapses were observed during the testing period. Tumor size change is presented in FIG. 19A and FIG. 19B shows photographs of the mice in the control group (top row) and treatment group (bottom row) on 29th day.

Example 11: Antitumor Efficacy Comparison in a Pancreatic Tumor Model

Figures 20A, 20B:
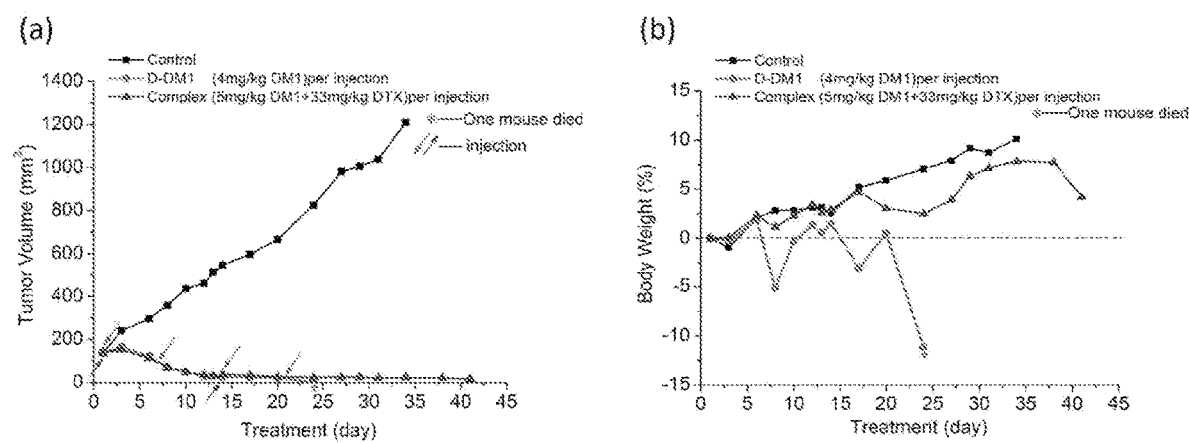
FIGS. 20A-20B shows a comparison between complex and prodrug for in vivo antitumor efficacy and toxicity in a subcutaneous MIA PaCa-2 when the treatment is delivered via intravenous injection. Cell suspensions were injected subcutaneously on the backs of mice to establish the tumor model. When tumor volume reached approximately 140 $mm^3$, groups of tumor bearing mice (n=5) were injected with the complex through the tail vein. After four injections of D-DM1 prodrug and two injections for the complex, approximately the same antitumor effects were observed (FIG. 20A, circles and triangles, respectively), but the prodrug treatment induced mouse death and obvious body weight decreases (FIG. 20B, circles), while the complex treatment group showed a body weight increase during the treatment period (FIG. 20B, triangles).

Antitumor efficacy and toxicity for the stereocomplex and DM1-containing prodrug were assessed in a subcutaneous MiaPaCa-2 pancreatic tumor model. MiA PaCa-2 cell suspensions were injected subcutaneously on the backs of mice to establish the tumor model. When tumor volume reached approximately 140 mm$^3$, groups of tumor-bearing mice (n=5) were injected with treatment through the tail vein. After four injections for the DM1-containing prodrug (D-DM1) and two injections for the stereocomplex, almost the same antitumor effect was observed. However, the D-DM1 treatment induced mouse death and obvious body weight decrease and this treatment group was ended after the 4th injection for humane reasons. Conversely, the stereocomplex treatment group shows a body weight increase during the whole period, indicating general safety of the treatment. Results are presented in FIGS. 20A-20B. FIG. 20A shows tumor volume for control group (squares), D-DM1 prodrug group (circles), and stereocomplex treatment group (triangles). FIG. 20B shows body weight for control group (squares), D-DM1 prodrug group (circles), and stereocomplex treatment group (triangles).

Example 12: Antitumor Efficacy and Toxicity in a Liver Tumor Model

Antitumor efficacy and toxicity for the stereocomplex was assessed in a subcutaneous Hep 3B2.1-7 liver tumor model. Hep 3B2.1-7 cell suspensions were injected subcutaneously on the backs of mice to establish the tumor model. When tumor volume reached approximately 130 mm$^3$, groups of tumor-bearing mice (n=5) were injected with a treatment through the tail vein. In this model, the control group's body weight decreased with tumor size increase. Body weight for the stereocomplex treatment group remained normal for the entire test period. After treatment, one mouse from the stereocomplex treatment group was tumor free and the average tumor weight of the stereocomplex treatment group (n=5) was only 4.5% of that of the control group (n=3), where two mice died before the end of the trial due to the formation of very large tumors.

Figures 21A, 21B, 21C, 21D:
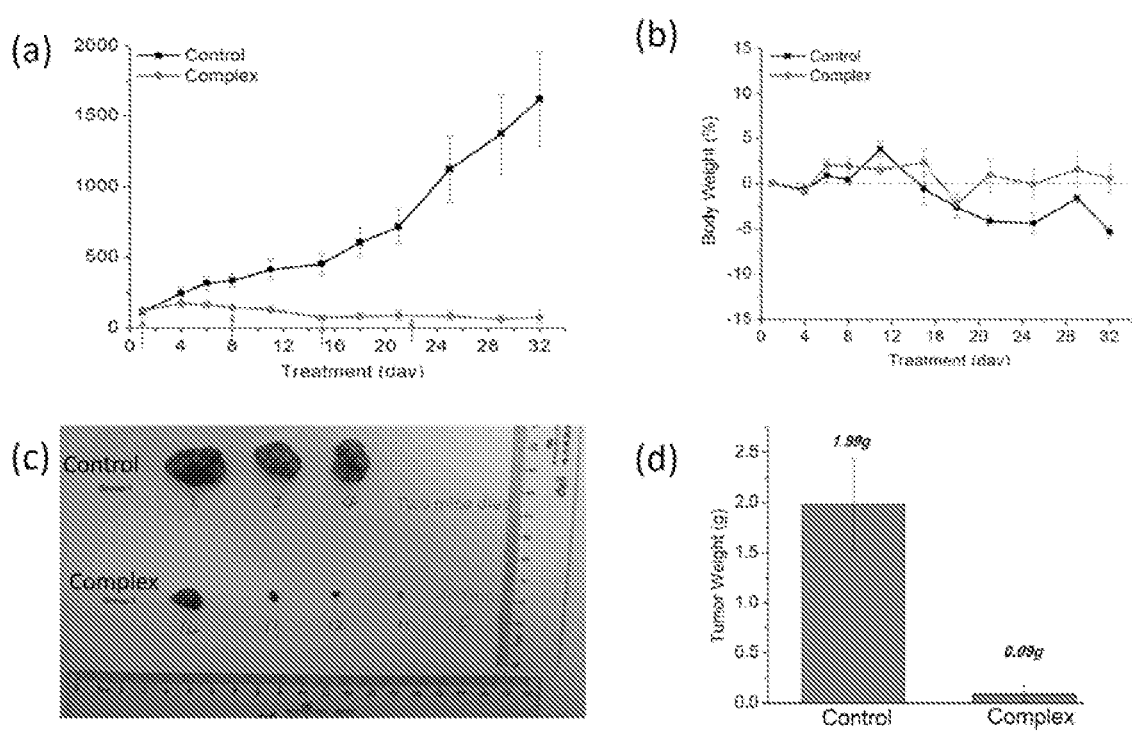
FIGS. 21A-21D show a comparison between complex and control (no complex administration) in vivo antitumor efficacy and toxicity in a subcutaneous Hep 3B2.1-7 (liver) tumor model when the treatment is delivered via intravenous injection. Cell suspensions were injected subcutaneously on the backs of mice to establish the tumor model. When tumor volume reached approximately 130 $mm^3$, groups of tumor bearing mice (n=5) were injected with the complex through the tail vein.

Results are presented in FIGS. 21A-21D. FIG. 21A shows tumor volume for control group (squares) and stereocomplex treatment group (circles), arrows indicate injection dates for treatment group at a dosage of 4 mg/kg DM1 and 28 mg/kg DTX per injection. FIG. 21B shows body weight for control group (squares) and stereocomplex treatment group (circles). FIG. 21C shows excised tumors for the control group (top row) and stereocomplex treatment group (bottom row). FIG. 21D shows tumor weight comparison of the control group (left) and stereocomplex treatment group (right).

Example 13: Antitumor Efficacy and Toxicity in a Colon Tumor Model

Figures 22A, 22B, 22C, 22D:
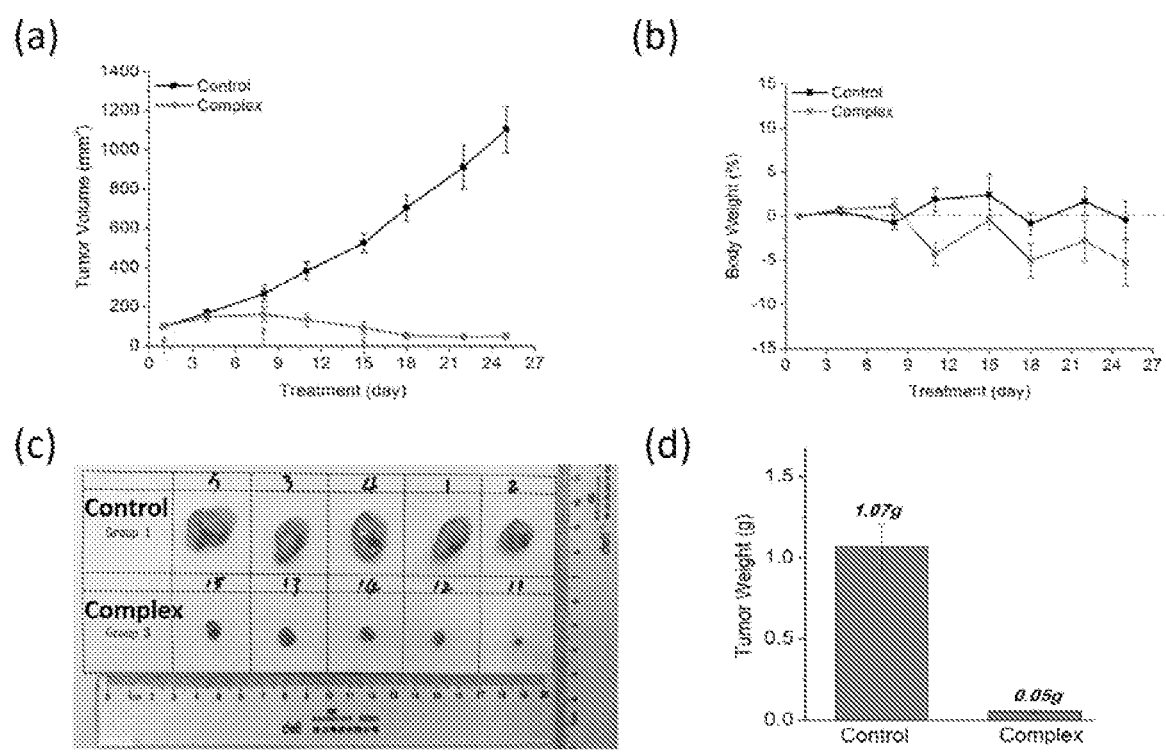
FIGS. 22A-22D show tumor size changes for complex treatment group versus a control group in a subcutaneous HT-29 (colon) tumor model. Cell suspensions were injected subcutaneously on the backs of mice to establish the tumor model and when tumors were approximately 100 $mm^3$, groups of tumor bearing mice (n=5) were injected with the compositions through the tail vein.

Antitumor efficacy and toxicity for the stereocomplex was assessed in a subcutaneous HT-29 colon tumor model. Cell suspensions were injected subcutaneously on the backs of mice to establish the tumor model and when tumors were approximately 100 mm$^3$, groups of tumor bearing mice (n=5) were injected with the compositions through the tail vein. FIG. 22A shows that tumor volume increased significantly more with untreated mice (squares), while mice treated with the complex (circles) exhibited lower final tumor volumes (with arrows indicating injection dates at a dosage of 4 mg/kg DM1 and 32 mg/kg DTX per injection). FIG. 22B shows the change of body weight for control group and treatment group. FIG. 22C shows excised tumors for the control group (top row) and stereocomplex treatment group (bottom row). FIG. 22D shows tumor weight comparison of the control group (left) and stereocomplex treatment group (right).

Example 14: Antitumor Efficacy Comparison in a Nasopharyngeal Tumor Model

Figure 23:
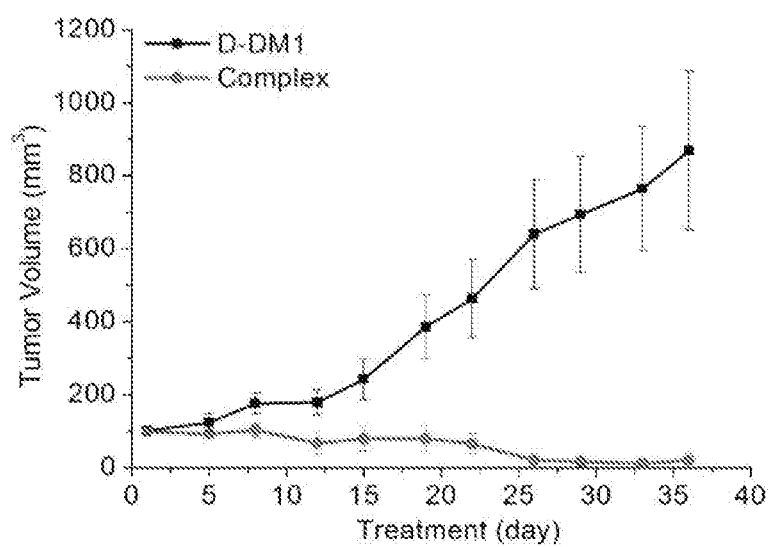
FIG. 23 shows a comparison between complex and prodrug (D-DM1) for in vivo antitumor efficacy in a subcutaneous CNE (nasopharyngeal) tumor model when the treatment is delivered via intravenous injection. Cell suspensions were injected subcutaneously on the backs of mice to establish the tumor model. When tumor volume reached approximately 100 mm$^3$, groups of tumor bearing mice (n=5) were injected with the complex through the tail vein. As shown, with the equivalent DM1 dose, tumor volume continued to grow for the prodrug group (squares) but complex treatment showed good tumor growth inhibition efficacy (circles).

Antitumor efficacy and toxicity for the stereocomplex and DM1-containing prodrug were assessed in a subcutaneous CNE nasopharyngeal tumor model when the treatment is delivered via intravenous injection. Cell suspensions were injected subcutaneously on the backs of mice to establish the tumor model. When tumor volume reached approximately 100 mm$^3$, groups of tumor bearing mice (n=5) were injected with the complex through the tail vein. FIG. 23 shows that tumor volume increased significantly with D-DM1 prodrug treatment group after four injections at 4 mg/kg DM1 once per week, while mice treated with the complex exhibited lower final tumor volume after four injections at 4 mg/kg DM1 and 26 mg/kg DTX once per week.

Example 15: Antitumor Efficacy and Toxicity in a Small Cell Lung Tumor Model In vivo antitumor efficacy of the complex was assessed in a subcutaneous NCI-H526 small cell lung tumor model.

Figures 24A, 24B:
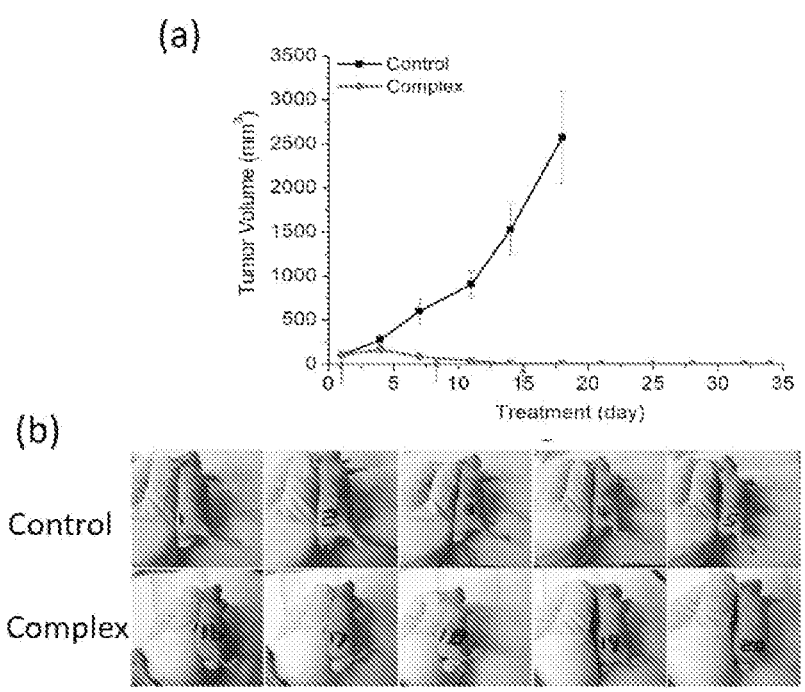
FIGS. 24A-24B show the in vivo antitumor efficacy of the complex in subcutaneous NCI-H526 (small-cell lung cancer) tumor model via intravenous injection. Cell suspensions were injected subcutaneously on the backs of mice to establish the tumor model. When tumor volume reached approximately 100 mm$^3$, groups of tumor bearing mice (n=5) were injected with the complex through the tail vein once every week. After three injections, one mouse was tumor-free on the 18th day, and all mice had no tumors by the 32$^{nd}$ day.

NCI-H526 cell suspensions were injected subcutaneously on the backs of mice to establish the tumor model. When tumor volume reached approximately 100 mm³, groups of tumor bearing mice (n=5) were injected through the tail vein once every week. After three injections at 3.8 mg/kg DM1 and 32 mg/kg DTX once per week, one mouse was tumor-free on the 18th day, and all mice had no tumors from the 32$^{nd}$ day. FIG. 24A shows tumor size change for the group treated with complex (red line) versus the control group (black line). FIG. 24B shows control mice (top row of photos) and treated mice (bottom row of photos) on the 18th day of the trial.

Figures 25A, 25B, 25C, 25D:
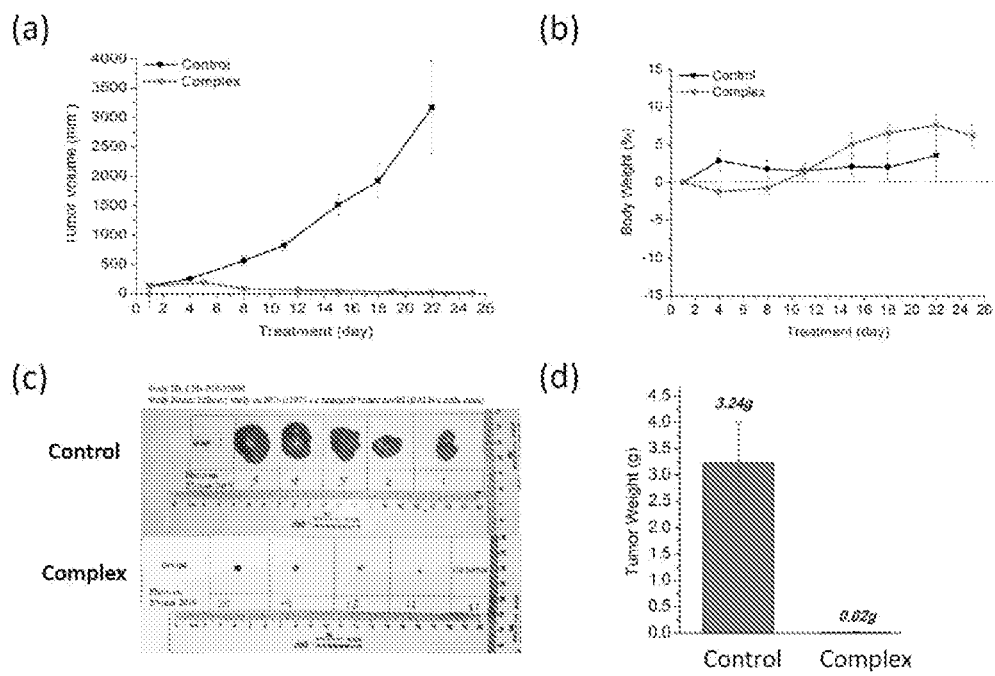
FIGS. 25A-25D show the in vivo antitumor efficacy of the complex in subcutaneous NCI-H1975 (non-small cell lung cancer) tumor model via intravenous injection. Cell suspensions were injected subcutaneously on the backs of mice to establish the tumor model and when tumors were approximately 130 mm$^3$, groups of tumor bearing mice (n=5) were injected with the compositions through the tail vein.

Example 16: Antitumor Efficacy and Toxicity in a Non-Small Cell Lung Tumor Model In vivo antitumor efficacy of the complex was assessed in a subcutaneous NCI-H1975 non-small cell lung tumor model. Cell suspensions were injected subcutaneously on the backs of mice to establish the tumor model and when tumors were approximately 130 mm³, groups of tumor bearing mice (n=5) were injected with the compositions through the tail vein. FIG. 25A shows that tumor volume increased significantly more with untreated mice (black line), while mice treated with the complex (red line) exhibited lower final tumor volumes after only one injection at 5 mg/kg DM1 and 33 mg/kg DTX. FIG. 25B shows the change of body weight for control group and treatment group. FIG. 25C shows excised tumors for the control group (top row) and stereocomplex treatment group (bottom row), notably, one mouse had no tumor at the end of the trial in the treatment group. FIG. 25D shows tumor weight comparison of the control group (left) and stereocomplex treatment group (right).

Figures 26A, 26B, 26C, 26D:
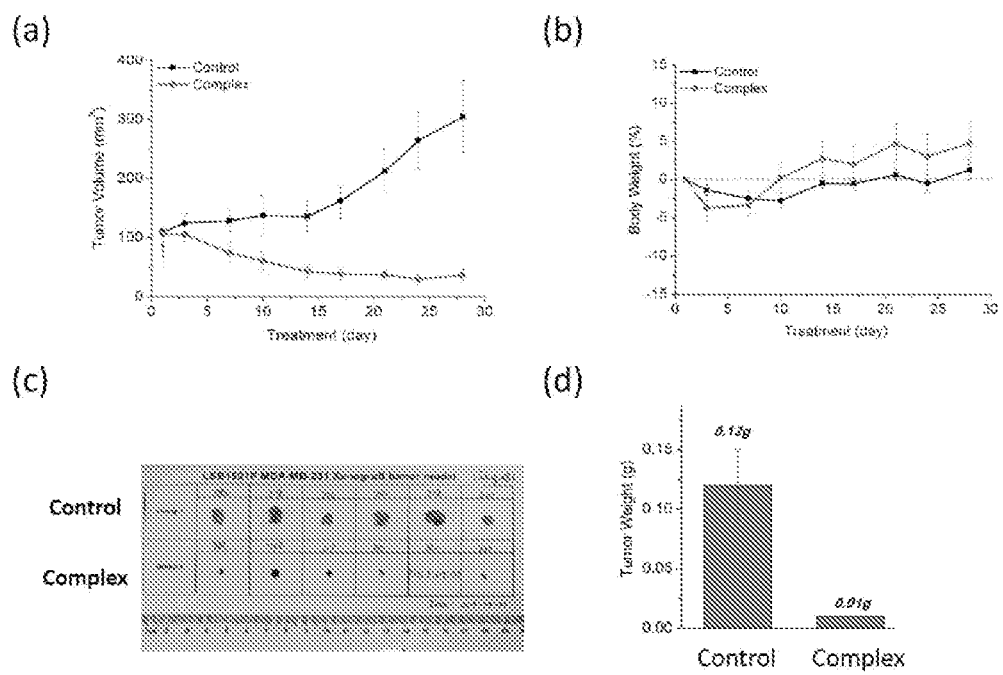
FIGS. 26A-26D show the in vivo antitumor efficacy of the complex in subcutaneous MDA-MB-231 (triple negative breast cancer) tumor model. Cell suspensions were injected subcutaneously on the backs of mice to establish the tumor model and when tumors were approximately 100 mm$^3$, groups of tumor bearing mice (n=6) were injected with the compositions through the tail vein.

Example 17: Antitumor Efficacy and Toxicity in a Triple-Negative Breast Tumor Model In vivo antitumor efficacy of the complex was assessed in a subcutaneous MDA-MB-231 triple negative breast tumor model. Cell suspensions were injected subcutaneously on the backs of mice to establish the tumor model and when tumors were approximately 100 mm³, groups of tumor bearing mice (n=6) were injected with the compositions through the tail vein. FIG. 26A shows that tumor volume increased significantly more with untreated mice (squares), while mice treated with the complex (circles) exhibited lower final tumor volumes after only one injection at 2.5 mg/kg DM1 and 18 mg/kg DTX. FIG. 26B shows the change of body weight for control group and treatment group. FIG. 26C shows excised tumors for the control group (top row) and stereocomplex treatment group (bottom row), notably, one mouse was tumor-free from the 23$^{rd}$ day to the end of the trial. FIG. 26D shows the tumor weight comparison of the control group (left) and stereocomplex treatment group (right).

Example 18: Antitumor Efficacy and Toxicity in a Breast Tumor Model

Figures 27A, 27B:
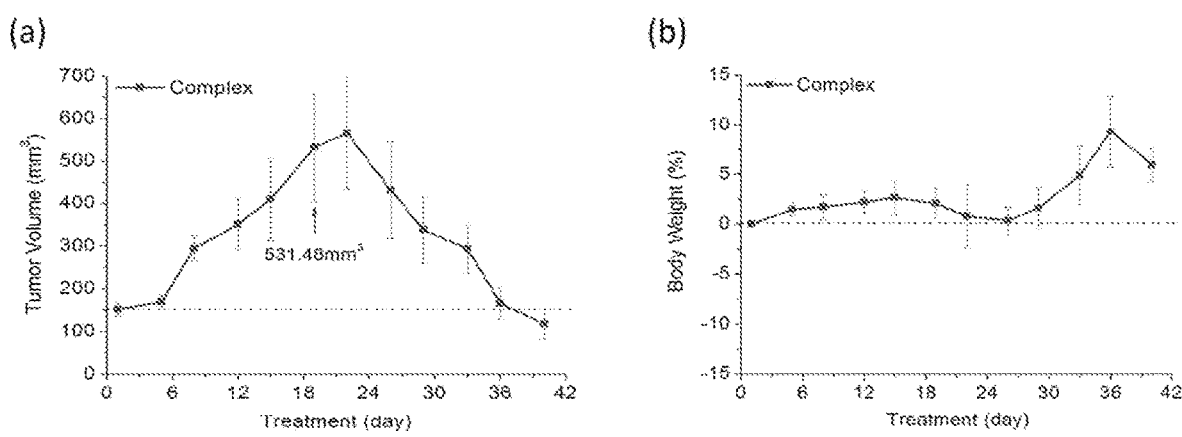
FIGS. 27A-27B show the in vivo antitumor efficacy of the complex in subcutaneous MX-1 (breast) tumor model via intravenous injection. Cell suspensions were injected subcutaneously on the backs of mice to establish the tumor model. When tumor volume reached approximately 530 mm$^3$, groups of tumor bearing mice (n=5) were injected with the complex through the tail vein. After only one injection, tumor size decreased continuously in the next 20 days, as shown in FIG. 27A, which demonstrated the efficacy of complex even in large tumors. No body weight loss was observed for this treatment (FIG. 27B).

In vivo antitumor efficacy of the complex in large tumors was assessed in a subcutaneous MX-1 breast tumor model. Cell suspensions were injected subcutaneously on the backs of mice to establish the tumor model. When tumor volume reached approximately 530 mm³, groups of tumor bearing mice (n=5) were injected with the complex through the tail vein. After only one injection at 6 mg/kg DM1 and 42 mg/kg DTX, tumor size decreased continuously in the next 20 days, as shown in FIG. 27A, which demonstrated the efficacy of complex even in large tumors. No body weight loss was observed for this treatment (FIG. 27B).

Example 19: Antitumor Efficacy and Toxicity in a Breast Tumor Model

Figures 28A, 28B, 28C, 28D:
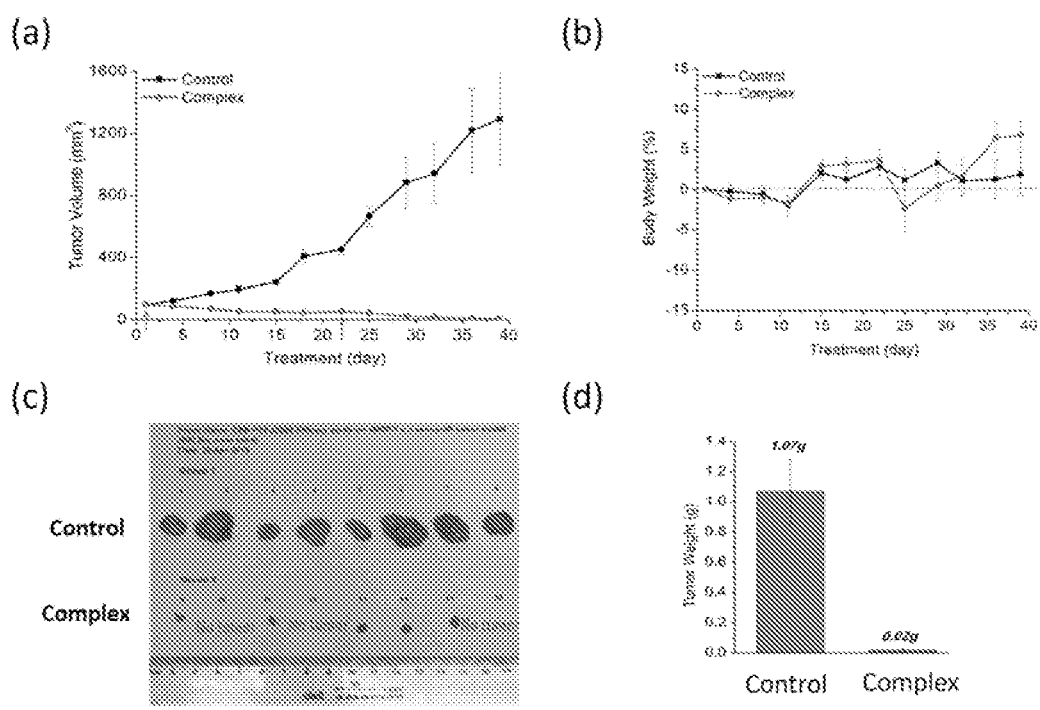
FIGS. 28A-28D show the in vivo antitumor efficacy of the complex in subcutaneous MCF-7 (breast) tumor model. Cell suspensions were injected subcutaneously on the backs of mice to establish the tumor model and when tumors were approximately 100 mm$^3$, groups of tumor bearing mice (n=8) were injected with the compositions through the tail vein.

In vivo antitumor efficacy of the complex was assessed in a subcutaneous MCF-7 breast tumor model. Cell suspensions were injected subcutaneously on the backs of mice to establish the tumor model and when tumors were approximately 100 mm³, groups of tumor bearing mice (n=8) were injected with the compositions through the tail vein. FIG. 28A shows the tumor volume change for the untreated group (black line) and the treatment one with the complex (red line) after two injections (with arrows indicating injection dates at 5 mg/kg DM1 and 30 mg/kg DTX each injection). FIG. 28B shows no difference of body weight change between the control group and treatment group. FIG. 28C shows excised tumors for the control group (top row) and stereocomplex treatment group (bottom row), notably, one mouse was tumor-free from the 25$^{th}$ day, and three mice were tumor-free at the end of the test. FIG. 28D shows the tumor weight comparison of the control group (left) and stereocomplex treatment group (right).

Example 20: Antitumor Efficacy and Toxicity in a Bladder Tumor Model

Figure 29A:
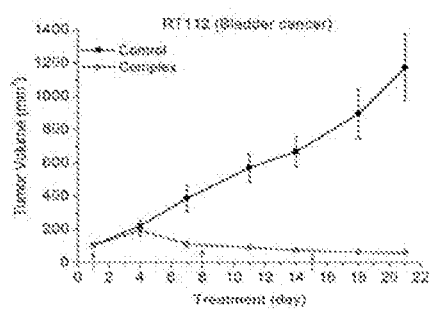
FIGS. 29A-29D show the in vivo antitumor efficacy of the complex in subcutaneous RT112 (bladder) tumor model. Cell suspensions were injected subcutaneously on the backs of mice to establish the tumor model and when tumors were approximately 100 mm$^3$, groups of tumor bearing mice (n=5) were injected with the compositions through the tail vein.
Figure 29B:
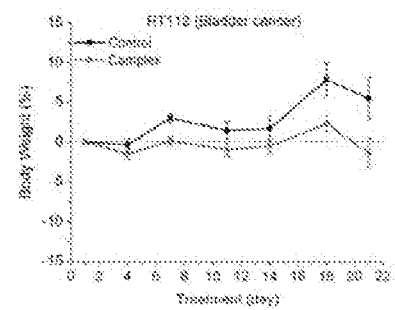
Figure 29C:
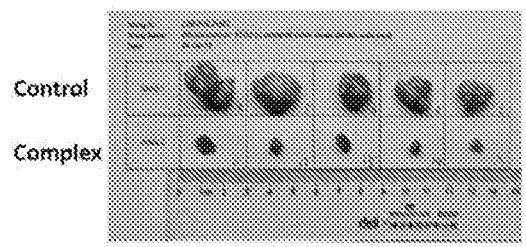
Figure 29D:
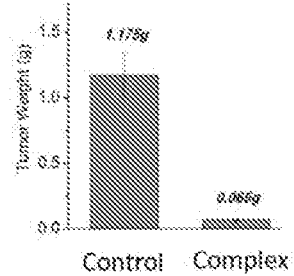

In vivo antitumor efficacy of the complex was assessed in a subcutaneous RT112 bladder tumor model. Cell suspensions were injected subcutaneously on the backs of mice to establish the tumor model and when tumors were approximately 100 mm³, groups of tumor bearing mice (n=5) were injected with the compositions through the tail vein. FIG. 29A shows that tumor volume increased significantly more with untreated mice (squares), while mice treated with the complex (circles) exhibited lower final tumor volumes after three injections at 3.6 mg/kg DM1 and 30 mg/kg DTX once per week. FIG. 29B shows the change of body weight for the control group and treatment group. FIG. 29C shows excised tumors for the control group (top row) and the stereocomplex treatment group (bottom row). FIG. 29D shows the tumor weight comparison of the control group (left) and stereocomplex treatment group (right).

Example 21: Antitumor Efficacy and Toxicity in an Esophagus Tumor Model

Figures 30A, 30B, 30C, 30D:
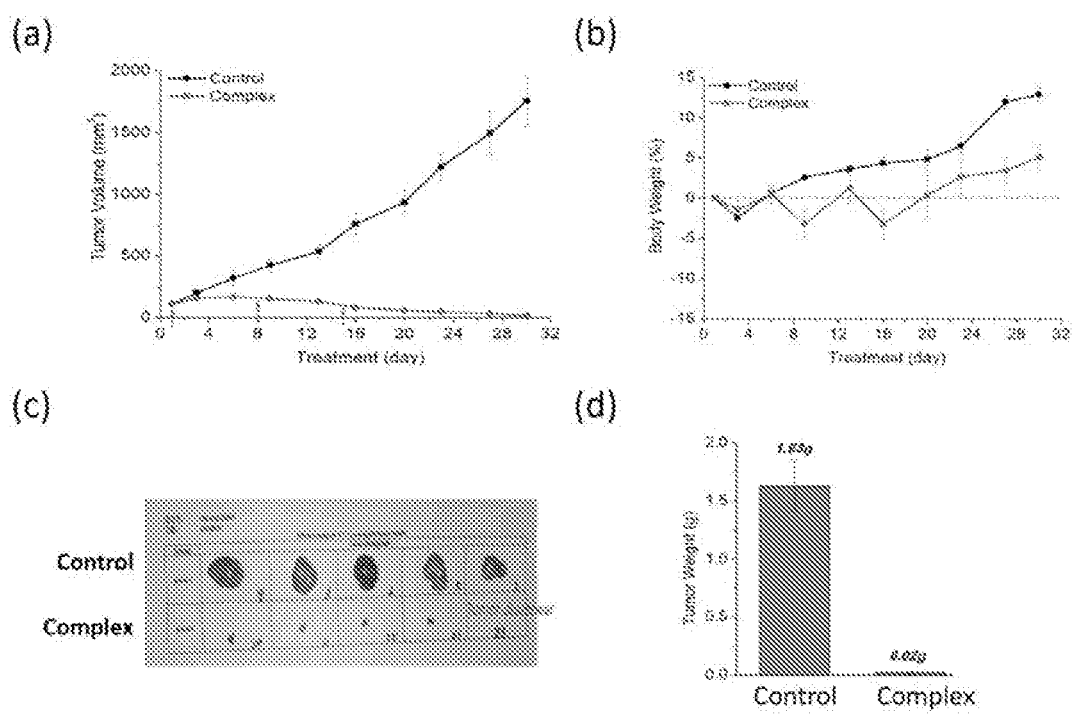
FIGS. 30A-30D show the in vivo antitumor efficacy of the complex in subcutaneous T.T (esophagus) tumor model. Cell suspensions were injected subcutaneously on the backs of mice to establish the tumor model and when tumors were approximately 110 mm$^3$, groups of tumor bearing mice (n=5) were injected with the compositions through the tail vein.

In vivo antitumor efficacy of the complex was assessed in a subcutaneous T.T esophagus tumor model. Cell suspensions were injected subcutaneously on the backs of mice to establish the tumor model and when tumors were approximately 110 mm³, groups of tumor bearing mice (n=5) were injected with the compositions through the tail vein. FIG. 30A shows that tumor volume increased significantly with untreated mice (squares), while tumor shrinked quickly with complex treated mice after three injections at 4 mg/kg DM1 and 40 mg/kg DTX once per week. FIG. 30B shows the change of body weight for the control group and treatment group. FIG. 30C shows excised tumors for the control group (top row) and stereocomplex treatment group (bottom row), notably, one mouse was tumor-free from the 27th day. FIG. 30D shows the tumor weight comparison of the control group (left) and the stereocomplex treatment group (right).

Example 22: Antitumor Efficacy and Toxicity in a Glioblastoma Tumor Model

Figures 31A, 31B, 31C, 31D:
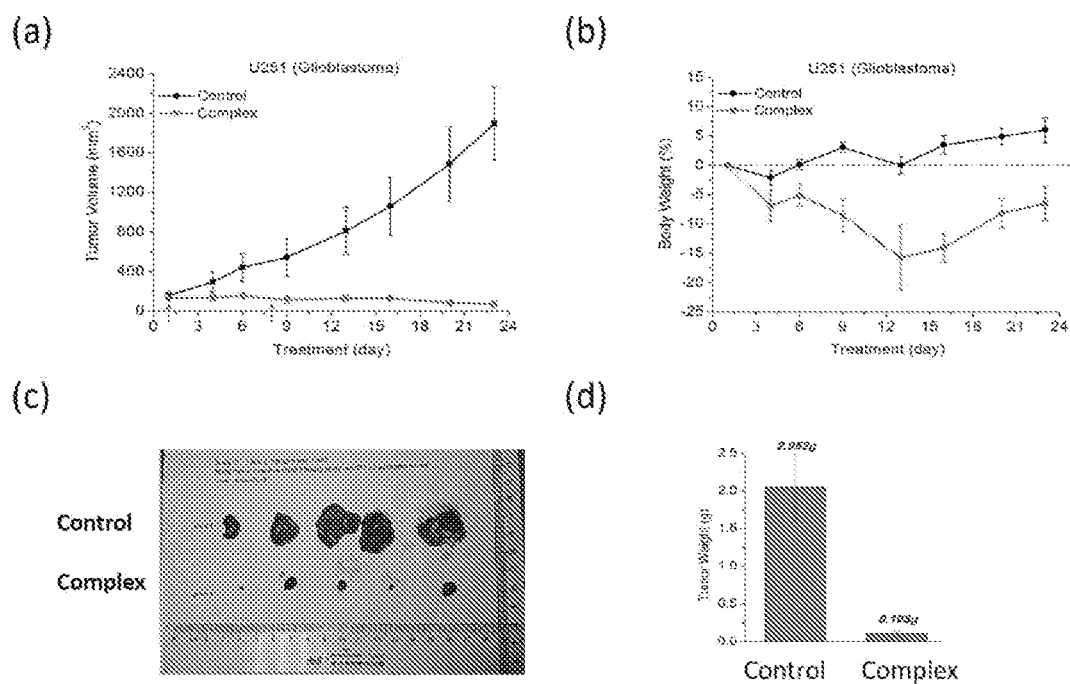
FIGS. 31A-31D show the in vivo antitumor efficacy of the complex in subcutaneous U251 (glioblastoma) tumor model. Cell suspensions were injected subcutaneously on the backs of mice to establish the tumor model and when tumors were approximately 150 mm$^3$, groups of tumor bearing mice (n=5) were injected with the compositions through the tail vein.

In vivo antitumor efficacy of the complex was assessed in a subcutaneous U251 globlastoma tumor model. Cell suspensions were injected subcutaneously on the backs of mice to establish the tumor model and when tumors were approximately 150 mm$^3$, groups of tumor bearing mice (n=5) were injected with the compositions through the tail vein. FIG. 31A shows that tumor volume increased significantly with untreated mice (squares), while mice treated with the complex (circles) exhibited lower final tumor volumes after two injections at 3 mg/kg DM1 and 30 mg/kg DTX once per week. FIG. 31B shows the change of body weight for the control group and treatment group. FIG. 31C shows excised tumors for the control group (top row) and the stereocomplex treatment group (bottom row). FIG. 31D shows the tumor weight comparison of the control group (left) and stereocomplex treatment group (right).

Example 23: Antitumor Efficacy and Toxicity in a Kidney Tumor Model

Figures 32A, 32B, 32C, 32D:
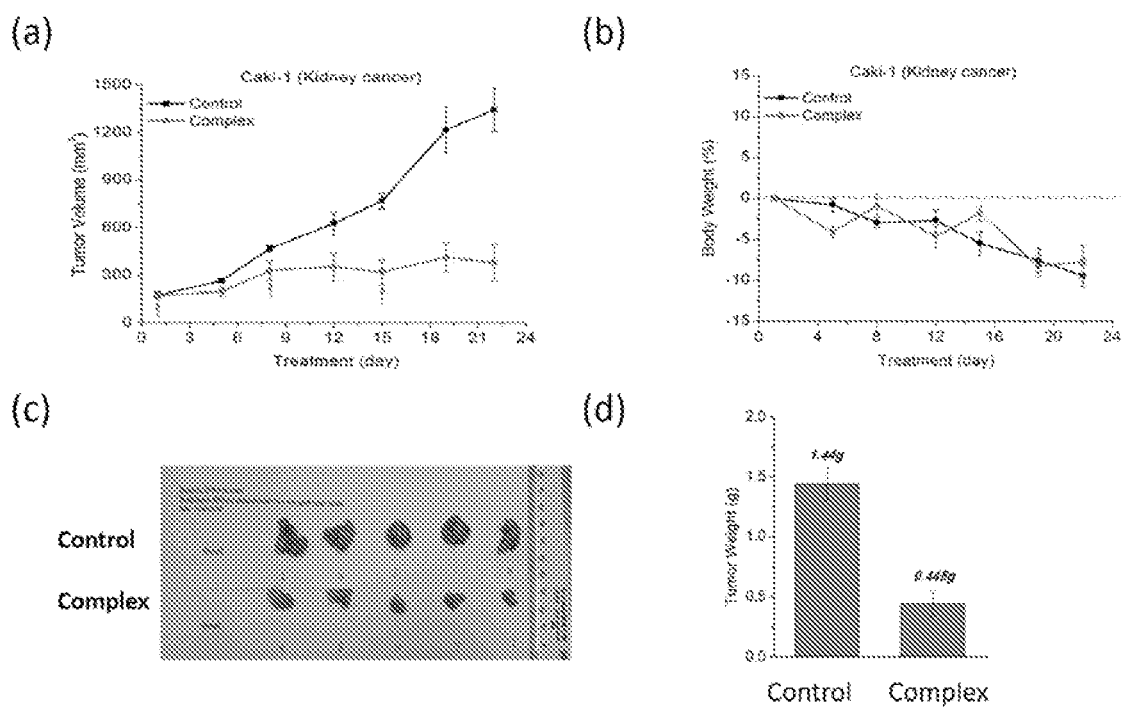
FIGS. 32A-32D show the in vivo antitumor efficacy of the complex in subcutaneous Caki-1(kidney) tumor model. Cell suspensions were injected subcutaneously on the backs of mice to establish the tumor model and when tumors were approximately 170 mm$^3$, groups of tumor bearing mice (n=5) were injected with the compositions through the tail vein.

In vivo antitumor efficacy of the complex was assessed in a subcutaneous Caki-1 kidney tumor model. Cell suspensions were injected subcutaneously on the backs of mice to establish the tumor model and when tumors were approximately 170 mm$^3$, groups of tumor bearing mice (n=5) were injected with the compositions through the tail vein. FIG. 32A shows that tumor volume increased significantly more with untreated mice (squares), while mice treated with the complex (circles) exhibited lower final tumor volumes after three injections at 3.2 mg/kg DM1 and 32 mg/kg DTX once per week. FIG. 32B shows the change of body weight for the control group and treatment group. FIG. 32C shows excised tumors for the control group (top row) and the stereocomplex treatment group (bottom row). FIG. 32D shows the tumor weight comparison of the control group (left) and stereocomplex treatment group (right).

Figures 33A, 33B, 33C, 33D:
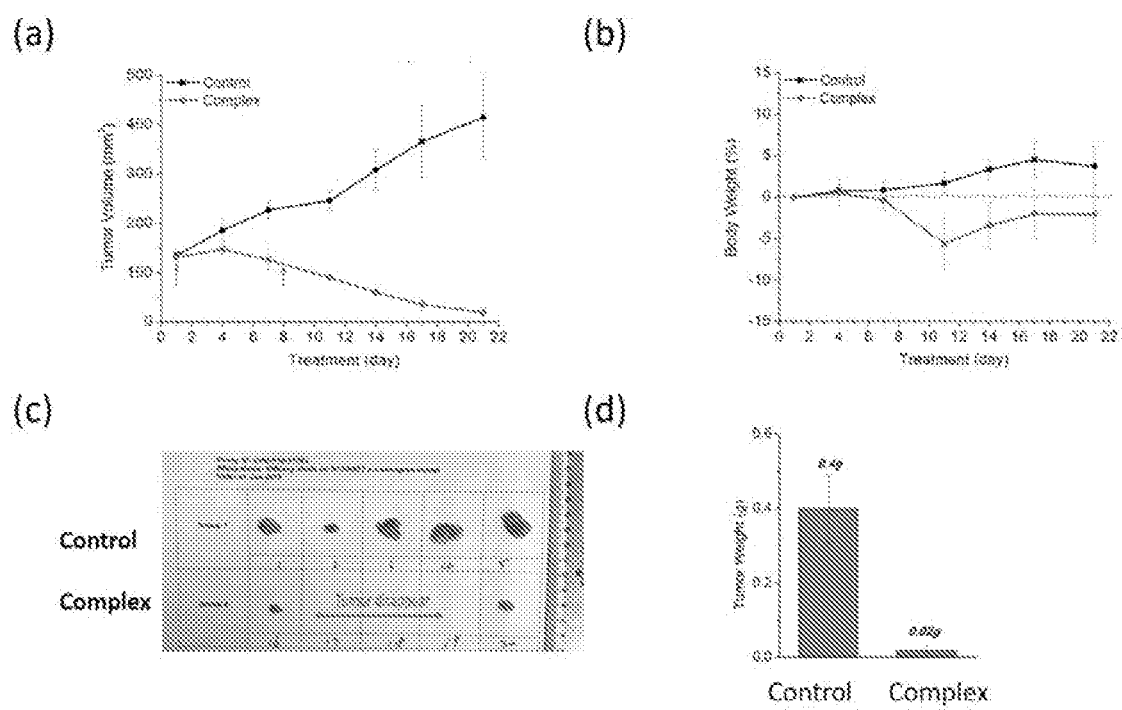
FIGS. 33A-33D show the in vivo antitumor efficacy of the complex in subcutaneous NCI-H522 (Non-small cell lung cancer) tumor model. Cell suspensions were injected subcutaneously on the backs of mice to establish the tumor model and when tumors were approximately 130 mm$^3$, groups of tumor bearing mice (n=5) were injected with the compositions through the tail vein.

Example 24: Antitumor Efficacy and Toxicity in a Non-Small Cell Lung Tumor Model In vivo antitumor efficacy of the complex was assessed in a subcutaneous NCI-H522 non-small cell lung tumor model. Cell suspensions were injected subcutaneously on the backs of mice to establish the tumor model and when tumors were approximately 130 mm$^3$, groups of tumor bearing mice (n=5) were injected with the compositions through the tail vein. FIG. 33A shows that tumor volume increased significantly with untreated mice (squares), while the tumor volume fell sharply with complex treated mice after two injections at 5 mg/kg DM1 and 50 mg/kg DTX once per week. FIG. 33B shows the change of body weight for the control group and treatment group. FIG. 33C shows excised tumors for the control group (top row) and stereocomplex treatment group (bottom row), notably, three mice were tumor-free at the end of the test. FIG. 33D shows the tumor weight comparison of the control group (left) and stereocomplex treatment group (right).

Figures 34A, 34B, 34C, 34D:
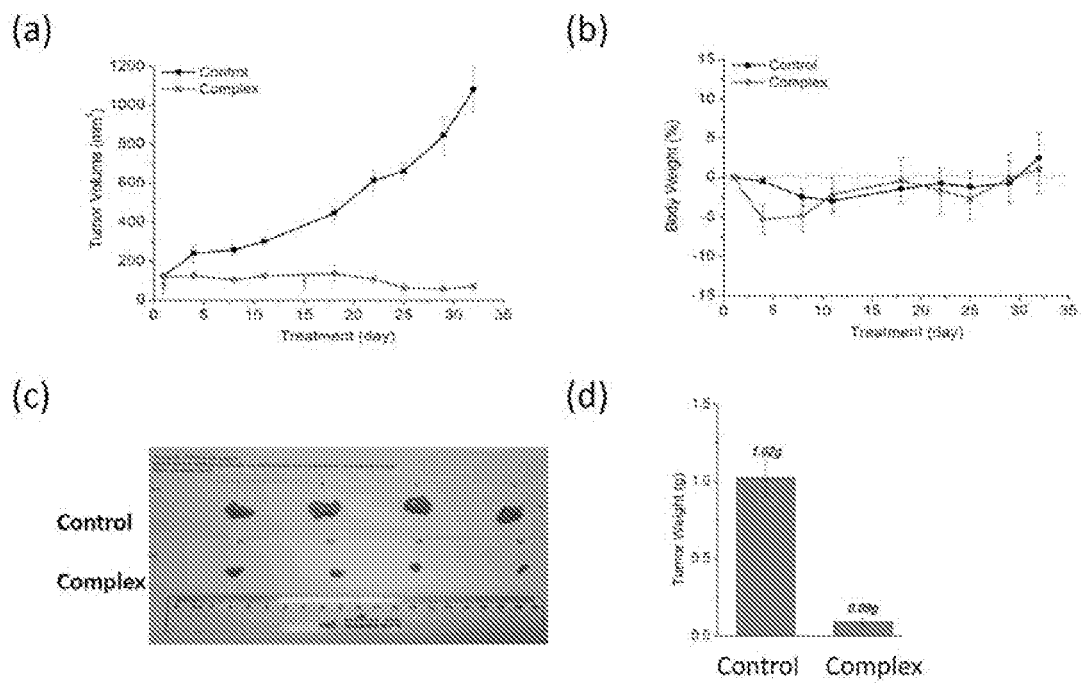
FIGS. 34A-34D show the in vivo antitumor efficacy of the complex in subcutaneous NCI-H226 (Non-small cell lung cancer) tumor model. Cell suspensions were injected subcutaneously on the backs of mice to establish the tumor model and when tumors were approximately 120 mm$^3$, groups of tumor bearing mice (n=4) were injected with the compositions through the tail vein.

Example 25: Antitumor Efficacy and Toxicity in a Non-Small Cell Lung Tumor Model In vivo antitumor efficacy of the complex was assessed in a subcutaneous NCI-H226 non-small cell lung tumor model. Cell suspensions were injected subcutaneously on the backs of mice to establish the tumor model and when tumors were approximately 120 mm$^3$, groups of tumor bearing mice (n=4) were injected with the compositions through the tail vein. FIG. 34A shows that tumor volume increased significantly more with untreated mice (squares), while mice treated with the complex (circles) exhibited lower final tumor volumes after two injections at 4 mg/kg DM1 and 32 mg/kg DTX once per two weeks. FIG. 34B shows the change of body weight for the control group and treatment group. FIG. 34C shows excised tumors for the control group (top row) and the stereocomplex treatment group (bottom row). FIG. 34D shows the tumor weight comparison of the control group (left) and stereocomplex treatment group (right).

Example 26: Antitumor Efficacy and Toxicity in a Ovarian Tumor Model

Figures 35A, 35B, 35C, 35D:
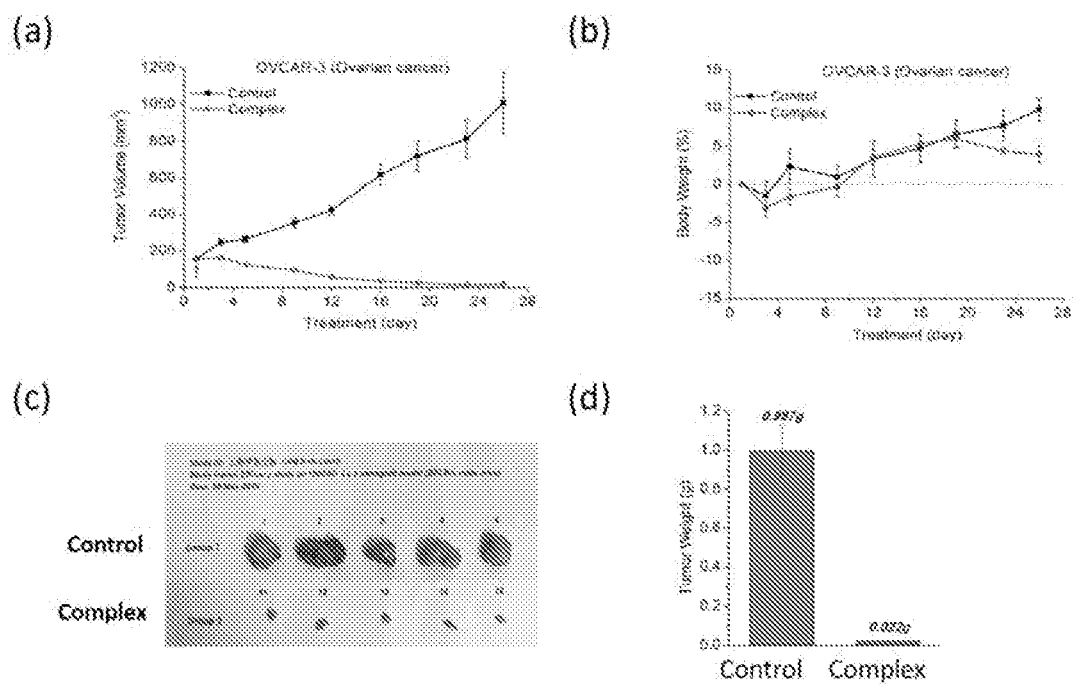
FIGS. 35A-35D show the in vivo antitumor efficacy of the complex in subcutaneous Ovcar-3 (Ovarian) tumor model. Cell suspensions were injected subcutaneously on the backs of mice to establish the tumor model and when tumors were approximately 150 mm$^3$, groups of tumor bearing mice (n=5) were injected with the compositions through the tail vein.

In vivo antitumor efficacy of the complex was assessed in a subcutaneous ovcar-3 ovarian tumor model. Cell suspensions were injected subcutaneously on the backs of mice to establish the tumor model and when tumors were approximately 150 mm$^3$, groups of tumor bearing mice (n=5) were injected with the compositions through the tail vein. FIG. 35A shows that tumor volume increased significantly with untreated mice (squares), while mice treated with the complex (circles) exhibited small final tumor volumes after only one injection at 6 mg/kg DM1 and 39 mg/kg DTX. FIG. 35B shows the change of body weight for the control group and treatment group. FIG. 35C shows excised tumors for the control group (top row) and the stereocomplex treatment group (bottom row). FIG. 35D shows tumor weight comparison of the control group (left) and stereocomplex treatment group (right).

Example 27: Antitumor Efficacy and Toxicity in a Prostate Tumor Model

Figures 36A, 36B, 36C, 36D:
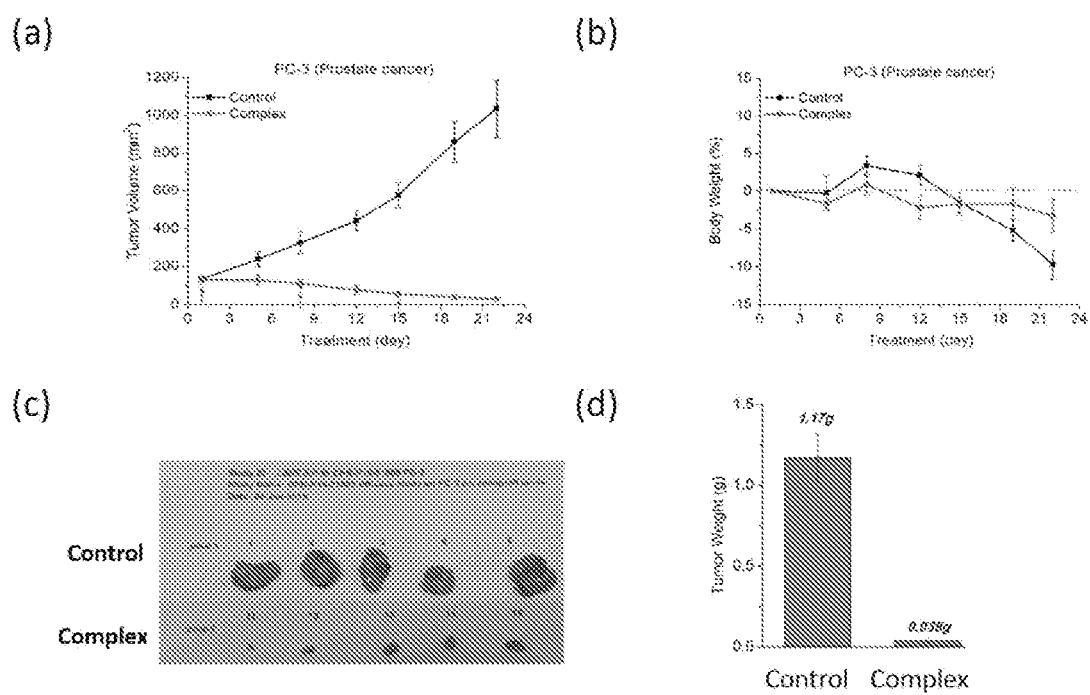
FIGS. 36A-36D show the in vivo antitumor efficacy of the complex in subcutaneous PC-3 (prostate) tumor model. Cell suspensions were injected subcutaneously on the backs of mice to establish the tumor model and when tumors were approximately 130 mm$^3$, groups of tumor bearing mice (n=5) were injected with the compositions through the tail vein.

In vivo antitumor efficacy of the complex was assessed in a subcutaneous PC-3 prostate tumor model. Cell suspensions were injected subcutaneously on the backs of mice to establish the tumor model and when tumors were approximately 130 mm$^3$, groups of tumor bearing mice (n=5) were injected with the compositions through the tail vein. FIG. 36A shows that tumor volume increased significantly with untreated mice (squares), while mice treated with the complex (circles) exhibited small tumor volumes after three injections at 3.8 mg/kg DM1 and 38 mg/kg DTX once per week. FIG. 36B shows that the body weight of mice for the control group decreased, while the body weight kept normal in the treatment group. FIG. 36C shows excised tumors for the control group (top row) and the stereocomplex treatment group (bottom row). FIG. 36D shows the tumor weight comparison of the control group (left) and stereocomplex treatment group (right).

Example 28: Antitumor Efficacy and Toxicity in a Lymphoma Tumor Model

Figures 37A, 37B:
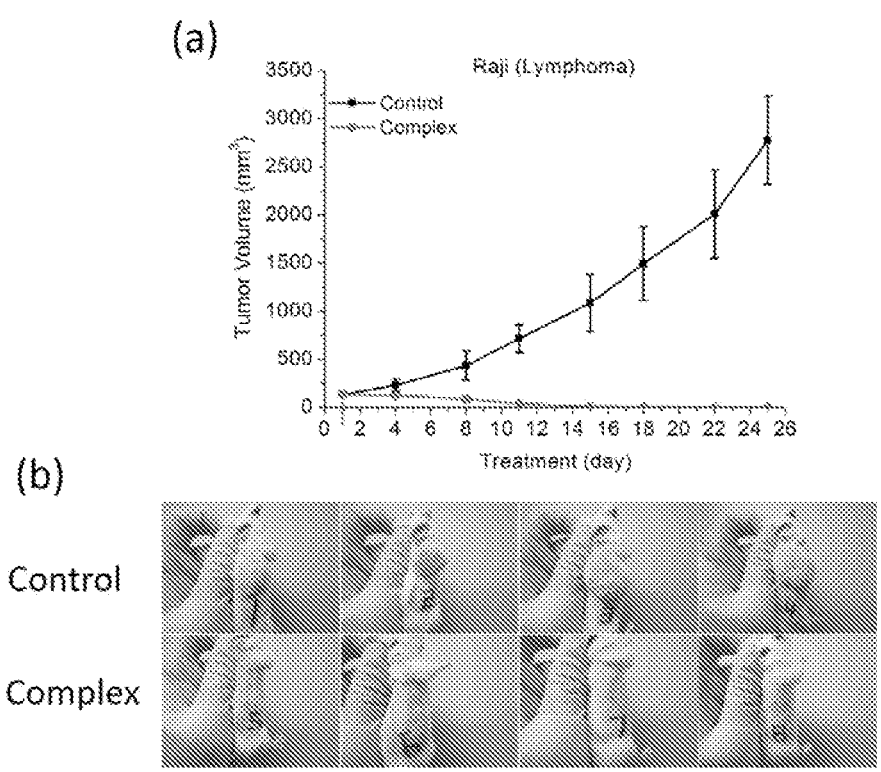
FIGS. 37A-37B show the in vivo antitumor efficacy of the complex in subcutaneous Raji (lymphoma) tumor model via intravenous injection. Cell suspensions were injected subcutaneously on the backs of mice to establish the tumor model. When tumor volume reached approximately 130 mm$^3$, groups of tumor bearing mice (n=4) were injected with the complex through the tail vein. After only one injection, three mice were tumor-free on the 15th day, and all mice had no tumors from the $22^{nd}$ day.

In vivo antitumor efficacy of the complex was assessed in a subcutaneous Raji lymphoma tumor model via intravenous injection. Cell suspensions were injected subcutaneously on the backs of mice to establish the tumor model. When tumor volume reached approximately 130 mm$^3$, groups of tumor bearing mice (n=4) were injected with the complex through the tail vein. After only one injection at 5 mg/kg DM1 and 40 mg/kg DTX, three mice were tumor-free on the 15$^{th}$ day, and all mice had no tumors from the 22$^{nd}$ day. FIG. 37A shows tumor size change for the group treated with complex (circles) versus the control group (squares). FIG. 37B shows the photos of the control mice (top row) and the treated mice (bottom row) on the 25$^{th}$ day of the trial.

Figures 38A, 38B:
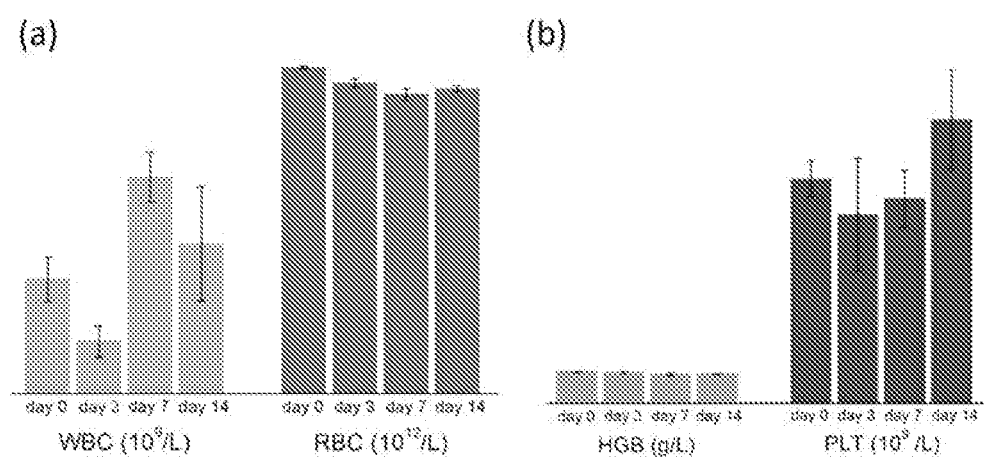
FIGS. 38A-38B show the blood parameters in nude mice after a single i.v. injection of the complex. Mice (4 animals per group) were injected with the complex at single i.v. at the dose of 5 mg/kg DM1 and 32.5 mg/kg DTX, and then were killed on days 3, 7 and 14. Blood samples were collected and analyzed for the following general parameters: white blood cell count (WBC); red blood cell count (RBC); hemoglobin concentration (HGB) and platelet count (PLT). As compared with the control (without injection) labeled as day0, RBC and HGB showed no statistical difference in the whole test. Even lower WBC and PLT were observed on day 3, they were all recovered on day 7 and kept normal on day 14.

Example 29: Blood Parameters and Clinical Chemistry Test After Single Injection of Complex Mice (4 animals per group) were injected with complex at a single i.v. dose of 5 mg/kg DM1 and 32.5 mg/kg DTX, and then were killed on days 3, 7 and 14. Blood samples were collected and analyzed for the following general parameters: white blood cell count (WBC); red blood cell count (RBC); hemoglobin concentration (HGB) and platelet count (PLT). As compared with control (without injection) labeled as day0, RBC and HGB showed no statistical difference in all tries. Even lower number of WBC and PLT were observed on day 3, they were all recovered on day 7 and kept normal on day 14, as shown in FIG. 38.

Figure 39:
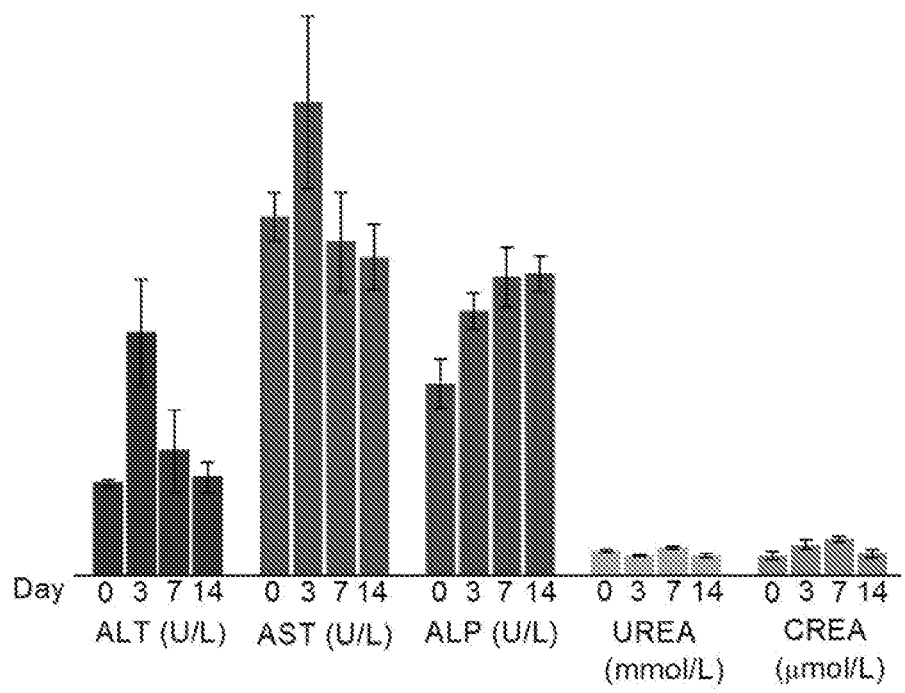
FIG. 39 shows the clinical chemistry in nude mice after a single i.v. injection of the complex formulation. Mice (4 animals per group) were injected with the complex at single i.v. at the dose of 5 mg/kg DM1 and 32.5 mg/kg DTX, and then were killed on days 3, 7 and 14. Blood samples were collected and analyzed for the following parameters: alanine aminotransferase (ALT); aspartate aminotransferase (AST); alkaline phosphatase (ALP), creatinine (CREA) and urea (UREA). As compared with control (without injection) labeled as day0, ALT and AST were elevated after injection, but recovered on day 14. There is no obvious difference in UREA and CREA, which means no nephrotoxicity at all.

FIG. 39 shows the clinical chemistry in nude mice after a single i.v. injection of complex. Mice (4 animals per group) were injected with complex at a single i.v. dose of 5 mg/kg DM1 and 32.5 mg/kg DTX, and then were killed on days 3, 7 and 14. Blood samples were collected and analyzed for the following parameters: alanine aminotransferase (ALT); aspartate aminotransferase (AST); alkaline phosphatase (ALP), creatitine (CREA) and urea (UREA). As compared with control (without injection) labeled as day0, ALT and AST were elevated after injection, but returned to normal on day 14. There is no obvious difference in UREA and CREA, which means no nephrotoxicity at all.

Figure 40:
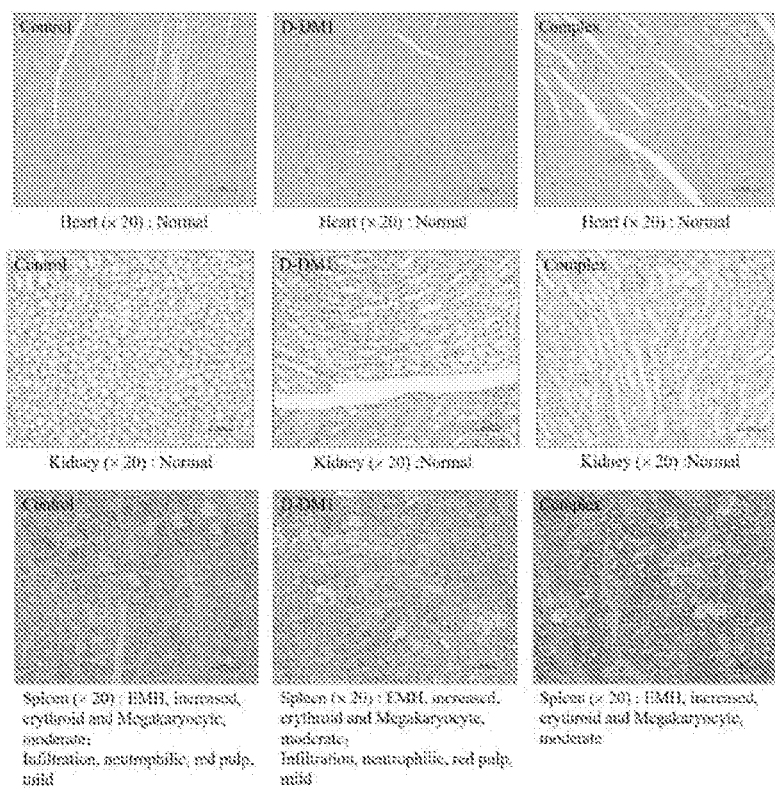
FIGS. 40 and 41 show the histopathological analysis of organs for the complex treatment group (Complex) versus the untreated group (Control) and prodrug treatment group (D-DM1) in a CNE (nasopharyngeal) tumor model. Cell suspensions were injected subcutaneously on the backs of mice to establish the tumor model and when tumors were approximately 100 mm$^3$, groups of tumor bearing mice (n=5) were injected with the compositions through the tail vein weekly for 4 consecutive weeks at doses of 4 mg/kg DM1 for D-DM1 group and 4 mg/kg DM1 with 26 mg/kg DTX for complex group, respectively. After harvesting hearts, kidneys, spleens, lungs and livers, sections were stained with hematoxylin and eosin for observation. Compared with control and D-DM1 treatment, complex treatment did not induce any damages to organs.
Figure 41:
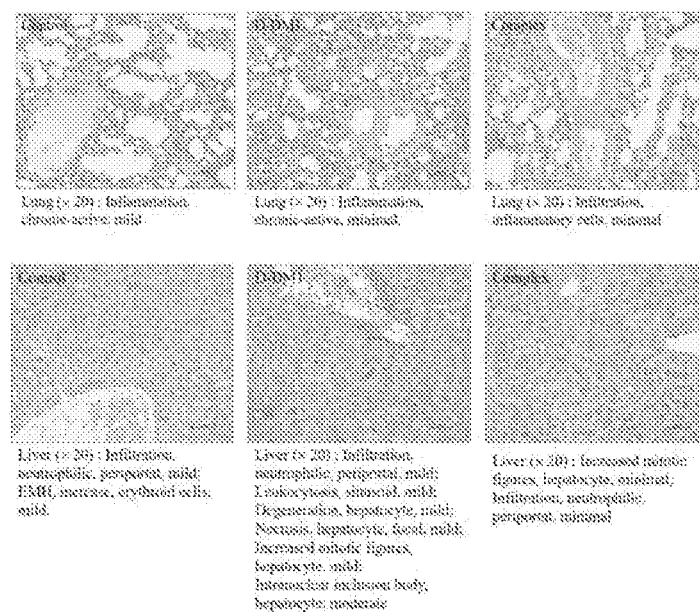

Example 30: Histopathological Analysis of Organs after Multiple Injections of Complex CNE (nasopharyngeal) tumor cell suspensions were injected subcutaneously on the backs of mice to establish the tumor model and when tumors were approximately 100 mm$^3$, groups of tumor bearing mice (n=5) were injected with the compositions through the tail vein weekly for 4 consecutive weeks at doses of 4 mg/kg DM1 for D-DM1 group and 4 mg/kg DM1 with 26 mg/kg DTX for complex group. After harvesting hearts, kidneys, spleens, lungs and livers, sections were stained with hematoxylin and eosin for observation. Compared with control and D-DM1 treatment, complex treatment did not induce any damages to organs, as shown in FIGS. 40 and 41.

Figures 42A, 42B:
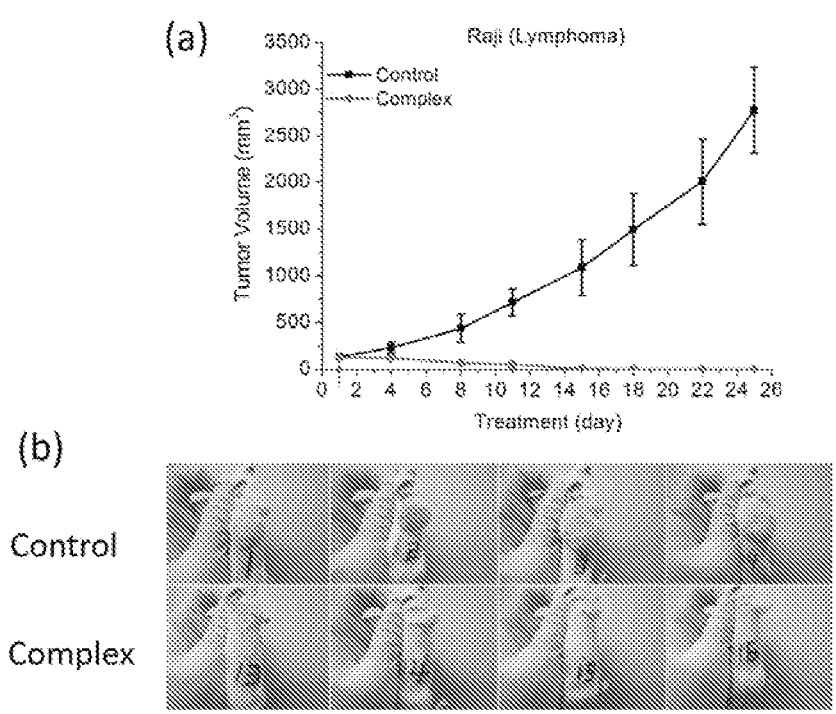
FIGS. 42A-42B show the in vivo antitumor efficacy of the complex containing glucose in subcutaneous Raji (lymphoma) tumor model via intravenous injection. Cell suspensions were injected subcutaneously on the backs of mice to establish the tumor model. When tumor volume reached approximately 130 mm³, groups of tumor bearing mice (n=4) were injected with the complex through the tail vein. After only one injection, three mice were tumor-free on the 15th day, and all mice had no tumors from the 18th day.

Example 31: Antitumor Efficacy and Toxicity in a Lymphoma Tumor Model for Complex with Glucose In vivo antitumor efficacy of the complex containing glucose was assessed in a subcutaneous Raji lymphoma tumor model via intravenous injection. Cell suspensions were injected subcutaneously on the backs of mice to establish the tumor model. When tumor volume reached approximately 130 mm$^3$, groups of tumor bearing mice (n=4) were injected with the complex through the tail vein. After only one injection at 5 mg/kg DM1 and 40 mg/kg DTX, three mice were tumor-free on the 15$^{th}$ day, and all mice had no tumors from the 18th day. FIG. 42A shows tumor size change for the group treated with complex (red line) versus the control group (black line). FIG. 42B shows the photos of the control mice (top row) and the complex containing glucose treated mice (bottom row) on the 25th day of the trial.

Example 32: Patient Studies

Stereocomplex Preparation and Administration mPEG-PLLA-hydrazone-DTX was dissolved in 2 mL THF, and mPEG-PDLA-S-S-DM1 with mPEG-PDLA was dissolved in 2 mL acetonitrile. The two solutions were mixed with one another, and the mixture was stirred at room temperature for 4 h and then was added into Di-PBS dropwise. After stirring 1 hour at room temperature, the organic solvents were rotary evaporated under vacuum. After evaporation, the stereocomplex was freeze-dried, the powder was reconstituted with water and filtered with a 200 nm filter for sterilization. The weight percentage of DM1 is about 0.8% and the weight percentage of DTX is about 6%, which means the weight ratio of DTX to DM1 is from 7 to 9.

The aqueous solution of stereocomplex was mixed with saline (500 mL) for intravenous injection. The stereocomplex was administered intravenously to each patient for approximately one hour. The stereocomplex was administered about every two weeks after the first treatment. The amount of DM1 and DTX administered to each patient below varied. The total amount of DM1 was measured, where the unit mg/m$^2$ is the body surface area calculated on height and weight. As noted below, patient 1 was administered 4 mg/m$^2$ DM1. Thus, if the patient has a body surface area (BSA) of 1.2 m$^2$, the total DM1 that was administered is 4.8 mg. As provided above, the weight percentage of DM1 in the stereocomplex is about 0.8 wt % of the stereocomplex, which means the total weight of the stereocomplex administered to the subject is about 600 mg (4.8/0.8).

Patient 1

Figure 43:
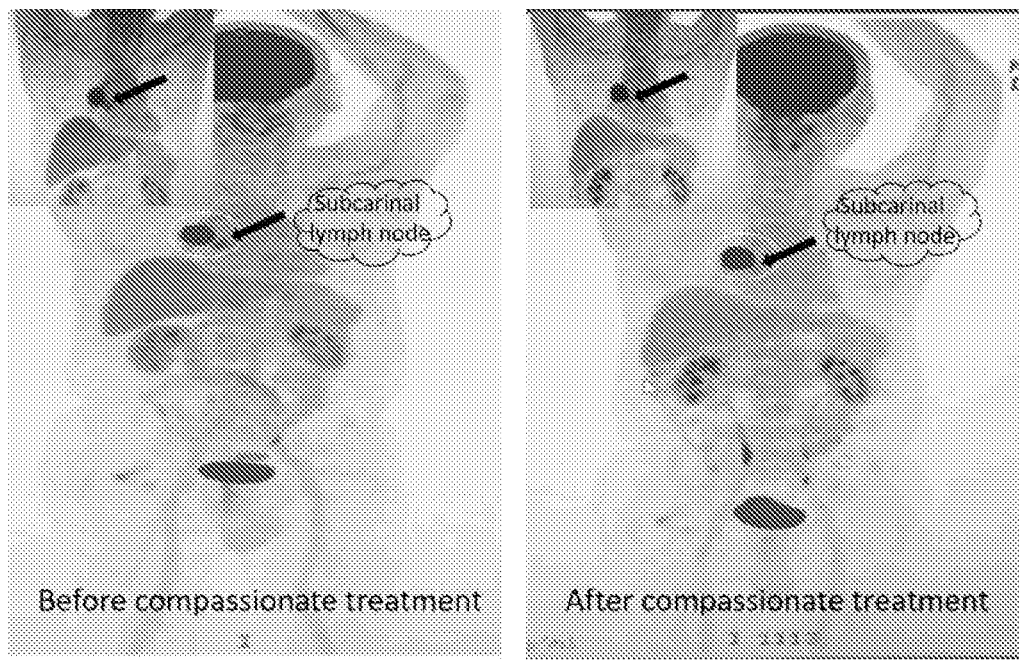
FIG. 43 shows the PET/CT images of patient 1 before and after treatment with the stereocomplex. By the comparison, the intensity of the subcarinal lymph node was reduced significantly caused due to treatment.

The first patient is a 71 year old man with squamous cell lung cancer. From the PET-CT study, AJCC cancer staging, the lung cancer was classified as stage 3 with hypermetabolic subcarinal node at the right lower lobe. After four treatments (4 mg DM1/m$^2$ per treatment) based on the PET-CT study, the intensity of the subcarinal lymph node was significantly reduced as shown in FIG. 43. The patient underwent a right total lobectomy. The 38 adjacent lymph nodes that were removed were normal without evidence of tumor on the pathology report, and the cancer was pathologically classified as stage 1. After the surgery, no further treatments were conducted, and the person was normal after a four months follow-up based on PET-CT scan.

Patient 2

The second patient is a 70 year old man with pancreatic cancer. At the beginning of the study, the size of the pancreatic head mass was 3.68 cm×3.77 cm×4.26 cm as confirmed by MR imaging (axial and coronal plans), and the biopsy revealed adenocarcinoma of pancreas. After treatment with the stereocomplex (4 mg DM1/m$^2$), the size of the pancreatic mass was 3.19 cm×3.27 cm confirmed by contrast CT (axial plans), which is a 25% decrease in cross section area. After five treatments with the stereocomplex (4 mg DM1/m$^2$ per treatment), the person underwent Whipple procedure. The surgical specimen revealed a 2 cm×1.5 cm pancreatic head tumor, which means roughly an 80% decrease in cross section area compared to the beginning MR imaging.

Patient 3

Figure 44:
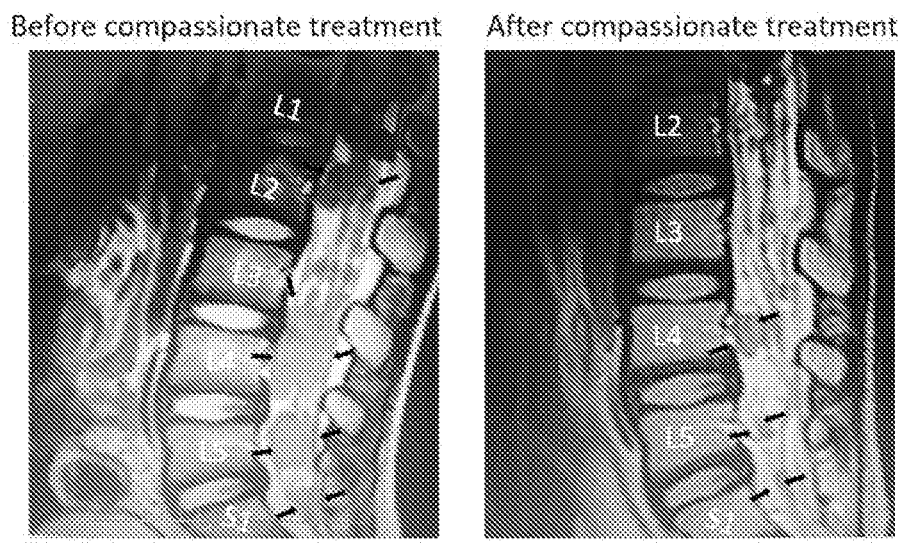
FIG. 44 shows the sagittal MR imaging of patient 3 before and after treatment with the stereocomplex. Before treatment, sagittal MR of the spine showed multiple large irregular shape masses occupying most of the spinal canal from L1 to S1, and the CSF space was minimally visible. After treatment, MR revealed marked decreased tumor masses in spinal canal between L1 to S1. Only residual small masses behind L4 and L5 were noted, where CSF space and cauda equina nerve fibers can be easily identified

The third patient is 6 year old boy with diffuse intrinsic pontine glioma (DIPG). At the beginning, the boy was treated with 30 daily times hyperfractionated radiation therapy at a total dose is 54 Gray (Gy). After that leptomeningeal metastasis was found by MR, and grade 4 diffuse intrinsic pontine glioma was confirmed by stereotactic biopsy. Before treatment with the stereocomplex, sagittal MR of the spine showed multiple large irregular shape masses occupying most of the spinal canal from L1 to S1, and the CSF space was minimally visible. After five treatments with the stereocomplex (10 mg $DM1/m^2$ per treatment), MR revealed marked decreased tumor masses in spinal canal between L1 to S1, which is about a 93% decrease of tumor volume in this area. Only residual small masses behind L4 and L5 were noted, where CSF space and cauda equina nerve fibers can be easily identified (FIG. 44).

Patient 4

Figure 45:
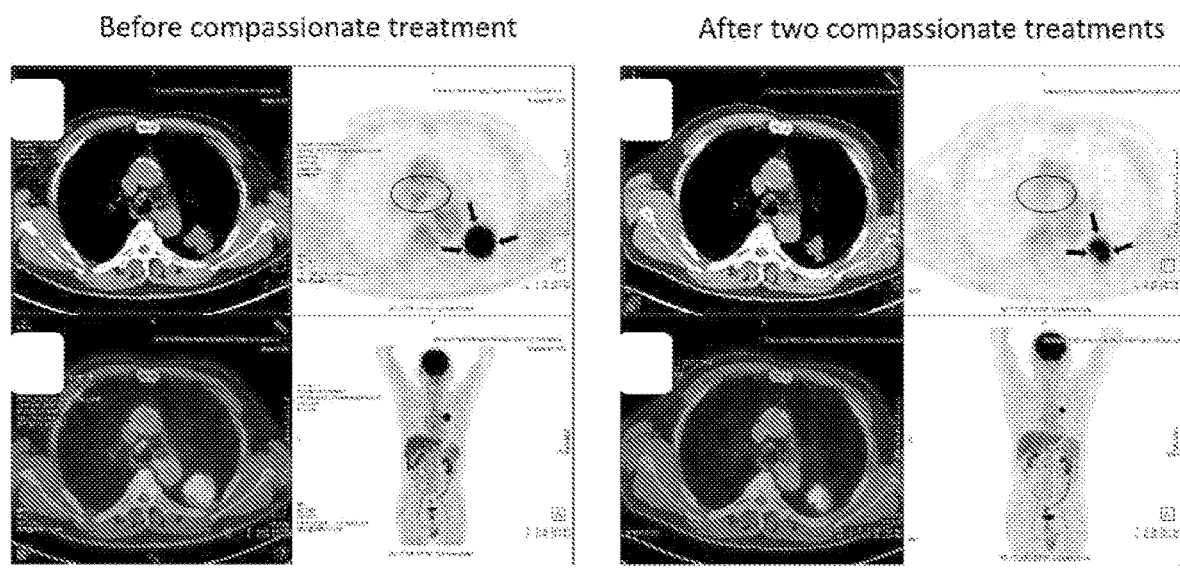
FIG. 45 shows the PET/CT images of patient 4 before and after treatment with the stereocomplex. Tumor size decreased due to treatment.
Figure 46:
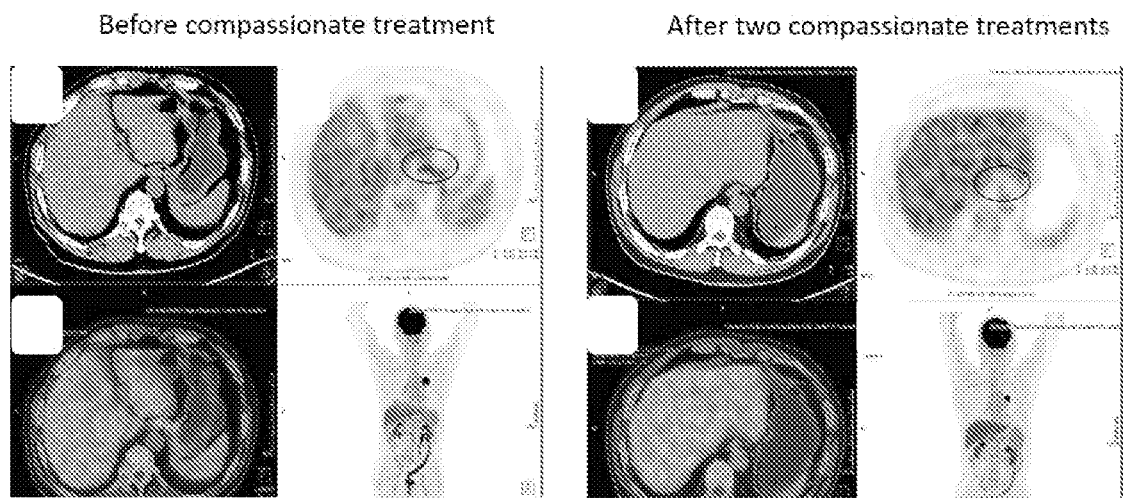
FIG. 46 shows the PET/CT image of patient 4 before and after treatment with the stereocomplex. The intensity of the uptake of mediastinal, hilar and abdominal aorta lymph node was reduced.
Figure 47:
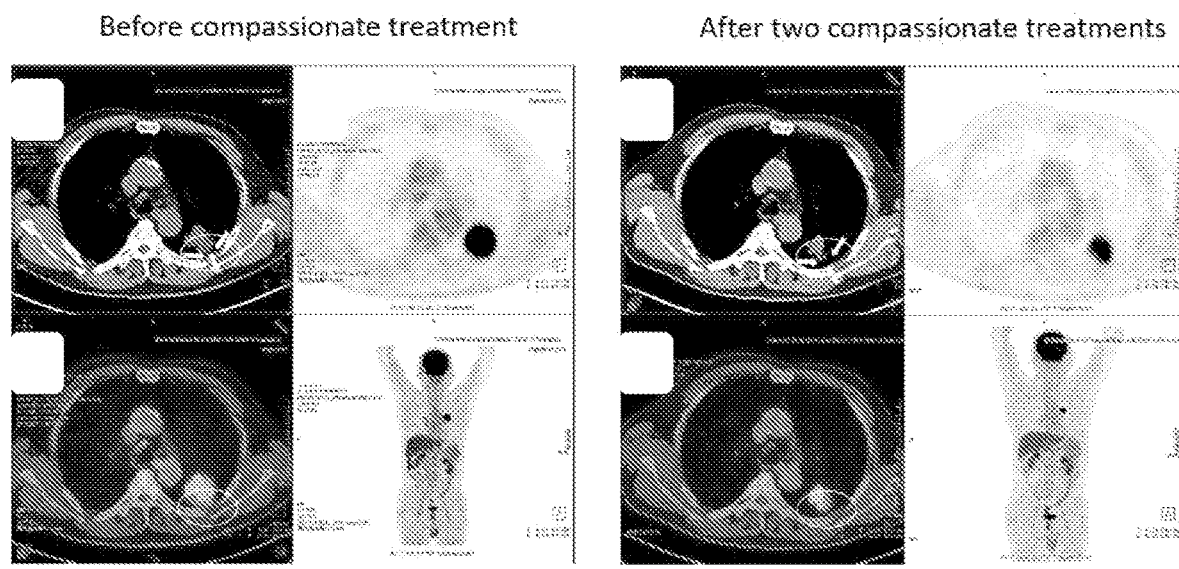
FIG. 47 shows the PET/CT images of patient 4 before and after treatment with the stereocomplex. Before treatment, the tumor was found to invade the parietal pleural; however, after treatment, the tumor and parietal pleural were found to be completely separated

The fourth patient is a 70 year old man with non-small cell lung cancer. At the beginning of the study, the size of the tumor was 3.3 cm×2.9 cm as confirmed by PET/CT. Shortly after the first treatment, the size of the tumor increased to 3.5 cm×2.8 cm as confirmed PET/CT. After two treatments with stereocomplex (12 mg $DM1/m^2$ per treatment), the PET/CT tested verified that the long diameter of tumor decreased from 3.5 cm to 2.2 cm in 15 days as shown in FIG. 45. The uptake of mediastinal, hilar and abdominal aorta lymph node changed to normal (FIG. 46). Noteworthy, before treatment, the tumor was found to invade the parietal pleural; however, after treatment, tumor size shrank, and the tumor and parietal pleural were found to be completely separated (FIG. 47).

Throughout this publication, various publications are referenced. The disclosures of these publications in their entireties are hereby incorporated by reference into this application in order to more fully describe the methods, compositions, and compounds herein.

Various modification and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed:

1. A stereocomplex comprising components I and II, wherein the component I is represented by the formula (III) below:

wherein n1 is from 45 to 90; $m^1$ is from 15 to 60; o is from 1 to 4; and the stereochemistry at $C^a$ is R; and wherein the component II is represented by the following formula:

$$X^2\text{-}Y^2\text{-}L^2\text{-}Z^2 \quad (II)$$

wherein $X^2$ is a polyethylene glycol having a molecular weight from 1,000 Da to 5,000 Da;

$Y^2$ is PLLA having a molecular weight from 700 Da to 5,000 Da;

$L^2$ is a cleavable linker containing a cleavable group selected from the group consisting of a disulfide group, an ester group, a hydrazone group, an acetal group, an imine group, a β-thiopropionate group, and an amide group;

$Z^2$ is an anti-cancer agent that is different from mertansine (DM1) in formula (III); and wherein a ratio of a total number of D-lactic acid units in the stereocomplex to a total number of L-lactic acid units in the stereocomplex is from 0.9:1.1 to 1.1:0.9.

2. The stereocomplex of claim 1, wherein $X^2$ is a monomethoxy polyethylene glycol having a molecular weight from 1,000 Da to 5,000 Da.

3. The stereocomplex of claim 1, wherein $Z^2$ is paclitaxel, doxorubicin, gemcitabine, cisplatin, methotrexate, 5-fluorouracil, betulinic acid, amphotericin B, diazepam, nystatin, propofol, testosterone, estrogen, prednisolone, prednisone, 2,3-mercaptopropanol, progesterone, docetaxel, a maytansinoid, a PD-1 inhibitor, a PD-L1 inhibitor, a protein kinase inhibitor, a P-glycoprotein inhibitor, an autophage inhibitor, a PARP inhibitor, an aromatase inhibitor, a monoclonal antibody, a photosensitizer, a radiosensitizer, an interleukin, or an antiandrogen.

4. The stereocomplex of claim 3, wherein the maytansinoid is ansamitocin or ravtansine.

5. The stereocomplex of claim 1, wherein the molar ratio of mertansine in formula (III) to $Z^2$ is from 10:1 to 1:10.

6. The stereocomplex of claim 1, wherein $Z^2$ is docetaxel.

7. The stereocomplex of claim 1, wherein for the component II, $X^2$ is monomethoxy polyethylene glycol having a molecular weight from 2,000 Da to 4,000 Da, the number of L-lactic acid units is from 15 to 60, $L^2$ comprises an ester, hydrazone or disulfide group, and $Z^2$ is docetaxel.

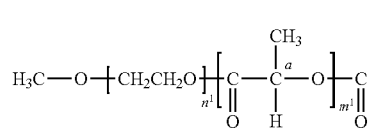

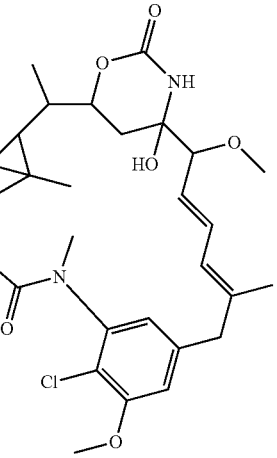

8. The stereocomplex of claim 7, wherein the molar ratio of mertansine in formula (III) to docetaxel is from 4:1 to 1:10.

9. The stereocomplex of claim 7, wherein the component II has the following structure:

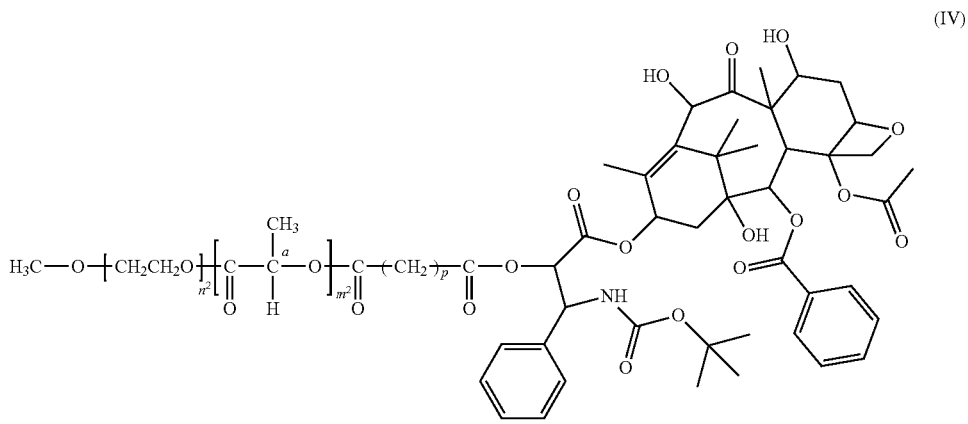

wherein $n^2$ is from 45 to 90;
$m^2$ is from 15 to 60;
p is from 0 to 7; and
the stereochemistry at $C^a$ is S.

10. The stereocomplex of claim 9, wherein p is 2.

11. The stereocomplex of claim 7, wherein the component II has the following structure:

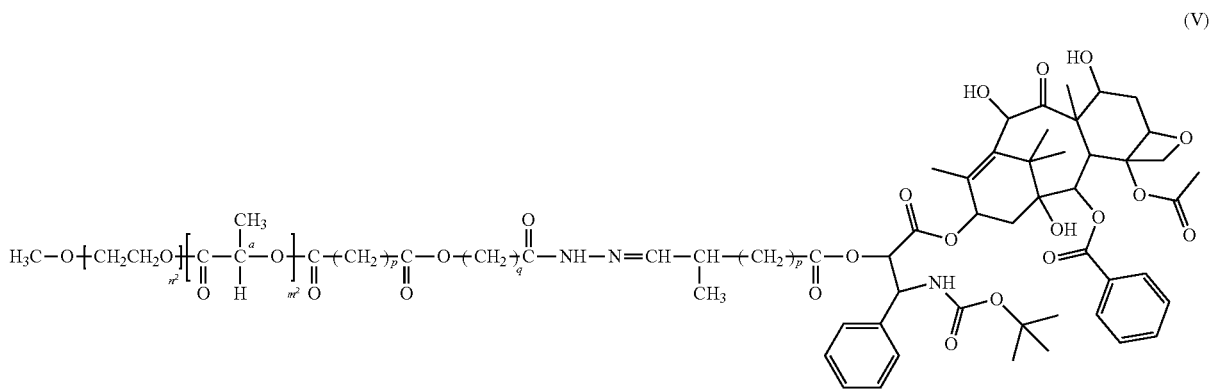

wherein $n^2$ is from 45 to 90;
$m^2$ is from 15 to 60;
each p is independently from 0 to 7;
q is from 1 to 7; and
the stereochemistry at $C^a$ is S.

12. The stereocomplex of claim 11, wherein each p is 2, and q is 3.

13. The stereocomplex of claim 7, wherein the component II has the following structure

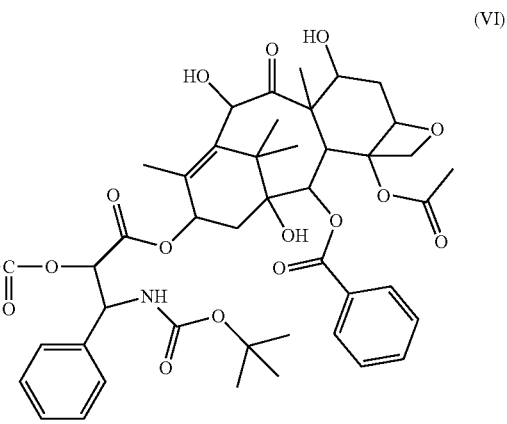

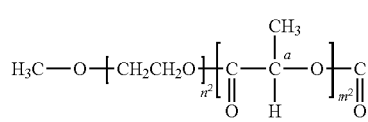

(VI)

wherein $n^2$ is from 45 to 90;

$m^2$ is from 15 to 60;

each p is independently from 0 to 7;

the stereochemistry at $C^a$ is S.

14. The stereocomplex of claim 13, wherein each p is 2.

15. The stereocomplex of claim 1, wherein the stereocomplex further comprises component VII $$X^3\text{-}Y^3 \quad (VII)$$

wherein $X^3$ is a polyethylene glycol having a molecular weight from 1,000 Da to 5,000 Da; and $Y^3$ is PDLA or PLLA.

16. The stereocomplex of claim 15, wherein $X^3$ is monomethoxy polyethylene glycol having a molecular weight from 1,000 Da to 5,000 Da.

17. The stereocomplex of claim 15, wherein $X^3$ is monomethoxy polyethylene glycol having a molecular weight from 2,000 Da to 4,000 Da, and the number of L-lactic acid units or D-lactic acid units present in PDLA or PLLA is from 15 to 60.

18. The stereocomplex of claim 1, wherein the stereocomplex further comprises component VIII $$TA\text{-}X^4\text{-}Y^4 \quad (VIII)$$

wherein $X^4$ is a polyethylene glycol having a molecular weight from 1,000 Da to 5,000 Da;

$Y^4$ is PDLA or PLLA; and

TA is a targeting group.

19. The stereocomplex of claim 18, wherein the molecular weight of $X^4$ is greater than the molecular weight of $X^2$.

20. The stereocomplex of claim 18, wherein $X^4$ has a molecular weight from 2,000 Da to 4,000 Da, and the number of L-lactic acid units or D-lactic acid units present in PDLA or PLLA is from 15 to 60.

21. The stereocomplex of claim 18, wherein TA is a ligand.

22. The stereocomplex of claim 18, wherein the component VIII has the structure

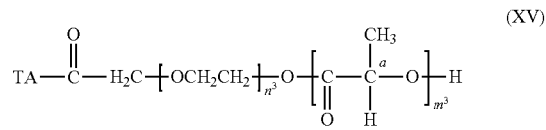

(XV)

wherein $n^3$ is from 45 to 90;

$m^3$ is from 15 to 60; and the stereochemistry at $C^a$ is R or S.

23. The stereocomplex of claim 18, wherein TA is an unsubstituted or substituted sugar.

24. The stereocomplex of claim 23, wherein the sugar is ribose, galactose, mannose, fructose, fuculose, glucosamine, or fucoidan.

25. The stereocomplex of claim 18, wherein TA is glucose or substituted glucose.

26. The stereocomplex of claim 18, wherein TA is alkyl substituted glucose.

27. The stereocomplex of claim 18, wherein TA is methyl-α-glucose or methyl-β-glucose.

28. The stereocomplex of claim 1, wherein the stereocomplex further comprises an adjuvant.

29. The stereocomplex of claim 28, wherein the adjuvant comprises a stroma-rupturing agent, an anti-fibrosis agent, an aromatase inhibitor, an immune-suppressing agent, an estrogen blocker, a gonadotropin-releasing hormone agonist, an estrogen modulator, a progestin therapeutic, a LHRH agonist, an androgen-reducing agent, an anti-androgen, an immune-suppressing agent, or any combination thereof.

30. The stereocomplex of claim 28, wherein the adjuvant comprises a stroma-rupturing agent, wherein the stroma-rupturing agent comprises losartan, azilsartan, candesartan, eprosartan, irbesartan, olmesartan, telmisartan, valsartan, luteolin, quercetin, genistein, catechin, cyaniding, naringenin, delphinidin, malvidin, petunidin, peonidin, pelargonidin, gallocatechin, catechin-3-gallate, epicatechin, epigallocatechin, daidzein, glycetein, equol, kaempherol, myricetin, eriodictyol, hesperitin, taxifolin, or any combination thereof.

31. The stereocomplex of claim 28, wherein the adjuvant comprises an anti-fibrosis agent, wherein the anti-fibrosis agent comprises pirfenidone, mimosine, ciclopirox, diodone, bemegride, deferiprone, etanrecept, bosentan, sildenafil, nintedanib, colchicine, or a combination thereof.

32. The stereocomplex of claim 1, wherein the stereocomplex has an average diameter from 50 nm to 200 nm as measured by dynamic light scattering.

33. A pharmaceutical composition comprising the stereocomplex of claim 1 and a pharmaceutically acceptable carrier.

34. A method for treating cancer in a subject comprising administering to the subject the stereocomplex of claim 1.

35. The method of claim 34, wherein the cancer is pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumor.

36. A method for reducing a tumor in a subject comprising administering to the subject the stereocomplex of claim 1.

37. The method of claim 36, wherein the stereocomplex is administered to the subject by intravenous injection.

38. The method of claim 36, wherein
the component II has the following structure:

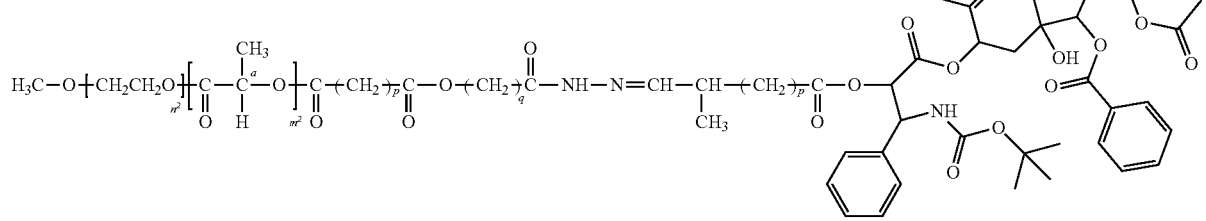

(V)

wherein $n^2$ is from 45 to 90;
$m^2$ is from 15 to 60;
each p is independently from 0 to 7;
q is from 1 to 7; and
the stereochemistry at $C^a$ is S;
wherein the ratio of the total number of D-lactic acid units in the stereocomplex to the total number of L-lactic acid units in the stereocomplex is from 0.9:1.1 to 1.1:0.9.

39. The method of claim 38, wherein each p is 2; and q is 3.

40. A stereocomplex comprising components I and II, wherein the component I is represented by the following formula:

$$X^1\text{-}Y^1\text{-}L^1\text{-}Z^1 \qquad (I)$$

wherein
$X^1$ is a polyethylene glycol having a molecular weight from 1,000 Da to 5,000 Da;

$Y^1$ is PDLA having a molecular weight from 700 Da to 5,000 Da;

$L^1$ is a cleavable linker containing a cleavable group selected from the group consisting of a disulfide group, an ester group, a hydrazone group, an acetal group, an imine group, a β-thiopropionate group, and an amide group;

$Z^1$ is an anti-cancer agent that is different from docetaxel; and wherein the component II is represented by formula (V) below:

(V)

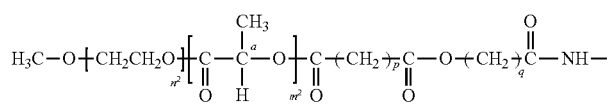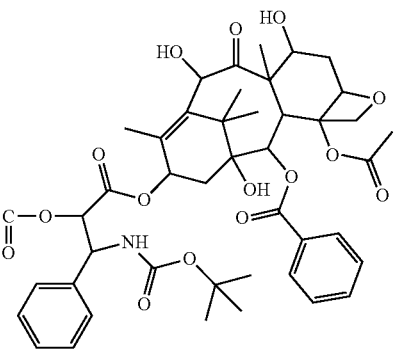

wherein $n^2$ is from 45 to 90;
$m^2$ is from 15 to 60;
each p is independently from 0 to 7;
q is from 1 to 7; and
the stereochemistry at $C^a$ is S;
wherein a ratio of a total number of D-lactic acid units in the stereocomplex to a total number of L-lactic acid units in the stereocomplex is from 0.9:1.1 to 1.1:0.9.

41. The stereocomplex of claim 40, wherein $X^1$ is a monomethoxy polyethylene glycol having a molecular weight from 1,000 Da to 5,000 Da.

42. The stereocomplex of claim 40, wherein $Z^1$ is paclitaxel, doxorubicin, gemcitabine, cisplatin, methotrexate, 5-fluorouracil, betulinic acid, amphotericin B, diazepam, nystatin, propofol, testosterone, estrogen, prednisolone, prednisone, 2,3-mercaptopropanol, progesterone, a maytansinoid, a PD-1 inhibitor, a PD-L1 inhibitor, a protein kinase inhibitor, a P-glycoprotein inhibitor, an autophage inhibitor, a PARP inhibitor, an aromatase inhibitor, a monoclonal antibody, a photosensitizer, a radiosensitizer, an interleukin, or an antiandrogen.

43. The stereocomplex of claim 42, wherein the maytansinoid is ansamitocin, mertansine (DM1) or ravtansine.

44. The stereocomplex of claim 40, wherein the molar ratio of $Z^1$ to docetaxel in formula (V) is from 10:1 to 1:10.

45. The stereocomplex of claim 40, wherein $Z^1$ is mertansine.

46. The stereocomplex of claim 40, wherein for the component I, $X^1$ is monomethoxy polyethylene glycol having a molecular weight from 2,000 Da to 4,000 Da, the number of D-lactic acid units is from 15 to 60, $L^1$ comprises a disulfide group, and $Z^1$ is mertansine (DM1).

47. A pharmaceutical composition comprising the stereocomplex of claim 40 and a pharmaceutically acceptable carrier.

48. A method for treating cancer in a subject comprising administering to the subject the stereocomplex of claim 40.

49. The method of claim 48, wherein the cancer is pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumor.

50. A stereocomplex comprising components I and II, wherein the component I has the following structure:

(III)

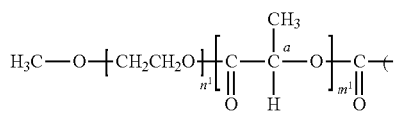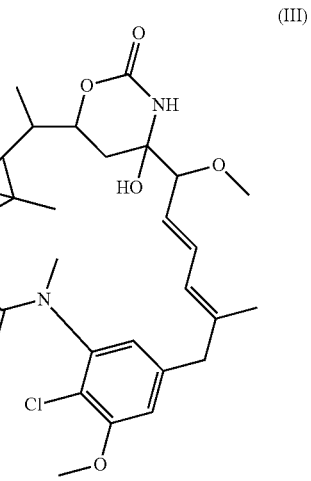

wherein $n^1$ is from 45 to 90;
$m^1$ is from 15 to 60;
o is from 1 to 4; and
the stereochemistry at $C^a$ is R; and
the component II has the following structure:

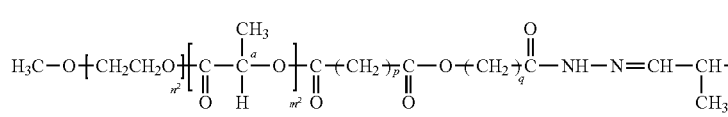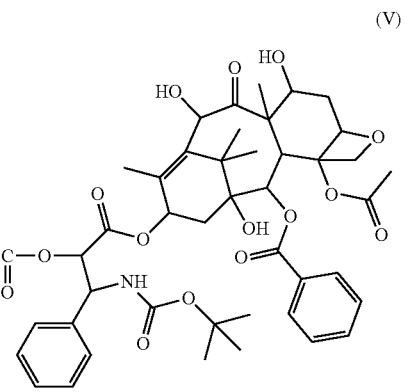

(V)

wherein $n^2$ is from 45 to 90;
$m^2$ is from 15 to 60;
each p is independently from 0 to 7;
q is from 1 to 7; and
the stereochemistry at $C^a$ is S;
wherein the ratio of the total number of D-lactic acid units in the stereocomplex to the total number of L-lactic acid units in the stereocomplex is from 0.9:1.1 to 1.1:0.9.

51. The stereocomplex of claim 50, wherein o is 2; each p is 2; and q is 3.

52. A pharmaceutical composition comprising the stereocomplex of claim 50 and a pharmaceutically acceptable carrier.

53. A method for treating cancer in a subject comprising administering to the subject the stereocomplex of claim 50.

54. The method of claim 53, wherein the cancer is pancreatic cancer, non-small cell lung cancer, small cell lung cancer, ovary cancer, nasopharyngeal cancer, breast cancer, ovarian cancer, prostate cancer, colon cancer, gastric adenocarcinoma, head cancer, neck cancer, brain cancer, oral cancer, pharynx cancer, thyroid cancer, esophagus cancer, gall bladder cancer, liver cancer, rectum cancer, kidney cancer, uterine cancer, bladder cancer, testis cancer, lymphoma, myeloma, melanoma, leukemia, or a nonspecified solid tumor.

* * * * *